US012629352B2

(12) United States Patent
Maitra et al.

(10) Patent No.: US 12,629,352 B2
(45) **Date of Patent: *May 19, 2026**

(54) METHODS AND USES FOR APELIN RECEPTOR AGONISTS

(71) Applicant: RESEARCH TRIANGLE INSTITUTE, Research Triangle Park, NC (US)

(72) Inventors: Rangan Maitra, Cary, NC (US); Sanju Narayanan, Morrisville, NC (US); Kenneth S. Rehder, Durham, NC (US); Scott P. Runyon, Hillsborough, NC (US)

(73) Assignee: RESEARCH TRIANGLE INSTITUTE, Durham, NC (US)

( * ) Notice: Subject to any disclaimer, the term of this patent is extended or adjusted under 35 U.S.C. 154(b) by 1073 days.

This patent is subject to a terminal disclaimer.

(21) Appl. No.: 17/637,659

(22) PCT Filed: Aug. 28, 2020

(86) PCT No.: PCT/US2020/048375

§ 371 (c)(1),
(2) Date: Feb. 23, 2022

(87) PCT Pub. No.: WO2021/041791

PCT Pub. Date: Mar. 4, 2021

(65) Prior Publication Data

US 2022/0280483 A1 Sep. 8, 2022

Related U.S. Application Data

(60) Provisional application No. 62/893,661, filed on Aug. 29, 2019.

(51) Int. Cl.

*A61K 31/415* (2006.01)
*A61K 31/4418* (2006.01)
*A61K 31/496* (2006.01)
*A61P 11/00* (2006.01)

(52) U.S. Cl.

CPC ........ *A61K 31/415* (2013.01); *A61K 31/4418* (2013.01); *A61K 31/496* (2013.01); *A61P 11/00* (2018.01)

(58) Field of Classification Search

CPC .............. A61K 31/415; A61K 31/4418; A61K 31/454; A61K 31/496; A61P 11/00

See application file for complete search history.

(56) References Cited

U.S. PATENT DOCUMENTS

| | | | |
|---|---|---|---|
| 4,795,484 | A | 1/1989 | Aoki et al. |
| 5,304,121 | A | 4/1994 | Sahatjian |
| 5,420,141 | A | 5/1995 | Boigegrain et al. |
| 5,502,059 | A | 3/1996 | Labeeuw et al. |
| 5,523,455 | A | 6/1996 | Labeeuw et al. |
| 5,585,497 | A | 12/1996 | Labeeuw et al. |
| 5,624,941 | A | 4/1997 | Barth et al. |
| 5,723,483 | A | 3/1998 | Labeeuw et al. |
| 5,744,491 | A | 4/1998 | Boigegrain et al. |
| 5,886,026 | A | 3/1999 | Hunter et al. |
| 5,925,661 | A | 7/1999 | Labeeuw et al. |
| 5,936,123 | A | 8/1999 | Labeeuw et al. |
| 5,939,449 | A | 8/1999 | Labeeuw et al. |
| 5,965,579 | A | 10/1999 | Labeeuw et al. |
| 6,028,084 | A | 2/2000 | Barth et al. |
| 6,075,121 | A | 6/2000 | Simon et al. |
| 6,099,562 | A | 8/2000 | Ding et al. |
| 6,172,239 | B1 | 1/2001 | Labeeuw et al. |
| 6,803,031 | B2 | 10/2004 | Rabinowitz et al. |
| 7,014,866 | B2 | 3/2006 | Infeld et al. |
| 7,186,741 | B2 | 3/2007 | Feenstra et al. |
| 7,531,592 | B2 | 5/2009 | Dubouis et al. |
| 8,252,790 | B2 | 8/2012 | Yamagishi et al. |
| 8,354,557 | B2 | 1/2013 | Liu et al. |
| 8,513,244 | B2 | 8/2013 | Gendron et al. |
| 8,704,001 | B2 | 4/2014 | Masse |
| 10,100,059 | B2 | 10/2018 | Runyon et al. |
| 10,377,718 | B2 | 8/2019 | Runyon et al. |
| 10,954,247 | B2 | 3/2021 | Runyon et al. |
| 2004/0063691 | A1 | 4/2004 | Smith et al. |
| 2004/0082496 | A1 | 4/2004 | Acton et al. |
| 2004/0235854 | A1 | 11/2004 | Kruse et al. |
| 2005/0054679 | A1 | 3/2005 | Kruse et al. |
| 2006/0014813 | A1 | 1/2006 | Connelly et al. |
| 2006/0079502 | A1 | 4/2006 | Lang |
| 2006/0094744 | A1 | 5/2006 | Maryanoff et al. |
| 2006/0264470 | A1 | 11/2006 | Barth et al. |

(Continued)

FOREIGN PATENT DOCUMENTS

| | | | |
|---|---|---|---|
| CA | 2136893 | | 6/1995 |
| CN | 1556703 | A | 12/2004 |

(Continued)

OTHER PUBLICATIONS

Richeldi et. al., The Lancet, vol. 389, pp. 1941-1952, publ. Mar. 29, 2017 (Year: 2017).*

Takakura, JP 2008-013436 A, publ. Jan. 24, 2008, English language translation (Year: 2008).*

Plummer Christopher W., et al. "Synthesis and activity of 4, 5-diarylimidazoles as human CB1 receptor inverse agonists." Bioorganic & medicinal chemistry letters 15.5 (2005): 1441-1446.

CAS Nos. 1415511-09-09, 2022.

CAS Nos. 1415511-07-7, 2022.

Alvarez et al., "Structure-Activity Study of Bioisosteric Trifluoromethyl and Pentafluorosulfanyl Indole Inhibitors of the AAA ATPase p97", Acs. Med. Chem. Let., 2015, pp. 1225-1230, vol. 6.

Andersen et al.; "Apelin and pulmonary hypertension", Pulm. Circ. Jul.-Sep. 2011, pp. 334-346, vol. 1, No. 3.

(Continued)

*Primary Examiner* — Sarah Pihonak

(74) *Attorney, Agent, or Firm* — Barnes & Thornburg LLP

(57) ABSTRACT

The present disclosure provides a method for treating idiopathic pulmonary fibrosis in a patient in need thereof comprising administering a therapeutically effective amount of an apelin receptor agonist.

16 Claims, 15 Drawing Sheets

(56) References Cited

U.S. PATENT DOCUMENTS

| | | | | |
|---|---|---|---|---|
| 2007/0213302 | A1 | 9/2007 | McElroy et al. | |
| 2007/0219210 | A1 | 9/2007 | Kanaya et al. | |
| 2008/0125409 | A1 | 5/2008 | Kanaya et al. | |
| 2010/0160323 | A1 | 6/2010 | Bischoff et al. | |
| 2010/0331540 | A1 | 12/2010 | Shimodaira et al. | |
| 2014/0081019 | A1 | 3/2014 | Atzrodt et al. | |
| 2014/0094450 | A1 | 4/2014 | Hachtel et al. | |
| 2014/0341994 | A1 | 11/2014 | Sommer et al. | |
| 2015/0299166 | A1 | 10/2015 | Tung | |
| 2016/0058705 | A1* | 3/2016 | Rajadas | A61K 9/0019 514/1.9 |
| 2016/0207889 | A1 | 7/2016 | Runyon et al. | |
| 2017/0174633 | A1 | 6/2017 | Thomas et al. | |

FOREIGN PATENT DOCUMENTS

| | | | | |
|---|---|---|---|---|
| CN | 101519430 | A | 9/2009 | |
| CN | 104640846 | A | 5/2015 | |
| CN | 106459004 | B | 9/2020 | |
| CO | NC20160004908 | | 3/2017 | |
| EP | 0576357 | B1 | 3/1997 | |
| EP | 0477049 | B1 | 12/1999 | |
| EP | 1903052 | A2 | 3/2008 | |
| EP | 3526209 | A1 | 8/2019 | |
| JP | S58194866 | A | 11/1983 | |
| JP | S5998004 | A | 6/1984 | |
| JP | H04244065 | A | 9/1992 | |
| JP | 2005504805 | A | 2/2005 | |
| JP | 2005508384 | A | 3/2005 | |
| JP | 2008013436 | A * | 1/2008 | A61K 38/1709 |
| JP | 2009529540 | A | 8/2009 | |
| JP | 2010500336 | A | 1/2010 | |
| JP | 2013231000 | A | 11/2013 | |
| JP | 2014525912 | A | 10/2014 | |
| JP | 2015521193 | A | 7/2015 | |
| JP | 2015524449 | A | 8/2015 | |
| JP | 2017523126 | A | 8/2017 | |
| JP | 2019501899 | A | 1/2019 | |
| JP | 6767878 | B2 | 10/2020 | |
| MX | 2016014890 | A | 5/2017 | |
| RU | 2141479 | C1 | 11/1999 | |
| RU | 2325382 | C2 | 5/2008 | |
| WO | 2003027076 | A2 | 4/2003 | |
| WO | 2003040107 | A1 | 5/2003 | |
| WO | 2004026301 | A1 | 4/2004 | |
| WO | 2005063737 | A1 | 7/2005 | |
| WO | 2005099705 | A2 | 10/2005 | |
| WO | 2006043594 | A1 | 4/2006 | |
| WO | 2006133926 | A1 | 12/2006 | |
| WO | 2007106721 | A2 | 9/2007 | |
| WO | 2008017932 | A2 | 2/2008 | |
| WO | 2008098104 | A1 | 8/2008 | |
| WO | 2010053545 | A2 | 5/2010 | |
| WO | 2011005052 | A2 | 1/2011 | |
| WO | 2011012630 | A1 | 2/2011 | |
| WO | 2011156557 | A2 | 12/2011 | |
| WO | 2012166387 | A1 | 12/2012 | |
| WO | 2013014204 | A2 | 1/2013 | |
| WO | 2013079223 | A1 | 6/2013 | |
| WO | 2013178362 | A1 | 12/2013 | |
| WO | 2014023367 | A1 | 2/2014 | |
| WO | 2014044738 | A1 | 3/2014 | |
| WO | 2014053533 | A1 | 4/2014 | |
| WO | 2014152588 | A1 | 9/2014 | |
| WO | 2014169280 | A2 | 10/2014 | |
| WO | 2015058067 | A1 | 4/2015 | |
| WO | 2015184011 | A2 | 12/2015 | |
| WO | 2015188073 | A1 | 12/2015 | |
| WO | 2017100558 | A1 | 6/2017 | |
| WO | 2018010398 | A1 | 1/2018 | |
| WO | 2018071526 | A1 | 4/2018 | |

OTHER PUBLICATIONS

Baxendale et al., "The Synthesis of Neurotensin Antagonist SR 48692 for Prostate Cancer Research," Bioorg. Med. Chem., 2013, vol. 21, pp. 4378-4387.

Carpene et al., "Expanding role for the apelin/APJ system in physiopathology," J. Physiol. Biochem., 2007, 63(4) pp. 359-374.

CAS Registry No. 1831835-31-4 which entered STN on Jun. 24, 2016.

CAS Registry No. 1423365-99-4, which entered STN on Mar. 14, 2013.

CAS Registry No. 1569560-23-1, which entered STN on Mar. 18, 2014.

CAS Registry No. 1569675-43-9, which entered STN on Mar. 18, 2014 (Year: 2014).

CAS Registry No. 1580321-28-3, which entered STN on Apr. 4, 2014 (Year: 2014).

CAS Registry No. 1830232-36-4 which entered STN on Jun. 24, 2016.

CAS Registry No. 1938292-99-9 which entered STN on Jun. 24, 2016.

CAS Registry No. 1938533-13-1 which entered STN on Jun. 24, 2016.

CAS Registry No. 931620-33-6, which entered STN on Apr. 22, 2007.

CAS Registry No. 1171327-99-3 which entered STN Aug. 2, 2009.

CAS Registry No. 1185029-85-9 which entered STN Sep. 16, 2009.

CAS Registry No. 1185070-07-8 which entered STN Sep. 16, 2009.

CAS Registry No. 1185080-91-4 which entered STN Sep. 16, 2009.

CAS Registry No. 1185108-25-1 which entered STN on Sep. 16, 2009.

CAS Registry No. 1185123-59-4 which entered STN on Sep. 16, 2009.

CAS Registry No. 1189436-73-4 which entered STN Oct. 22, 2009.

CAS Registry No. 1189470-51-6 which entered STN on Oct. 22, 2009.

CAS Registry No. 1189643-98-8 which entered STN Oct. 23, 2009.

CAS Registry No. 1189728-26-4 which entered STN Oct. 23, 2009.

CAS Registry No. 1189885-22-0 which entered STN Oct. 25, 2009.

CAS Registry No. 1190009-39-2 which entered STN Oct. 25, 2009.

CAS Registry No. 1192964-68-3 which entered STN Nov. 20, 2009.

Charo et al., "Endogenous regulation of cardiovascular function by apelin-APJ," Am. J. Physiol. Heart Circ. Physiol, 2009, 297, H1904-H1913.

Cho, K-I, et al., "Targeting the cyclophilin domain of ran-binding protein 2 (Ranbp2) with novel small molecules to control the proteostasis of STAT3, mnRNPA2B1 and M-Opsin", ACS Chemical Neuroscience (Aug. 2015), vol. 6, No. 8, pp. 1476-1485.

Cobellis et al. "Modulation of apelin and APJ receptor in normal and preeclampsia-complicated placentas," Jan. 2007, Histol. Histopathol. 22(1) pp. 1-8.

Duncton et al., "A one-pot synthesis of tetrazolones from acid chlorides: understanding functional group compatibility, and application to the late-stage functionalization of marketed drugs", Org. Biomol. Chem (2016) vol. 14, pp. 9338-9342.

Dyck, B, et al., "Potent imidazole and triazole CP1receptor antagonists related to SR141716", Bioorganic & Medicinal Chemistry Letters, (2004), vol. 14, No. 5, pp. 1151-1154.

Fleisher et al., "Improved Review oral drug delivery: solubility limitations of prodrugs", Advanced Drug Delivery Reviews, 1996, p. 115-130, vol. 19.

Freireich et al., "Quantitative comparison of toxicity of anticancer agents in mouse, rat, hamster, dog, monkey, and man," Cancer Chemother. Rep., 1966, 50(4) pp. 219-244.

Geigy Pharmaceuticals, "Scientific Tables Excerpts From the Seventh Edition—Documenta Geigy," Ardsley, New York, 1970, pp. 537.

Giddings et al., "Development of a functional HTS assay for the APJ receptor," 2010, International Journal of High Throughput Screening, 1, pp. 39-47.

Gross, TJ et al, "Idiopathic Pulmonary Fibrosis" NEngl J Med, 2001, pp. 517-525, vol. 345, No. 7.

(56) References Cited

OTHER PUBLICATIONS

Habata et al., "Apelin, the natural ligand of the orphan receptor APJ, is abundantly secreted in the colostrum," Biochim. Biophys. Acta., 1999, 1452(1), pp. 25-35.
Hagihara, M. et al., "Reassignment of stereochemistry and total synthesis of the thrombin inhibitor cyclotheonamide B," J. Amer. Chem. Soc. 1992, 114(16) pp. 6570-6571.
Hershberger et al., "Imidazole-derived agonists for the neurotensin 1 receptor" Bioorg. Med. Chem. Lett. (2014), vol. 247, pp. 262-267.
Jobbs Dewitt et al., "'Diversomers': An approach to nonpeptide, nonoligomeric chemical diversity," Proc. Natl. Acad. Sci. USA, 1993, 90(15) pp. 6909-6913.
Huang, S. et al., "The apelin-APJ axis: A novel potential therapeutic target for organ fibrosis" Clinica Chimica Acta, 2016, p. 81-88, vol. 456.
Iturnioz, et al., "Identification and pharmacological properties of E339-3D6, the first nonpeptidic apelin receptor agonist," May 2010, The FASEB Journal, vol. 24, pp. 1506-1517.
Khan et al.; "Probe Report" Molecular Libraries, Jul. 2011, pp. 1-22.
Kourtis, et al. "Apelin levels in normal pregnancy" Clinical Endocrinology (2011) 75, pp. 367-371.
Laderias-Lopez et al., "The apelinergic system: the role played in human physiology and pathology and pootential therapeutic applications," Arq Bras Cardiol., 2008, 90(5) pp. 343-349.
Lathen, et al., "ERG-APLNR Axis Controls Pulmonary Venule Endothelial Proliferation in Pulmonary Veno-Occlusive Disease," Circulation, 2014, 130, pp. 1179-1191.
Lee et al., "Characterization of Apelin, the Ligand for the APJ Receptor," Neurochem., 2000, 74(1), pp. 34-41.
Maloney, et al., "Discovery of 4-oxo-6-((pyrimidin-2-ylthio)methyl)-4H-pyran-3-yl-4-nitrobenzoate (ML221) as a functional antagonist of the apelin (APJ) receptor," Bioorganic & Medicinal Chemistry Letters, 2012, 22, pp. 6656-6660.
Martinez, FJ et al. "The Clinical Course of Patients with Idiopathic Pulmonary Fibrosis" Ann Intern Med, 2005, p. 963-967, vol. 142.
Sorli, S. Caroline, et al. "Therapeutic potential of interfering with apelin signalling." Drug discovery today 11.23-24 (2006): 1100-1106.
Fan, Xiao-Fang, et al. "The Apelin-APJ axis is an endogenous counterinjury mechanism in experimental acute lung injury." Chest 147.4 (2015): 969-978.
Extended European Search Report issued in EP Application No. 20858596.8 on Sep. 7, 2023.
Medhurst et al., "Pharmacological and immunohistochemical characterization of the APJ receptor and its endogenous ligand apelin," J. Neurochem., 2003, 84(5) pp. 1162-1172.
Narayanan et al., "Discovery of a novel small molecule agonist scaffold for the APJ receptor," Bioorganic and Medicinal Chemistry, 2016, 24(16) pp. 3758-3770.
O'Donnell et al., "Apelin, an endogenous neuronal peptide, protects hippocampal neurons against excitotoxic injury," J. Neurochem., 2007, 102(6) pp. 1905-1917.
Preissl, S. et al., "Development of an Assay for Complex I/Complex III of the Respiratory Chain Using Solid Supported Membranes and Its Application in Mitochondrial Toxicity Screening in Drug Discovery," Assay and Drug Development Technologies, 2011 vol. 9 pp. 147-156.
Rautio et al., "Prodrugs: design and clinical Applications", Nat Rev Drug Dis, 2008 p. 255-270, vol. 7.
Robinson et al., "Discovery of the Hemifumarate and (r-L-Alanyloxy)methyl Ether as Prodrugs of an Antirheumatic Oxindole: Prodrugs for the Enolic OH Group" J Med Chem, 1996, p. 10-18, vol. 39.
Selman M et al., "Idiopathic Pulmonary Fibrosis: Prevailing and Evolving Hypotheses about Its Pathogenesis and Implications for Therapy", Ami Intern Med, 2001, p. 134-136, vo. 51.
Selman. M., et al., Role of Epithelial Cells in Idiopathic Pulmonary Fibrosis, Am Thorac Soc, 2006, p. 364-372, vol. 4.
Sheikh et al., "In vivo genetic profiling and cellular localization of apelin reveals a hypoxia-sensitive, endothelial-centered pathway activated in ischemic heart failure," Am. J. Physiol. Heart Circ. Physiol., 2008, 294, H88-H98.
Tatemoto et al., "Isolation and Characterization of a Novel Endogenous Peptide Ligand for the Human APJ Receptor," Biochemical and Biophysical Research Communications, 1998, 251, 471-76.
Tatemoto et al., "The novel peptide apelin lowers blood pressure ia a nitric oxide-dependent mechanism," Regulatory Peptides, 2001, 99, pp. 87-92.
Thomas et al., "Identification of 1-({[1-(4-Fluorophenyl)-5-(2-methoxyphenyl)-1H-pyrazol-3-yl]carbonyl}amino) cyclohexane Carboxylic Acid as a Selective Nonpeptide Neurotensin Receptor Type 2 Compound," J. Med. Chem., 2014, vol. 57, pp. 5318-5332.
Tiemann et al., "Increasing myocardial contraction and blood pressure in C57BL/6 mice during early postnatal development," Am. J. Physiol. Heart. Circ. Physiol., 2003, 284, pp. H464-H474.
Wang et al., "Expanding the genetic code for biological studies," Chem Biol., 2009, 16(3) pp. 323-336.
Xie, "A chemical toolkit for proteins—an expanded genetic code," Nat. Rev. Mol. Cell Biol., 2006, 7(10) pp. 775-782.
Zhong et al. "Targeting the apelin pathway asa novel therapeutic approach for cardiovascular diseases," Biochimica et Biophysica Acta, 2017, 1863, 1942-50.
Zou, M.X. et al., "Apelin peptides block the entry of human immunodeficiency virus (HIV)," FEBS Lett., 2000, 473(1) pp. 15-18.
CAS Registry No. 1606440-69-0, 2014.
CAS Registry No. 1584603-48-4, 2014.
CAS Registry No. 1578083-00-7, 2014.
CAS Registry No. 1833984-41-0, 2015.
International Search Report dated Dec. 10, 2020, prepared in International Application No. PCT/US2020/048375.
International Preliminary Report on Patentability dated Mar. 1, 2022 , prepared in International Application No. PCT/US2020/048375.
Ackermann, S, et al. "Endothelialitis, Pulmonary Vascular." Thrombosis, and Angiogenesis in Covid-19/M), N Engl J Med 383 (2020): 2.
Azizi, Yaser, et al. "Post-infarct treatment with [Pyr1] apelin-13 improves myocardial function by increasing neovascularization and overexpression of angiogenic growth factors in rats." European journal of pharmacology 761 (2015): 101-108.
Froldi, Guglielmina, et al., "Endothelial dysfunction in Coronavirus disease 2019 (COVID-19): Gender and age influences." Medical hypotheses 144 (2020): 110015.
Hagihara, Masahiko, et al. "Vinylogous polypeptides: an alternative peptide backbone." Journal of the American Chemical Society 114.16 (1992): 6568-6570.
Hou, Jingying, et al. "Apelin promotes mesenchymal stem cells survival and vascularization under hypoxic-ischemic condition in vitro involving the upregulation of vascular endothelial growth factor." Experimental and Molecular Pathology 102.2 (2017): 203-209.
Ladeiras-Lopes, Ricardo, et al., "The apelinergic system: the role played in human physiology and pathology and potential therapeutic applications." Arquivos brasileiros de cardiologia 90 (2008): 374-380.
Sardu, Celestino, et al. "Hypertension, thrombosis, kidney failure, and diabetes: is COVID-19 an endothelial disease? A comprehensive evaluation of clinical and basic evidence." Journal of clinical medicine 9.5 (2020): 1417.

* cited by examiner

Animal #4 (40X) Heart. Note positive staining in interstitial tissue (black arrows); likely representing endothelial cells.

. Animal #4 (40X) Lung. Note positive staining in alveolar walls (black arrows).

Animal #4 (4x) Liver. Note positive staining of the gallbladder (black arrows). Hepatocytes are unstained.

Animal #4 (40x) Liver. Higher magnification of Figure 3. Note positive staining of the gallbladder lamina propria (black arrows).

Animal #4 (40x) Brain. Positive nuclear staining in a small aggregate of nuclei of cerebrocortical cells of unknown identity (black arrows).

Animal #6 (10x) Brain. Nonspecific staining involving the brain stem (black arrows).

Animal #6 (60x) Heart. Positive staining in interstitial cells (black arrows).

Animal #6 (60x) Heart. Positive staining in nuclei of cardiac myocyte (black arrows).

Lung. Positive staining in endothelial cells lining a medium sized, thin walled blood vessel (likely a vein; black arrows).

Animal #6 (60x). Gallbladder. Note positive staining of the gallbladder lamina propria (black arrows).

Normal

Bleomycin

Test Compound 30 mpk + Bleomycin

Masson's Trichrome

Collagen

Normal

Little to No Fibrosis

Bleomycin

Significant Apoptosis

Test Compound 30mg/kg + Bleomycin

Vastly Reduced Fibrosis

Tunel Stained
▨ Apoptosis

METHODS AND USES FOR APELIN RECEPTOR AGONISTS

CROSS REFERENCE TO RELATED APPLICATION

This application is a National Stage application of International Application No. PCT/US2020/048375 filed Aug. 28, 2020 which claims the benefit of U.S. Provisional Application No. 62/893,661, filed Aug. 29, 2019, each of which are incorporated by reference herein.

FIELD OF THE INVENTION

The present disclosure provides a method for treating idiopathic pulmonary fibrosis in a patient in need thereof comprising administering a therapeutically effective amount of an apelin receptor agonist.

BACKGROUND OF THE INVENTION

Idiopathic Pulmonary Fibrosis ("IPF") is a chronic and progressive lung disease that results in respiratory failure and death. Median survival is about 2 to 4 years from diagnosis. The etiology of IPF remains unknown, but the disease is characterized by fibrotic interstitial infiltrates that are consistent with the histopathologic pattern of usual interstitial pneumonia. Reference is made to Gross T J et al, N Engl J Med (2001), 345:(7}:517-525. As interstitial fibrosis advances with accompanying distortion of lung architecture, the lung becomes less compliant, increasing the effort associated with breathing, leading to dyspnea. Typically, lung function declines slowly over time, but some patients experience rapid declines that can lead to hospitalization or death, particularly in later stages of the disease. Reference is made to Martinez F J et al. Ann Intern Med (2005), 142:963-967.

While the pathogenesis of IPF is not clearly defined, the disease is believed to be caused by repetitive cell injury. See, for example, Selman M et al., Ami Intern Med (2001), 134:136 51; and Selman. M. P c Am Thorac Soc (2006) (4):364-372. According to this hypothesis, initial injuries to the lungs are repaired but continuous injury and loss of basement membrane leads to irreversible loss of epithelial cells and chronic inflammation. Endothelial cells line the small airway capillaries and play an important role in preservation of airway architecture and integrity of basement membrane. Loss of endothelial cells or activation of these cells can lead to exaggerated inflammation and sustained injury to alveolar cells. Chronic cell injury and loss of basement membrane initiate a dysregulated wound healing response characterized by exaggerated deposition of extracellular matrix proteins and replacement of lost parenchymal cells with mesenchymal cells that leads to loss of lung function in susceptible individuals. See, Selman M et. al, (2001) supra; and Selman M. (2006) supra. Agents which may block endothelial cell injury or promote regeneration may present a novel treatment strategy for IPF patients.

The apelin receptor (APJ) was cloned in 1993 as an orphan G-protein coupled receptor (GPCR). The human APJ gene is located on the long arm of chromosome 11 and encodes a 377 amino acid G protein-coupled receptor. The gene for APJ was designated angiotensin-receptor like 1 (AGTRL1) due to sequence similarities between the two receptors. Carpene et al., J Physiol Biochem. 2007; 63(4): 359-373. However, none of the known peptidergic ligands for the angiotensin receptors, including angiotensin, activate APJ. APJ remained an orphan GPCR until 1998 when the peptide apelin was identified as its endogenous ligand. Lee et al., J Neurochem. 2000; 74(1):34-41; Habata et al., Biochim Biophys Acta. 1999; 1452(1):25-35.

Over the years, apelin and APJ have emerged as an important regulator of various physiological processes. Both apelin and APJ are expressed in the central nervous system (CNS) and peripherally in a number of tissues. Expression of APJ has been noted within the vasculature of some organs and is a potent regulator of related processes including angiogenesis and vasoconstriction. Cobellis et al. report increased of expression levels of both apelin and APJ receptor in preeclampsia-complicated pregnancies. Cobellis et al., Histol Histopathol. 2007; 22(1):1-8. APJ is also expressed in nonvascular cell types in heart, liver, and CNS where its primary role is currently under investigation. Medhurst et al., J Neurochem. 2003; 84(5):1162-1172. Apelin and APJ are often co-localized within the same organ suggesting an autocrine regulation of the receptor by its ligand. However, apelin has since been detected in blood suggesting that concomitant paracrine regulation of the receptor is also possible. The apelin-APJ system has been implicated as a regulator of various physiological functions and is believed to play an important role in thermoregulation, immunity, glucose metabolism, angiogenesis, fluid homeostasis, cardiac function, hepatic function and renal function. Ladeiras-Lopes et al., Arq Bras Cardiol. 2008; 90(5):343-349. APJ also acts as a co-receptor during HIV infection. O'Donnell et al., J Neurochem. 2007; 102(6): 1905-1917; Zou et al., FEBS Lett. 2000; 473(1):15-18.

Expression of apelin and APJ are either up- or down-regulated in various pathophysiological conditions. In particular, the APJ appears to be an emerging target for the treatment of cardiovascular failure, liver fibrosis, cancer, angiopathies, pancreatitis, and as a prophylactic against HIV infection. In 2011 Andersen et al. reviewed apelin and APJ as an opportunity for therapeutic uses for pulmonary hypertension and pulmonary arterial hypertension (PAH). Andersen et al. Pulm. Circ. 2011; 1(3) 334-346.

Particular APJ agonists are described in international patent applications PCT/US2015/034427, which published as WO 2015/188073, PCT/US2016/065808, which published as WO 2017/100558, and PCT/US2017/056117, which published as WO 2018/071526. Each of these applications is incorporated herein by reference in their entirety.

SUMMARY OF THE INVENTION

One embodiment of the present disclosure includes a method for treating idiopathic pulmonary fibrosis in a patient in need thereof comprising administering a therapeutically effective amount of an apelin receptor agonist.

One embodiment of the present disclosure includes a method for promoting neovascularization or preservation of capillary architecture through endothelial cell signaling in a patient in need thereof comprising administering a therapeutically effective amount of an apelin receptor agonist. Alternatively, the present disclosure includes a method for preservation of an endothelial cell population in a patient in need thereof comprising administering a therapeutically effective amount of an apelin receptor agonist.

One aspect of an embodiment of the present disclosure includes wherein the apelin receptor agonist is a compound of Formula A:

A

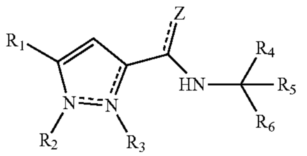

or a pharmaceutically acceptable salt, a prodrug, or a salt of a prodrug, wherein $R_1$ is represented by the formula:

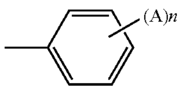

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $—CF_3$, $—(CH_2)_xNR_7R_8$, —CN, $—CONR_7R_8$, $—COR_7$, $—CO_2(CH_2)_xNR_7R_8$, $—CO_2R_7$, halogen, hydroxyl, $—N_3$, $—NHCOR_7$, $—NHSO_2C_{1-8}$ alkyl, $—NHCO_2C_{1-8}$ alkyl, $—NO_2$, $—NR_7R_8$, $—O(CH_2)_xNR_7R_8$, $—O(CH_2)_xCO_2R_7$, $—OCOC_{1-8}$ alkyl, $—OCO(CH_2)_xNR_7R_8$, $—SO_{(1-3)}R_7$, or $—SR_7$;

$R_7$ and $R_8$ are independently alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, $—(CH_2)_xCONHR_9$, $—(CH_2)_xCOR_9$, $—(CH_2)_xCO_2R_9$, H, or heteroaryl; or $R_7$ and $R_8$ together make a 3-8 member ring which may be substituted with one or more heteroatoms;

n is 0, 1, 2, 3, 4 or 5;

each x is independently 0-8;

$R_2$ is present or absent, and if present, is aryl, $C_{1-8}$ alkyl, $C_{1-8}$ alkyl(aryl), $C_{1-8}$ alkyl ($C_{3-8}$ cycloalkyl), $C_{3-8}$ cycloalkyl, or heteroaryl;

$R_3$ is present or absent, is absent if $R_2$ is present, and if present is aryl, $C_{1-8}$ alkyl, $C_{1-8}$ alkyl(aryl), $C_{1-8}$ alkyl ($C_{3-8}$ cycloalkyl), or $C_{3-8}$ cycloalkyl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, $C_{3-8}$ cycloalkyl-$CO_2R_7$, $—(CH_2)_xNR_7R_8$, $—(CH_2)_xOR_7$, $—(CH_2)_xNHCOR_7$, $—(CH_2)_xNHCO_2R_7$, $—(CH_2)_xCONR_7R_8$, $—(CH_2)_xCONR_7(CH_2)_yCO_2R_9$, $—(CH_2)_xCONR_7(CH_2)_yCONR_7R_8$, $—(CH_2)_xCONR_7(CH_2)_yR_9$, $—(CH_2)_xCOR_7$, $—(CH_2)_xCO_2R_7$, $—CHR_7COR_9$, $—CHR_7CONHCHR_8COR_9$, $—CONR_7R_8$, $—CONR_7(CH_2)_xCO_2R_8$, $—CONR_7CHR_8CO_2R_9$, $—CO_2R_9$, H, or $—NHCO_2R_7$; or $R_4$ and $R_5$ together make a 4-8 member ring which may be substituted with one or more heteroatoms or selected from the groups comprising $R_6$;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; each y is independently 1-8;

and Z is $H_2$ or =O.

One aspect of an embodiment of the present disclosure includes wherein the apelin receptor agonist is a compound of Formula B:

B

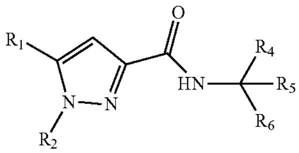

or a pharmaceutically acceptable salt, a prodrug, or a salt of a prodrug, wherein $R_1$ is represented by the formula:

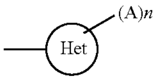

wherein

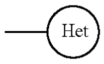

is a monocyclic aryl or heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $—CF_3$, $—(CH_2)_xNR_7R_8$, —CN, $—CONR_7R_8$, $—COR_7$, $—CO_2(CH_2)_xNR_7R_8$, $—CO_2R_7$, halogen, hydroxyl, $—N_3$, $—NHCOR_7$, $—NHSO_2C_{1-8}$ alkyl, $—NHCO_2C_{1-8}$ alkyl, $—NO_2$, $—NR_7R_8$, $—O(CH_2)_xNR_7R_8$, $—O(CH_2)_xCO_2R_7$, $—OCOC_{1-8}$ alkyl, $—OCO(CH_2)_xNR_7R_8$, $—SF_5$, $—SO_2NR_7R_8$, $—SO_{(1-3)}R_7$, $—SR_7$, or tetrazolone;

$R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, $—(CH_2)_xCONHR_9$, $—(CH_2)_xCOR_9$, $—(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups;

n is 1, 2, 3, 4 or 5;

$R_2$ is $C_{3-8}$ alkyl, $C_{1-8}$ alkyl ($C_{3-8}$ cycloalkyl), $C_{3-8}$ cycloalkyl, heteroaryl, or substituted aryl;

$R_4$, $R_5$ and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $—(CH_2)_xNR_7R_8$, $—(CH_2)_xOR_7$, $-(CH_2)_xNR_9COR_7$, $-(CH_2)_xNR_9SO_2R_7$, $-(CH_2)_xNR_9CO_2R_7$, $-(CH_2)_xNHCOR_7$, $-(CH_2)_xNHSO_2R_7$, $-(CH_2)_xNHCO_2R_7$, $-(CH_2)_xCONR_7R_8$, $-(CH_2)_xCONR_7(CH_2)_yCO_2R_9$, $-(CH_2)_xCONR_7(CH_2)_yCONR_7R_8$, $-(CH_2)_xCONR_7(CH_2)_yR_9$, $-(CH_2)_xCOR_7$, $-(CH_2)_xCO_2R_7$, $-(CH_2)_xSO_2NR_7(CH_2)_yR_9$, $-CHR_7COR_9$, $-CHR_7CONHCHR_8COR_9$, $-CONR_7R_8$, $-CONR_7(CH_2)_xCO_2R_8$, $-CONR_7CHR_8CO_2R_9$, $-CO_2R_9$, H, or $-NHCO_2R_7$, $-(CH_2)_xSO_2NR_7R_8$; $-SF_5$; or $R_4$ and $R_5$ together make a 4-8 member ring which may be substituted with one or more heteroatoms; or $R_4$ and $R_5$ together make a 5-8 nitrogen containing member ring with one or more carbonyl groups;

wherein the group $R_4$ is substituted with one or more fluorine atoms;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each x is independently 0-8; and each y is independently 1-8.

One aspect of an embodiment of the present disclosure includes wherein the apelin receptor agonist is a compound of formula C:

C

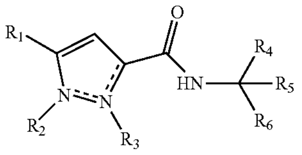

or a pharmaceutically acceptable salt, a prodrug, or a salt of a prodrug, wherein $R_1$ is represented by the formula

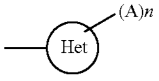

wherein

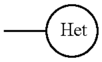

is a monocyclic heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $-CF_3$, $-(CH_2)_xNR_7R_8$, $-CN$, $-CONR_7R_8$, $-COR_7$, $-CO_2(CH_2)_xNR_7R_8$, $-CO_2R_7$, halogen, hydroxyl, $-N_3$, $-NHCOR_7$, $-NHSO_2C_{1-8}$ alkyl, $-NHCO_2C_{1-8}$ alkyl, $-NO_2$, $-NR_7R_8$, $-O(CH_2)_xNR_7R_8$, $-O(CH_2)_xCO_2R_7$, $-OCOC_{1-8}$ alkyl, $-OCO(CH_2)_xNR_7R_8$, $-SF_5$, $-SO_2NR_7R_8$, $-SO_{(1-3)}R_7$, or $-SR_7$;

each $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, $-(CH_2)_xCONHR_9$, $-(CH_2)_xCOR_9$, $-(CH_2)_xCO_2R_9$, H, or heteroaryl; or $R_7$ and $R_8$ together make a 3-9 member cycloalkyl or heterocycloalkyl group;

n is 1, 2, 3, 4 or 5;

each x is independently 0-8;

$R_2$ is present or absent, and if present, is $C_{3-8}$ alkyl, $C_{1-8}$ alkyl ($C_{3-8}$ cycloalkyl), $C_{3-8}$ cycloalkyl, heteroaryl, or substituted aryl;

$R_3$ is present or absent, is absent if $R_2$ is present, and if present is $C_{1-8}$ alkyl, $C_{1-8}$ alkyl ($C_{3-8}$ cycloalkyl), $C_{3-8}$ cycloalkyl or substituted aryl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl $C_6$ heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-9}$ cycloalkyl, $C_{3-8}$ cycloalkyl-$CO_2R_7$, $-(CH_2)_xNR_7R_8$, $-(CH_2)_xOR_7$, $-(CH_2)_xNHCOR_7$, $-(CH_2)_xNHSO_2R_7$, $-(CH_2)_xNHCO_2R_7$, $-(CH_2)_xCONR_7R_8$, $-(CH_2)_xCONR_7(CH_2)_yCO_2R_9$, $-(CH_2)_xCONR_7(CH_2)_yCONR_8R_9$, $-(CH_2)_xCONR_7(CH_2)_yR_9$, $-(CH_2)_xCONR_7(CH_2)_ySO_2R_9$, $-(CH_2)_xCOR_7$, $-(CH_2)_xCO_2R_7$, $-(CH_2)_xSO_2NR_7(CH_2)_yR_9$, $-CHR_7COR_9$, $-CHR_7CONHCHR_8COR_9$, $-CONR_7R_8$, $-CONR_7(CH_2)_xCO_2R_8$, $-CONR_7CHR_8CO_2R_9$, $-CO_2R_9$, H, $-NHCO_2R_7$, $-SF_5$, $-SO_2NR_7R_8$, or $R_4$ and $R_5$ together make a 4-9 member cycloalkyl or heterocycloalkyl group;

wherein the group $R_4$ is substituted with one or more fluorine atoms;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

and each y is independently 1-8.

One aspect of an embodiment of the present disclosure includes wherein the apelin receptor agonist is a compound of formula D:

D

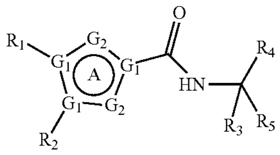

or a pharmaceutically acceptable salt, a prodrug, or a salt of a prodrug, wherein ring A is a 5-member heteroaryl ring; each $G_1$ is independently selected from C or N; each $G_2$ is independently selected from CH or N; the bond between each two instances of $G_1$ or $G_2$ is either a single or a double bond so as to make the ring A an aromatic heterocycle, wherein at least one $G_1$ or $G_2$ is N and a maximum number of three instances of either $G_1$ or $G_2$ in the ring are simultaneously N; provided that if there are two N in ring A and $G_1$ connected to $R_2$ is N, the adjacent $G_2$ is not N;

$R_1$ is represented by the formula:

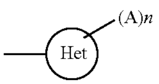

wherein

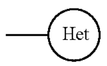

is a monocyclic aryl or heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_2NR_7R_8$, —$SO_{(1-3)}R_7$, or —$SR_7$;

$R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups;

n is 1, 2, 3, 4 or 5;

$R_2$ is optionally substituted $C_{3-8}$ alkyl or optionally substituted $C_{0-8}$ alkyl-$R_{10}$, wherein $R_{10}$ is a 3- to 8-membered ring, optionally containing one or more heteroatom selected from N, O, or S, optionally containing one or more degrees of unsaturation;

$R_3$ is H;

$R_4$ and $R_5$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNR_9COR_7$, —$(CH_2)_xNR_9SO_2R_7$, —$(CH_2)_xNR_9CO_2R_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$(CH_2)_x SO_2NR_7(CH_2)_yR_9$, —$CHR_7COR_9$, —$CHR_7CONHCHR_8COR_9$, —$CONR_7R_8$, —$CONR_7(CH_2)_xCO_2R_8$, —$CONR_7CHR_8CO_2R_9$, —$CO_2R_9$, H, or —$NHCO_2R_7$, —$(CH_2)_x SO_2NR_7R_8$; or $R_4$ and $R_5$ together make a 4-8 member ring which may be substituted with one or more heteroatoms; or $R_4$ and $R_5$ together make a 5-8 nitrogen containing member ring with one or more carbonyl groups;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each x is independently 0-8; and each y is independently 1-8.

One aspect of an embodiment of the present disclosure includes wherein the apelin receptor agonist is a compound of Formula E:

E

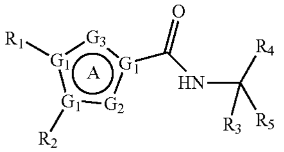

or a pharmaceutically acceptable salt, a prodrug, or a salt of a prodrug, wherein ring A is a 5-member heteroaryl ring; each $G_1$ is independently selected from C or N; each $G_2$ or $G_3$ is independently selected from CH, N, O or S;

wherein at least one $G_2$ or $G_3$ is O or S;

if $G_2$ is O or S then, $G_3$ is CH or N; if $G_3$ is O or S then, $G_2$ is CH or N;

the bond between each two instances of $G_1$, $G_2$ or $G_3$ is either a single or a double bond so as to make the ring A an aromatic heterocycle, and a maximum number of two instances of either $G_1$ $G_2$ or $G_3$ in the ring are simultaneously N;

$R_1$ is represented by the formula:

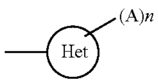

wherein

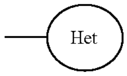

is a monocyclic aryl or heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_2NR_7R_8$, —$SO_{(1-3)}R_7$, or —$SR_7$;

$R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups;

n is 1, 2, 3, 4 or 5;

$R_2$ is optionally substituted $C_{3-8}$ alkyl or optionally substituted $C_{0-8}$ alkyl-$R_{10}$, wherein $R_{10}$ is a 3- to 8-membered ring, optionally containing one or more heteroatom selected from N, O, or S, optionally containing one or more degrees of unsaturation;

$R_3$ is H;

$R_4$ and $R_5$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $—(CH_2)_xNR_7R_8$, $—(CH_2)_xOR_7$, $—(CH_2)_xNR_9COR_7$, $—(CH_2)_xNR_9SO_2R_7$, $—(CH_2)_xNR_9CO_2R_7$, $—(CH_2)_xNHCOR_7$, $—(CH_2)_xNHSO_2R_7$, $—(CH_2)_xNHCO_2R_7$, $—(CH_2)_xCONR_7R_8$, $—(CH_2)_xCONR_7(CH_2)_yCO_2R_9$, $—(CH_2)_xCONR_7(CH_2)_yCONR_7R_8$, $—(CH_2)_xCONR_7(CH_2)_yR_9$, $—(CH_2)_xCOR_7$, $—(CH_2)_xCO_2R_7$, $—(CH_2)_xSO_2NR_7(CH_2)_yR_9$, $—CHR_7COR_9$, $—CHR_7CONHCHR_8COR_9$, $—CONR_7R_8$, $—CONR_7(CH_2)_xCO_2R_8$, $—CONR_7CHR_8CO_2R_9$, $—CO_2R_9$, H, or $—NHCO_2R_7$, $—(CH_2)_x SO_2NR_7R_8$; or $R_4$ and $R_5$ together make a 4-8 member ring which may be substituted with one or more heteroatoms; or $R_4$ and $R_5$ together make a 5-8 nitrogen containing member ring with one or more carbonyl groups;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each x is independently 0-8; and each y is independently 1-8.

One aspect of an embodiment of the present disclosure includes wherein the apelin receptor agonist is Compound 1, which is (3S)-3-({1-cyclopentyl-5-[2-(trifluoromethyl)phenyl]-1H-pyrazol-3-yl}formamido)-5-(3,3-difluoropiperidin-1-yl)pentanoic acid.

One aspect of an embodiment of the present disclosure includes wherein the apelin receptor agonist is selected from:

(2S)-2-{[5-(2,6-dimethoxyphenyl)-1-(4-fluorophenyl)-1H-pyrazol-3-yl]formamido}-4-methylpentanoic acid;

(3S)-3-{[5-(2,6-dimethoxyphenyl)-1-(4-fluorophenyl)-1H-pyrazol-3-yl]formamido}-5-methylhexanoic acid;

(3S)-3-{[5-(2,6-dimethoxyphenyl)-1-(4-fluorophenyl)-1H-pyrazol-3-yl]formamido}-5-methylhexanamide;

(3R)-3-{[5-(2,6-dimethoxyphenyl)-1-(4-fluorophenyl)-1H-pyrazol-3-yl]formamido}-5-methylhexanoic acid;

2-(2-cyclohexyl-2-{[5-(2,6-dimethoxyphenyl)-1-(4-fluorophenyl)-1H-pyrazol-3-yl]formamido}acetamido)acetic acid;

(2S)-2-cyclohexyl-2-{[5-(2,6-dimethoxyphenyl)-1-(4-fluorophenyl)-1H-pyrazol-3-yl]formamido}acetic acid;

2-[(3S)-3-{[5-(2,6-dimethoxyphenyl)-1-(4-fluorophenyl)-1H-pyrazol-3-yl]formamido}-5-methylhexanamido]acetic acid;

(3S)-3-{[1-cyclohexyl-5-(2,6-dimethoxyphenyl)-1H-pyrazol-3-yl]formamido}-5-methylhexanoic acid;

2-[(3S)-3-{[1-cyclohexyl-5-(2,6-dimethoxyphenyl)-1H-pyrazol-3-yl]formamido}-5-methylhexanamido]acetic acid;

(3S)-3-({5-[2-(benzyloxy)-6-methoxyphenyl]-1-(4-fluorophenyl)-1H-pyrazol-3-yl}formamido)-5-methylhexanoic acid;

(3S)-3-{[1-(4-fluorophenyl)-5-[2-methoxy-6-(2-methoxy-2-oxoethoxy)phenyl]-1H-pyrazol-3-yl]formamido}-5-methylhexanoic acid;

2-cyclohexyl-2-{[1-cyclohexyl-5-(2,6-dimethoxyphenyl)-1H-pyrazol-3-yl]formamido}acetic acid;

(3S)-3-{[1-(cyclohexylmethyl)-5-(2,6-dimethoxyphenyl)-1H-pyrazol-3-yl]formamido}-5-methylhexanoic acid;

methyl 2-[(3S)-3-{[1-cyclohexyl-5-(2,6-dimethoxyphenyl)-1H-pyrazol-3-yl]formamido}-5-methylhexanamido]acetate;

(3S)-3-{[5-(2,6-dimethoxyphenyl)-1-(2-methylpropyl)-1H-pyrazol-3-yl]formamido}-5-methylhexanoic acid;

(3S)-3-({5-[2-(benzyloxy)-6-methoxyphenyl]-1-cyclohexyl-1H-pyrazol-3-yl}formamido)-5-methylhexanoic acid methyl 2-[(3S)-3-({5-[2-(benzyloxy)-6-methoxyphenyl]-1-cyclohexyl-1H-pyrazol-3-yl}formamido)-5-methylhexanamido]acetate 2-[(3S)-3-({5-[2-(benzyloxy)-6-methoxyphenyl]-1-cyclohexyl-1H-pyrazol-3-yl}formamido)-5-methylhexanamido]acetic acid methyl 2-[(3S)-3-{[5-(2,6-dimethoxyphenyl)-1-(2-methylpropyl)-1H-pyrazol-3-yl]formamido}-5-methylhexanamido]acetate (3S)—N-benzyl-3-({5-[2-(benzyloxy)-6-methoxyphenyl]-1-cyclohexyl-1H-pyrazol-3-yl}formamido)-5-methylhexanamide (3S)-3-({5-[2-(benzyloxy)-6-methoxyphenyl]-1-cyclohexyl-1H-pyrazol-3-yl}formamido)-N-butyl-5-methylhexanamide (3S)-3-({5-[2-(benzyloxy)-6-methoxyphenyl]-1-cyclohexyl-1H-pyrazol-3-yl}formamido)-5-methyl-N-(1,3-oxazol-2-ylmethyl)hexanamide (3S)-3-({5-[2-(benzyloxy)-6-methoxyphenyl]-1-cyclohexyl-1H-pyrazol-3-yl}formamido)-N-[(dimethylcarbamoyl)methyl]-5-methylhexanamide methyl 2-[(3S)-3-{[5-(2,6-dimethoxyphenyl)-1-(4-fluorophenyl)-1H-pyrazol-3-yl]formamido}-5-methylhexanamido]acetate ethyl 3-[(3S)-3-({5-[2-(benzyloxy)-6-methoxyphenyl]-1-cyclohexyl-1H-pyrazol-3-yl}formamido)-5-methylhexanamido]propanoate (3S)-3-{[5-(2,6-dimethoxyphenyl)-1-(2-methylpropyl)-1H-pyrazol-3-yl]formamido}-5-methyl-N-(1,3-oxazol-2-ylmethyl)hexanamide (3S)-3-{[5-(2,6-dimethoxyphenyl)-1-(2-methylpropyl)-1H-pyrazol-3-yl]formamido}-N,5-dimethylhexanamide (3S)-3-{[5-(2,6-dimethoxyphenyl)-1-(2-methylpropyl)-1H-pyrazol-3-yl]formamido}-N-(2-hydroxyethyl)-5-methylhexanamide (3S)—N-butyl-3-{[5-(2,6-dimethoxyphenyl)-1-(2-methylpropyl)-1H-pyrazol-3-yl]formamido}-5-methylhexanamide (3R)—N-butyl-3-{[5-(2,6-dimethoxyphenyl)-1-(2-methylpropyl)-1H-pyrazol-3-yl]formamido}-5-methylhexanamide (3S)-3-{[5-(2,6-dimethoxyphenyl)-1-(2-methylpropyl)-1H-pyrazol-3-yl]formamido}-N-hexyl-5-methylhexanamide (3S)—N-(cyclohexylmethyl)-3-{[5-(2,6-dimethoxyphenyl)-1-(2-methylpropyl)-1H-pyrazol-3-yl]formamido}-5-methylhexanamide (3S)-3-{[5-(2,6-dimethoxyphenyl)-1-(2-methylpropyl)-1H-pyrazol-3-yl]formamido}-5-methyl-N-pentylhexanamide (3S)-3-{[5-(2,6-dimethoxyphenyl)-1-(2-methylpropyl)-1H-pyrazol-3-yl]formamido}-5-methyl-N-propylhexanamide (3S)-3-{[5-(2,6-dimethoxyphenyl)-1-(2-methylpropyl)-1H-pyrazol-3-yl]formamido}-N-ethyl-5-methylhexanamide (3S)-3-{[5-(2,6-dimethoxyphenyl)-1-(2-methylpropyl)-1H-pyrazol-3-yl]formamido}-5-methyl-N-(propan-2-yl)hexanamide (3S)-3-{[5-(2,6-dimethoxyphenyl)-1-(2-methylpropyl)-1H-pyrazol-3-yl]formamido}-N-(4-fluorophenyl)-5-methylhexanamide methyl (3S)-3-{[5-(2,6-dimethoxyphenyl)-1-(2-methylpropyl)-1H-pyrazol-3-yl]formamido}-5-methylhexanoate (3S)-3-{[5-(3,5-difluoro-2,6-dimethoxyphenyl)-1-(2-methylpropyl)-1H-pyrazol-3-yl]formamido}-5-methylhexanoic acid (3S)—N-butyl-3-{[5-(3,5-difluoro-2,6-dimethoxyphenyl)-1-(2-methylpropyl)-1H-pyrazol-3-yl]formamido}-5-methylhexanamide (2S)-2-cyclohexyl-2-{[5-(2,6-dimethoxyphenyl)-1-(2-methylpropyl)-1H-pyrazol-3-yl]formamido}acetic acid (3S)-3-{[5-(2,6-dimethoxyphenyl)-1-(2-methylpropyl)-1H-pyrazol-3-yl]formamido}-N,5-dimethyl-N-propylhexanamide (3S)—N-cyclopropyl-3-{[5-(2,6-dimethoxyphenyl)-1-(2-methylpropyl)-1H-pyrazol-3-yl]formamido}-5-methylhexanamide (3S)—N-cyclobutyl-3-{[5-(2,6-dimethoxyphenyl)-1-(2-methylpropyl)-1H-pyrazol-3-yl]formamido}-5-methylhexanamide 2-[(3S)-3-{[5-(2,6-dimethoxyphenyl)-1-(2-methylpropyl)-1H-pyrazol-3-yl]formamido}-5-methylhexanamido]acetic acid (3S)—N-(carbamoylmethyl)-3-{[5-(2,6-dimethoxyphenyl)-1-(2-methylpropyl)-1H-pyrazol-3-yl]formamido}-5-methylhexanamide (3S)-3-{[5-(2,6-dimethoxyphenyl)-1-(2-methylpropyl)-1H-pyrazol-3-yl]formamido}-5-methyl-N-[(methylcarbamoyl)methyl]hexanamide (3S)-3-{[1-(cyclopropylmethyl)-5-(2,6-dimethoxyphenyl)-1H-pyrazol-3-yl]formamido}-5-methylhexanoic acid (3S)-3-{[1-cyclopentyl-5-(2,6-dimethoxyphenyl)-1H-pyrazol-3-yl]formamido}-5-methylhexanoic acid methyl 2-[(3S)-3-{[1-(cyclopropylmethyl)-5-(2,6-dimethoxyphenyl)-1H-pyrazol-3-yl]formamido}-5-methylhexanamido]acetate methyl 2-1[(3S)-3-{[1-cyclopentyl-5-(2,6-dimethoxyphenyl)-1H-pyrazol-3-yl]formamido}-5-methylhexanamido]acetate (3S)—N-cyclopentyl-3-{[5-(2,6-dimethoxyphenyl)-1-(2-methylpropyl)-1H-pyrazol-3-yl]formamido}-5-methylhexanamide methyl 2-[(3S)-3-{[5-(2,6-dimethoxyphenyl)-1-propyl-1H-pyrazol-3-yl]formamido}-5-methylhexanamido]acetate methyl 2-[(3S)-3-{[5-(2,6-dimethoxyphenyl)-1-(2,2-dimethylpropyl)-1H-pyrazol-3-yl]formamido}-5-methylhexanamido]acetate methyl 2-[(2S)-2-{[5-(2,6-dimethoxyphenyl)-1-(2-methylpropyl)-1H-pyrazol-3-yl]formamido}-4-methylpentanamido]acetate methyl 2-[(2S)-2-{[1-cyclohexyl-5-(2,6-dimethoxyphenyl)-1H-pyrazol-3-yl]formamido}-4-methylpentanamido]acetate ethyl 3-[(2S)-2-{[5-(2,6-dimethoxyphenyl)-1-(2-methylpropyl)-1H-pyrazol-3-yl]formamido}-4-methylpentanamido]propanoate methyl 2-[(2S)-3-cyclohexyl-2-{[5-(2,6-dimethoxyphenyl)-1-(2-methylpropyl)-1H-pyrazol-3-yl]formamido}propanamido]acetate (2S)-3-cyclohexyl-2-{[5-(2,6-dimethoxyphenyl)-1-(2-methylpropyl)-1H-pyrazol-3-yl]formamido}propanoic acid methyl 2-[(2S)-2-{[5-(2,6-dimethoxyphenyl)-1-(2-methylpropyl)-1H-pyrazol-3-yl]formamido}-3-phenylpropanamido]acetate methyl 2-[(2S)-2-{[5-(2,6-dimethoxyphenyl)-1-(2-methylpropyl)-1H-pyrazol-3-yl]formamido}hexanamido]acetate methyl 2-[(2S)-2-{[5-(2,6-dimethoxyphenyl)-1-(2-methylpropyl)-1H-pyrazol-3-yl]formamido}-4-phenylbutanamido]acetate (3S)-5-cyclohexyl-3-{[5-(2,6-dimethoxyphenyl)-1-(2-methylpropyl)-1H-pyrazol-3-yl]formamido}pentanoic acid methyl 2-[(3S)-5-cyclohexyl-3-{[5-(2,6-dimethoxyphenyl)-1-(2-methylpropyl)-1H-pyrazol-3-yl]formamido}pentanamido]acetate methyl 2-[(2S)-3-cyclohexyl-2-{[5-(2,5-dimethoxyphenyl)-1-(2-methylpropyl)-1H-pyrazol-3-yl]formamido}propanamido]acetate methyl 2-[(3S)-3-{[5-(2,6-dimethoxyphenyl)-1-(2-methylpropyl)-1H-pyrazol-3-yl]formamido}-N,5-dimethylhexanamido]acetate methyl 2-[(2S)-2-{[5-(2,6-dimethoxyphenyl)-1-(2-methylpropyl)-1H-pyrazol-3-yl]formamido}-N,4-dimethylpentanamido]acetate 2-[(3S)-5-cyclohexyl-3-{[5-(2,6-dimethoxyphenyl)-1-(2-methylpropyl)-1H-pyrazol-3-yl]formamido}pentanamido]acetic acid (2S)-2-{[5-(2,6-dimethoxyphenyl)-1-(2-methylpropyl)-1H-pyrazol-3-yl]formamido}-4-phenyl-N-propylbutanamide 5-(2,6-dimethoxyphenyl)-1-(2-methylpropyl)-N-[(2S)-1-oxo-4-phenyl-1-(pyrrolidin-1-yl)butan-2-yl]-1H-pyrazole-3-carboxamide methyl 2-[(2S)-2-{[5-(2,6-dimethoxyphenyl)-1-(2-methylpropyl)-1H-pyrazol-3-yl]formamido}-N-methyl-4-phenylbutanamido]acetate (2S)-2-{[5-(2,6-dimethoxyphenyl)-1-(2-methylpropyl)-1H-pyrazol-3-yl]formamido}-N-(2-methoxyethyl)-4-phenylbutanamide (3S)—N-cyclobutyl-5-cyclohexyl-3-{[5-(2,6-dimethoxyphenyl)-1-(2-methylpropyl)-1H-pyrazol-3-yl]formamido}pentanamide (3S)-5-cyclohexyl-3-{[5-(2,6-dimethoxyphenyl)-1-(2-methylpropyl)-1H-pyrazol-3-yl]formamido}pentanamide (3S)-5-cyclohexyl-3-{[5-(2,6-dimethoxyphenyl)-1-(2-methylpropyl)-1H-pyrazol-3-yl]formamido}-N-(2-hydroxybutyl)pentanamide (2S)-2-{[5-(2,6-dimethoxyphenyl)-1-(2-methylpropyl)-1H-pyrazol-3-yl]formamido}-N-(2-hydroxybutyl)-4-phenylbutanamide (2S)-2-{[5-(2,6-dimethoxyphenyl)-1-(2-methylpropyl)-1H-pyrazol-3-yl]formamido}-N-(2-oxobutyl)-4-phenylbutanamide (3S)-5-cyclohexyl-3-{[5-(2,6-dimethoxyphenyl)-1-(2-methylpropyl)-1H-pyrazol-3-yl]formamido}-N-(2-oxobutyl)pentanamide methyl 2-[(3S)-3-{1-[5-(2,6-dimethoxyphenyl)-1-(2-methylpropyl)-1H-pyrazol-3-yl]-N-methylformamido}-5-methylhexanamido]acetate (3S)-5-cyclohexyl-3-{[5-(2,6-dimethoxyphenyl)-1-(2-methylpropyl)-1H-pyrazol-3-yl]formamido}-N-(2-methoxyethyl)pentanamide methyl 2-[(3S)-5-cyclohexyl-3-{[5-(2,6-dimethoxyphenyl)-1-(2-methylpropyl)-1H-pyrazol-3-yl]formamido}-N-methylpentanamido]acetate (2S)—N-cyclobutyl-2-{[5-(2,6-dimethoxyphenyl)-1-(2-methylpropyl)-1H-pyrazol-3-yl]formamido}-4-phenylbutanamide methyl 2-[(3S)-6-cyclohexyl-3-{[5-(2,6-dimethoxyphenyl)-1-(2-methylpropyl)-1H-pyrazol-3-yl]formamido}hexanamido]acetate (3S)-3-{[5-(2,6-dimethoxyphenyl)-1-(2-methylpropyl)-1H-pyrazol-3-yl]formamido}-N-(2-hydroxybutyl)-5-(piperidin-1-yl)pentanamide (3S)—N-cyclobutyl-3-{[5-(2,6-dimethoxyphenyl)-1-(2-methylpropyl)-1H-pyrazol-3-yl]formamido}-5-(piperidin-1-yl)pentanamide (3S)-3-{[5-(2,6-dimethoxyphenyl)-1-(2-methylpropyl)-1H-pyrazol-3-yl]formamido}-N-(2-methoxyethyl)-5-(piperidin-1-yl)pentanamide
(3S)-3-{[5-(2,6-dimethoxyphenyl)-1-(2-methylpropyl)-1H-pyrazol-3-yl]formamido}-5-(piperidin-1-yl)pentanoic acid
(3S)-3-{[1-cyclopentyl-5-(2,6-dimethoxyphenyl)-1H-pyrazol-3-yl]formamido}-5-(piperidin-1-yl)pentanoic acid
(3S)—N-cyclobutyl-3-{[1-cyclopentyl-5-(2,6-dimethoxyphenyl)-1H-pyrazol-3-yl]formamido}-5-(piperidin-1-yl)pentanamide
(2S)-4-cyclohexyl-2-{[5-(2,6-dimethoxyphenyl)-1-(2-methylpropyl)-1H-pyrazol-3-yl]formamido}-N-(2-methoxyethyl)-N-methylbutanamide
(3R)-3-cyclohexyl-3-{[5-(2,6-dimethoxyphenyl)-1-(4-fluorophenyl)-1H-pyrazol-3-yl]formamido}propanoic acid
methyl 2-(3-cyclohexyl-3-{[5-(2,6-dimethoxyphenyl)-1-(4-fluorophenyl)-1H-pyrazol-3-yl]formamido}propanamido)acetate
(3S)-5-cyclohexyl-3-{[5-(2,6-dimethoxyphenyl)-1-(2-methylpropyl)-1H-pyrazol-3-yl]formamido}-N-[(2R)-2-hydroxybutyl]pentanamide
(3R)—N-cyclobutyl-3-{[1-cyclopentyl-5-(2,6-dimethoxyphenyl)-1H-pyrazol-3-yl]formamido}pent-4-enamide;
N-[(2S)-4-cyclohexyl-1-(1H-1,2,3,4-tetrazol-5-yl)butan-2-yl]-5-(2,6-dimethoxyphenyl)-1-(2-methylpropyl)-1H-pyrazole-3-carboxamide;
(3S)—N-cyclobutyl-3-{[1-cyclopentyl-5-(2,6-dimethoxyphenyl)-1H-pyrazol-3-yl]formamido}-5-(piperidin-1-yl)pentanamide;
(3S)—N-cyclobutyl-3-{[5-(2,6-dimethoxyphenyl)-1-(2-methylpropyl)-1H-pyrazol-3-yl]formamido}-5-phenylpentanamide;
(3S)-3-{[5-(2,6-dimethoxyphenyl)-1-(2-methylpropyl)-1H-pyrazol-3-yl]formamido}-4-phenylbutanoic acid;
(3S)-5-cyclohexyl-3-{[5-(2,6-dimethoxyphenyl)-1-(4-fluorophenyl)-1H-pyrazol-3-yl]formamido}pentanoic acid;
(3S)-3-{[5-(2,6-dimethoxyphenyl)-1-(4-fluorophenyl)-1H-pyrazol-3-yl]formamido}-5-phenylpentanoic acid;
(3R)-3-{[5-(2,6-dimethoxyphenyl)-1-(2-methylpropyl)-1H-pyrazol-3-yl]formamido}-3-phenylpropanoic acid;
(3S)-6-cyclohexyl-3-{[5-(2,6-dimethoxyphenyl)-1-(2-methylpropyl)-1H-pyrazol-3-yl]formamido}hexanoic acid
(2S)—N-cyclobutyl-2-{[5-(2,6-dimethoxyphenyl)-1-(2-methylpropyl)-1H-pyrazol-3-yl]formamido}-3-phenylpropanamide
tert-butyl (3S)-3-{[1-cyclopentyl-5-(2,6-dimethoxyphenyl)-1H-pyrazol-3-yl]formamido}-5-(morpholin-4-yl)pentanoate
tert-butyl (3S)-3-{[1-cyclopentyl-5-(2,6-dimethoxyphenyl)-1H-pyrazol-3-yl]formamido}-5-(4-methylpiperazin-1-yl)pentanoate
tert-butyl (3S)-3-{[1-cyclopentyl-5-(2,6-dimethoxyphenyl)-1H-pyrazol-3-yl]formamido}-5-(diethylamino)pentanoate
tert-butyl (3S)-3-{[1-cyclopentyl-5-(2,6-dimethoxyphenyl)-1H-pyrazol-3-yl]formamido}-5-[(pyridin-4-ylmethyl)amino]pentanoate
(3S)-3-{[1-cyclopentyl-5-(2,6-dimethoxyphenyl)-1H-pyrazol-3-yl]formamido}-5-(morpholin-4-yl)pentanoic acid
(3S)-3-{[1-cyclopentyl-5-(2,6-dimethoxyphenyl)-1H-pyrazol-3-yl]formamido}-5-(4-methylpiperazin-1-yl)pentanoic acid
(3S)-3-{[1-cyclopentyl-5-(2,6-dimethoxyphenyl)-1H-pyrazol-3-yl]formamido}-5-(diethylamino)pentanoic acid
(3S)-3-{[1-cyclopentyl-5-(2,6-dimethoxyphenyl)-1H-pyrazol-3-yl]formamido}-5-[(pyridin-4-ylmethyl)amino]pentanoic acid
(2S)-2-{[5-(2,6-dimethoxyphenyl)-1-(2-methylpropyl)-1H-pyrazol-3-yl]formamido}-4-phenylbutanoic acid
(3S)—N-cyclobutyl-3-{[1-cyclopentyl-5-(2,6-dimethoxyphenyl)-1H-pyrazol-3-yl]formamido}-5-(morpholin-4-yl)pentanamide
(3S)—N-cyclobutyl-3-{[1-cyclopentyl-5-(2,6-dimethoxyphenyl)-1H-pyrazol-3-yl]formamido}-5-(4-methylpiperazin-1-yl)pentanamide
(3S)—N-cyclobutyl-3-{[1-cyclopentyl-5-(2,6-dimethoxyphenyl)-1H-pyrazol-3-yl]formamido}-5-(diethylamino)pentanamide
1-cyclopentyl-5-(2,6-dimethoxyphenyl)-N-[(4S)-2-oxo-1-(pyridin-4-ylmethyl)piperidin-4-yl]-1H-pyrazole-3-carboxamide
tert-butyl (3S)-3-{[1-cyclopentyl-5-(2,6-dimethoxyphenyl)-1H-pyrazol-3-yl]formamido}-5-(pyrrolidin-1-yl)pentanoate
(3S)-3-{[1-cyclopentyl-5-(2,6-dimethoxyphenyl)-1H-pyrazol-3-yl]formamido}-5-(pyrrolidin-1-yl)pentanoic acid hydrochloride
(3S)—N-cyclobutyl-3-{[1-cyclopentyl-5-(2,6-dimethoxyphenyl)-1H-pyrazol-3-yl]formamido}-5-(pyrrolidin-1-yl)pentanamide
tert-butyl (3S)-5-(azepan-1-yl)-3-{[1-cyclopentyl-5-(2,6-dimethoxyphenyl)-1H-pyrazol-3-yl]formamido}pentanoate
tert-butyl (3S)-5-{7-azabicyclo[2.2.1]heptan-7-yl}-3-{[1-cyclopentyl-5-(2,6-dimethoxyphenyl)-1H-pyrazol-3-yl]formamido}pentanoate
(3S)—N-cyclobutyl-3-{[5-(2,6-dimethoxyphenyl)-1-(2-methylpropyl)-1H-pyrazol-3-yl]formamido}-4-phenylbutanamide
(3S)-5-(azepan-1-yl)-3-{[1-cyclopentyl-5-(2,6-dimethoxyphenyl)-1H-pyrazol-3-yl]formamido}pentanoic acid
(3S)-5-{7-azabicyclo[2.2.1]heptan-7-yl}-3-{[1-cyclopentyl-5-(2,6-dimethoxyphenyl)-1H-pyrazol-3-yl]formamido}pentanoic acid
(3S)-5-(azepan-1-yl)-N-cyclobutyl-3-{[1-cyclopentyl-5-(2,6-dimethoxyphenyl)-1H-pyrazol-3-yl]formamido}pentanamide
(3S)-5-{7-azabicyclo[2.2.1]heptan-7-yl}-N-cyclobutyl-3-{[1-cyclopentyl-5-(2,6-dimethoxyphenyl)-1H-pyrazol-3-yl]formamido}pentanamide
(3S)-3-{[1-cyclopentyl-5-(2,6-dimethoxyphenyl)-1H-pyrazol-3-yl]formamido}-N-(1-methylcyclobutyl)-5-(piperidin-1-yl)pentanamide
(3S)-3-{[1-cyclopentyl-5-(2,6-dimethoxyphenyl)-1H-pyrazol-3-yl]formamido}-N-(3-methyloxetan-3-yl)-5-(piperidin-1-yl)pentanamide
(3S)-3-{[1-cyclopentyl-5-(2,6-dimethoxyphenyl)-1H-pyrazol-3-yl]formamido}-N-(1-methylcyclopropyl)-5-(piperidin-1-yl)pentanamide
(3S)—N-cyclobutyl-3-{[1-cyclopentyl-5-(2,6-dimethoxyphenyl)-1H-pyrazol-3-yl]formamido}-5-(2,6-dimethylpiperidin-1-yl)pentanamide
(3S)-3-{[1-cyclopentyl-5-(2,6-dimethoxyphenyl)-1H-pyrazol-3-yl]formamido}-5-(2,6-dimethylpiperidin-1-yl)pentanoic acid
(3S)—N-cyclobutyl-3-{[1-cyclopentyl-5-(2,6-dimethoxyphenyl)-1H-pyrazol-3-yl]formamido}-N-methyl-5-(piperidin-1-yl)pentanamide
(3S)-3-{[1-cyclopentyl-5-(2,6-dimethoxyphenyl)-1H-pyrazol-3-yl]formamido}-N-(oxan-4-yl)-5-(piperidin-1-yl)pentanamide (3S)—N-tert-butyl-3-{[1-cyclopentyl-5-(2,6-dimethoxyphenyl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-N-(2-methoxyethyl)-N-methyl-5-(piperidin-1-yl)pentanamide (3S)—N-cyclobutyl-3-{[1-cyclopentyl-5-(2,6-dimethoxyphenyl)-1H-pyrazol-3-yl]formamido}-5-(4,4-difluoropiperidin-1-yl)pentanamide (3S)-3-{[1-cyclopentyl-5-(2,6-dimethoxyphenyl)-1H-pyrazol-3-yl]formamido}-N-(2-methoxyethyl)-5-(piperidin-1-yl)pentanamide 1-cyclopentyl-5-(2,6-dimethoxyphenyl)-N-[(3S)-1-{2-oxa-6-azaspiro[3.3]heptan-6-yl}-1-oxo-5-(piperidin-1-yl)pentan-3-yl]-1H-pyrazole-3-carboxamide (3S)-3-{[1-cyclopentyl-5-(2,6-dimethoxyphenyl)-1H-pyrazol-3-yl]formamido}-5-(piperidin-1-yl)-N-(1,3-thiazol-2-yl)pentanamide (3S)-3-{[1-cyclopentyl-5-(2,6-dimethoxyphenyl)-1H-pyrazol-3-yl]formamido}-N-(1,3-oxazol-2-yl)-5-(piperidin-1-yl)pentanamide (3S)-3-{[1-cyclopentyl-5-(2,6-dimethoxyphenyl)-1H-pyrazol-3-yl]formamido}-N-(1,3-oxazol-2-ylmethyl)-5-(piperidin-1-yl)pentanamide cyclobutyl(3S)-3-{[1-cyclopentyl-5-(2,6-dimethoxyphenyl)-1H-pyrazol-3-yl]formamido}-5-(piperidin-1-yl)pentanoate (3S)-3-(1-{5-[2,6-bis(2,2,2-trifluoroethoxy)phenyl]-1-cyclopentyl-1H-pyrazol-3-yl}-N-ethylformamido)-N-cyclobutyl-5-(piperidin-1-yl)pentanamide 1-cyclopentyl-5-(2,6-dimethoxyphenyl)-N-[(2S)-1-(5-methyl-1,3,4-oxadiazol-2-yl)-4-(piperidin-1-yl)butan-2-yl]-1H-pyrazole-3-carboxamide (3S)—N-cyclobutyl-3-(1-{1-cyclopentyl-5-[2-(trifluoromethoxy)phenyl]-1H-pyrazol-3-yl}-N-ethylformamido)-5-(piperidin-1-yl)pentanamide (3S)—N-cyclobutyl-3-{1-[1-cyclopentyl-5-(2-fluoro-6-methoxyphenyl)-1H-pyrazol-3-yl]-N-ethylformamido}-5-(piperidin-1-yl)pentanamide (3S)—N-cyclobutyl-3-{1-[5-(2,6-dimethoxyphenyl)-1-(pentan-3-yl)-1H-pyrazol-3-yl]-N-ethylformamido}-5-(piperidin-1-yl)pentanamide (3S)—N-cyclobutyl-3-{1-[1-cyclopentyl-5-(thiophen-2-yl)-1H-pyrazol-3-yl]-N-ethylformamido}-5-(piperidin-1-yl)pentanamide (3S)—N-cyclobutyl-3-{[1-cyclopentyl-5-(2,6-dimethoxyphenyl)-1H-pyrazol-3-yl]formamido}-5-(3,3-difluoropiperidin-1-yl)pentanamide (3S)-5-{2-azaspiro[3.3]heptan-2-yl}-N-cyclobutyl-3-{[1-cyclopentyl-5-(2,6-dimethoxyphenyl)-1H-pyrazol-3-yl]formamido}pentanamide (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-yl)pentanamide (3S)-3-{[1-cyclopentyl-5-(2,6-dimethoxyphenyl)-1H-pyrazol-3-yl]formamido}-N-methyl-5-(piperidin-1-yl)-N-(1,3-thiazol-2-yl)pentanamide (3S)-3-{[1-cyclopentyl-5-(2,6-dimethoxyphenyl)-1H-pyrazol-3-yl]formamido}-5-(piperidin-1-yl)pentanamide (3S)-3-({5-[2,6-bis(2,2,2-trifluoroethoxy)phenyl]-1-cyclopentyl-1H-pyrazol-3-yl}formamido)-N-cyclobutyl-5-(piperidin-1-yl)pentanamide (3S)—N-cyclobutyl-3-{[1-cyclopentyl-5-(2,4,6-trifluorophenyl)-1H-pyrazol-3-yl]formamido}-5-(piperidin-1-yl)pentanamide (3S)—N-cyclobutyl-3-{[1-cyclopentyl-5-(4-ethoxy-2,6-difluorophenyl)-1H-pyrazol-3-yl]formamido}-5-(piperidin-1-yl)pentanamide (3S)—N-cyclobutyl-3-{[5-(2,6-dimethoxyphenyl)-1-(2-methylcyclohexyl)-1H-pyrazol-3-yl]formamido}-5-(piperidin-1-yl)pentanamide (3S)—N-cyclobutyl-3-{[5-(2,6-dimethoxyphenyl)-1-(pentan-3-yl)-1H-pyrazol-3-yl]formamido}-5-(piperidin-1-yl)pentanamide 1-cyclopentyl-5-(2,6-dimethoxyphenyl)-N-[(3S)-1-hydroxy-5-(piperidin-1-yl)pentan-3-yl]-1H-pyrazole-3-carboxamide (3S)—N-cyclobutyl-3-({1-cyclopentyl-5-[2-(trifluoromethoxy)phenyl]-1H-pyrazol-3-yl}formamido)-5-(piperidin-1-yl)pentanamide (3S)—N-cyclobutyl-3-({1-cyclopentyl-5-[2-(methylsulfanyl)phenyl]-1H-pyrazol-3-yl}formamido)-5-(piperidin-1-yl)pentanamide (3S)—N-cyclobutyl-3-{[1-cyclopentyl-5-(2-methoxyphenyl)-1H-pyrazol-3-yl]formamido}-5-(piperidin-1-yl)pentanamide (3S)—N-cyclobutyl-3-{[1-cyclopentyl-5-(thiophen-2-yl)-1H-pyrazol-3-yl]formamido}-5-(piperidin-1-yl)pentanamide (3S)—N-cyclobutyl-3-{[1-cyclopentyl-5-(2-ethylphenyl)-1H-pyrazol-3-yl]formamido}-5-(piperidin-1-yl)pentanamide 1-cyclopentyl-5-(2,6-dimethoxyphenyl)-N-[(2S)-4-(piperidin-1-yl)-1-(1H-1,2,3,4-tetrazol-5-yl)butan-2-yl]-1H-pyrazole-3-carboxamide (3S)—N-cyclobutyl-3-[(1-cyclopentyl-5-phenyl-1H-pyrazol-3-yl)formamido]-5-(piperidin-1-yl)pentanamide (3S)—N-cyclobutyl-3-({1-cyclopentyl-5-[4-fluoro-2-(2,2,2-trifluoroethoxy)phenyl]-1H-pyrazol-3-yl}formamido)-5-(piperidin-1-yl)pentanamide (3S)—N-cyclobutyl-3-{[1-cyclopentyl-5-(2-methanesulfonylphenyl)-1H-pyrazol-3-yl]formamido}-5-(piperidin-1-yl)pentanamide (3S)—N-cyclobutyl-3-{[1-cyclopentyl-5-(pyrimidin-5-yl)-1H-pyrazol-3-yl]formamido}-5-(piperidin-1-yl)pentanamide (3S)—N-cyclobutyl-3-{[1-cyclopentyl-5-(dimethyl-1,2-oxazol-4-yl)-1H-pyrazol-3-yl]formamido}-5-(piperidin-1-yl)pentanamide (3S)-3-{[5-(2-chloro-6-methoxyphenyl)-1-cyclopentyl-1H-pyrazol-3-yl]formamido}-N-cyclobutyl-5-(piperidin-1-yl)pentanamide (3S)—N-cyclobutyl-3-{[1-cyclopentyl-5-(2,6-dimethylphenyl)-1H-pyrazol-3-yl]formamido}-5-(piperidin-1-yl)pentanamide (3S)—N-cyclobutyl-3-{[1-cyclopentyl-5-(2-fluoro-6-methoxyphenyl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-5-(piperidin-1-yl)-N-[2-(1H-1,2,3,4-tetrazol-5-yl)ethyl]pentanamide 2-(3-{[(2S)-1-(cyclobutylcarbamoyl)-4-(piperidin-1-yl)butan-2-yl]carbamoyl}-1-cyclopentyl-1H-pyrazol-5-yl)pyridin-1-ium-1-olate (3S)—N-cyclobutyl-3-{[1-cyclopentyl-5-(pyridin-2-yl)-1H-pyrazol-3-yl]formamido}-5-(piperidin-1-yl)pentanamide (2S)—N-cyclobutyl-2-{[1-cyclopentyl-5-(2,6-dimethoxyphenyl)-1H-pyrazol-3-yl]formamido}-3-cyclopropylpropanamide (2S)—N,3-dicyclobutyl-2-{[1-cyclopentyl-5-(2,6-dimethoxyphenyl)-1H-pyrazol-3-yl]formamido}propanamide (3S)—N-cyclobutyl-3-{[1-cyclopentyl-5-(1,3-thiazol-4-yl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-ylmethyl)pentanamide (3S)-3-{[1-cyclopentyl-5-(2,6-dimethoxyphenyl)-1H-pyrazol-3-yl]formamido}-5-phenyl-N-(1,3-thiazol-2-yl)pentanamide (3S)-3-{[1-cyclopentyl-5-(2,6-dimethoxyphenyl)-1H-pyrazol-3-yl]formamido}-5-phenyl-N-(1H-1,2,3,4-tetrazol-5-yl)pentanamide (3S)-3-{[1-cyclopentyl-5-(2,6-dimethoxyphenyl)-1H-pyrazol-3-yl]formamido}-5-phenyl-N-(1,3-thiazol-2-ylmethyl)pentanamide (3S)-3-{[1-cyclopentyl-5-(2,6-dimethoxyphenyl)-1H-pyrazol-3-yl]formamido}-5-phenyl-N-(1H-1,2,3,4-tetrazol-5-ylmethyl)pentanamide (3S)-3-{[1-cyclopentyl-5-(2,6-dimethoxyphenyl)-1H-pyrazol-3-yl]formamido}-5-(3,3-difluoropiperidin-1-yl)-N-(1,3-thiazol-2-yl)pentanamide (2S)-2-{[1-cyclopentyl-5-(2,6-dimethoxyphenyl)-1H-pyrazol-3-yl]formamido}-3-cyclopropylpropanoic acid (2S)-3-cyclobutyl-2-{[1-cyclopentyl-5-(2,6-dimethoxyphenyl)-1H-pyrazol-3-yl]formamido}propanoic acid (2S)-2-{[1-cyclopentyl-5-(2,6-dimethoxyphenyl)-1H-pyrazol-3-yl]formamido}-4-phenyl-N-(1H-1,2,3,4-tetrazol-5-ylmethyl)butanamide (2S)-2-{[1-cyclopentyl-5-(2,6-dimethoxyphenyl)-1H-pyrazol-3-yl]formamido}-4-phenyl-N-(1,3-thiazol-2-ylmethyl)butanamide (2S)-2-{[1-cyclopentyl-5-(2,6-dimethoxyphenyl)-1H-pyrazol-3-yl]formamido}-4-phenylbutanoic acid 1-cyclopentyl-5-(2,6-dimethoxyphenyl)-N-[(2S)-4-phenyl-1-(1H-1,2,3,4-tetrazol-5-yl)butan-2-yl]-1H-pyrazole-3-carboxamide N-[(2S)-1-cyano-4-phenylbutan-2-yl]-1-cyclopentyl-5-(2,6-dimethoxyphenyl)-1H-pyrazole-3-carboxamide (3S)-3-{[1-cyclopentyl-5-(2,6-dimethoxyphenyl)-1H-pyrazol-3-yl]formamido}-5-phenylpentanamide (2S)-3-cyclopentyl-2-{[1-cyclopentyl-5-(2,6-dimethoxyphenyl)-1H-pyrazol-3-yl]formamido}propanoic acid (2S)-2-{[1-cyclopentyl-5-(2,6-dimethoxyphenyl)-1H-pyrazol-3-yl]formamido}-4-phenyl-N-(1H-1,2,3,4-tetrazol-5-yl)butanamide (2S)-2-{[1-cyclopentyl-5-(2,6-dimethoxyphenyl)-1H-pyrazol-3-yl]formamido}-4-phenyl-N-(1,3-thiazol-2-yl)butanamide (3S)—N-cyclobutyl-3-({1-cyclopentyl-5-[2-(propan-2-yl)phenyl]-1H-pyrazol-3-yl}formamido)-5-(piperidin-1-yl)pentanamide N-[(3R)-1-(cyclobutylamino)-5-(piperidin-1-yl)pentan-3-yl]-1-cyclopentyl-5-(2,6-dimethoxyphenyl)-1H-pyrazole-3-carboxamide (3S)—N-cyclobutyl-3-{[1-cyclopentyl-5-(2-ethyl-4-fluorophenyl)-1H-pyrazol-3-yl]formamido}-5-(piperidin-1-yl)pentanamide (3S)—N-cyclobutyl-3-({1-cyclopentyl-5-[2-(1,1-difluoroethyl)phenyl]-1H-pyrazol-3-yl}formamido)-5-(piperidin-1-yl)pentanamide (3S)-3-{[1-cyclopentyl-5-(2,6-dimethoxyphenyl)-1H-pyrazol-3-yl]formamido}-4-phenylbutanoic acid (3S)-3-{[1-cyclopentyl-5-(2,6-dimethoxyphenyl)-1H-pyrazol-3-yl]formamido}-4-phenyl-N-(1,3-thiazol-2-yl)butanamide (3S)-3-{[1-cyclopentyl-5-(2-ethylphenyl)-1H-pyrazol-3-yl]formamido}-5-(piperidin-1-yl)pentanoic acid hydrochloride (3S)-3-{[1-cyclopentyl-5-(2-ethylphenyl)-1H-pyrazol-3-yl]formamido}-5-(3,3-difluoropiperidin-1-yl)pentanoic acid (3S)-3-{[1-cyclopentyl-5-(2-ethylphenyl)-1H-pyrazol-3-yl]formamido}-5-(4,4-difluoropiperidin-1-yl)pentanoic acid (3S)-3-{[1-cyclopentyl-5-(2-ethylphenyl)-1H-pyrazol-3-yl]formamido}-5-(piperidin-1-yl)-N-(1,3-thiazol-2-yl)pentanamide (3S)-3-{[5-(2-chlorophenyl)-1-cyclopentyl-1H-pyrazol-3-yl]formamido}-N-cyclobutyl-5-(piperidin-1-yl)pentanamide (3S)—N-cyclobutyl-3-({1-cyclopentyl-5-[2-(trifluoromethyl)phenyl]-1H-pyrazol-3-yl}formamido)-5-(piperidin-1-yl)pentanamide (3S)-3-{[1-cyclopentyl-5-(2-ethylphenyl)-1H-pyrazol-3-yl]formamido}-5-(4,4-difluoropiperidin-1-yl)-N-(1,3-thiazol-2-yl)pentanamide (3S)-3-{[1-cyclopentyl-5-(2-ethylphenyl)-1H-pyrazol-3-yl]formamido}-5-(3,3-difluoropiperidin-1-yl)-N-(1,3-thiazol-2-yl)pentanamide (3S)—N-cyclobutyl-3-{[1-cyclopentyl-5-(2-ethylphenyl)-1H-pyrazol-3-yl]formamido}-5-(4,4-difluoropiperidin-1-yl)pentanamide (3S)—N-cyclobutyl-3-{[1-cyclopentyl-5-(2-ethylphenyl)-1H-pyrazol-3-yl]formamido}-5-(3,3-difluoropiperidin-1-yl)pentanamide (3S)—N-cyclobutyl-3-{[1-cyclopentyl-5-(2-cyclopropylphenyl)-1H-pyrazol-3-yl]formamido}-5-(piperidin-1-yl)pentanamide 1-cyclopentyl-5-(2,6-dimethoxyphenyl)-N-[(2S)-4-(piperidin-1-yl)-1-(4H-1,2,4-triazol-3-yl)butan-2-yl]-1H-pyrazole-3-carboxamide (3R,4E)-N-cyclobutyl-3-{[1-cyclopentyl-5-(2,6-dimethoxyphenyl)-1H-pyrazol-3-yl]formamido}-5-(4-fluorophenyl)pent-4-enamide (3S)—N-cyclobutyl-3-{[1-cyclopentyl-5-(2,6-dimethoxyphenyl)-1H-pyrazol-3-yl]formamido}-5-(4-fluorophenyl)pentanamide (3S)-3-{[1-cyclopentyl-5-(2,6-dimethoxyphenyl)-1H-pyrazol-3-yl]formamido}-5-(4-fluorophenyl)-N-(1,3-thiazol-2-yl)pentanamide (3R,4E)-N-cyclobutyl-3-{[1-cyclopentyl-5-(2,6-dimethoxyphenyl)-1H-pyrazol-3-yl]formamido}-5-(pyridin-3-yl)pent-4-enamide (3R,4E)-N-cyclobutyl-3-{[1-cyclopentyl-5-(2,6-dimethoxyphenyl)-1H-pyrazol-3-yl]formamido}-5-(pyridin-4-yl)pent-4-enamide (3S)—N-cyclobutyl-3-{[1-cyclopentyl-5-(2,6-dimethoxyphenyl)-1H-pyrazol-3-yl]formamido}-5-(pyridin-3-yl)pentanamide (3S)—N-cyclobutyl-3-{[1-cyclopentyl-5-(2,6-dimethoxyphenyl)-1H-pyrazol-3-yl]formamido}-5-(1-methylpiperidin-4-yl)pentanamide 1-cyclopentyl-5-(2,6-dimethoxyphenyl)-N-[(2S)-1-(1,3,4-oxadiazol-2-yl)-4-(piperidin-1-yl)butan-2-yl]-1H-pyrazole-3-carboxamide (3S)-3-({1-cyclopentyl-5-[2-(trifluoromethyl)phenyl]-1H-pyrazol-3-yl}formamido)-5-(3,3-difluoropiperidin-1-yl)pentanoic acid (3S)-3-({1-cyclopentyl-5-[2-(trifluoromethyl)phenyl]-1H-pyrazol-3-yl}formamido)-5-(4,4-difluoropiperidin-1-yl)pentanoic acid (3S)—N-cyclobutyl-3-({1-cyclopentyl-5-[2-(trifluoromethyl)phenyl]-1H-pyrazol-3-yl}formamido)-5-(3,3-difluoropiperidin-1-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-(1,3-oxazol-2-yl)pentanamide (3S)-3-({1-cyclopentyl-5-[2-(1,1-difluoroethyl)phenyl]-1H-pyrazol-3-yl}formamido)-5-(3,3-difluoropiperidin-1-yl)-N-(1,3-thiazol-2-yl)pentanamide (3S)-3-{[5-(2-chlorophenyl)-1-cyclopentyl-1H-pyrazol-3-yl]formamido}-5-(3,3-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(4,4-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-thiazol-2-yl)pentanamide (3S)-3-({1-cyclopentyl-5-[2-(1,1-difluoroethyl)phenyl]-1H-pyrazol-3-yl}formamido)-5-(3,3-difluoropiperidin-1-yl) pentanoic acid (3S)-3-{[5-(2-chlorophenyl)-1-cyclopentyl-1H-pyrazol-3-yl]formamido}-5-(3,3-difluoropiperidin-1-yl)pentanoic acid (3S)—N-cyclobutyl-3-({1-cyclopentyl-5-[2-(trifluoromethyl)thiophen-3-yl]-1H-pyrazol-3-yl}formamido)-5-(piperidin-1-yl)pentanamide (3R,4E)-N-cyclobutyl-3-{[1-cyclopentyl-5-(2,6-dimethoxyphenyl)-1H-pyrazol-3-yl]formamido}-5-(pyridin-2-yl) pent-4-enamide (3S)-3-({1-cyclopentyl-5-[2-(trifluoromethyl)phenyl]-1H-pyrazol-3-yl}formamido)-5-(4,4-difluoropiperidin-1-yl)-N-(5-methyl-1,3-thiazol-2-yl)pentanamide 1-cyclopentyl-N-[(2S)-4-(3,3-difluoropiperidin-1-yl)-1-(4H-1,2,4-triazol-3-yl)butan-2-yl]-5-[2-(trifluoromethyl) phenyl]-1H-pyrazole-3-carboxamide (3S)—N-cyclobutyl-3-{[1-cyclopentyl-5-(2-ethynylphenyl)-1H-pyrazol-3-yl]formamido}-5-(piperidin-1-yl)pentanamide (3S)—N-benzyl-3-({1-cyclopentyl-5-[2-(trifluoromethyl) phenyl]-1H-pyrazol-3-yl}formamido)-5-(4,4-difluoropiperidin-1-yl)pentanamide (3S)—N-(cyclohexylmethyl)-3-({1-cyclopentyl-5-[2-(trifluoromethyl)phenyl]-1H-pyrazol-3-yl}formamido)-5-(4,4-difluoropiperidin-1-yl)pentanamide (3S)—N-benzyl-3-({1-cyclopentyl-5-[2-(trifluoromethyl) phenyl]-1H-pyrazol-3-yl}formamido)-5-methylhexanamide N-benzyl-3-({1-cyclopentyl-5-[2-(trifluoromethyl)phenyl]-1H-pyrazol-3-yl}formamido)propanamide (3S)-3-{[1-cyclopentyl-5-(2,6-dimethoxyphenyl)-1H-pyrazol-3-yl]formamido}-N-(3,3-difluorocyclobutyl)-5-(piperidin-1-yl)pentanamide 1-cyclopentyl-5-(2,6-dimethoxyphenyl)-N-[(2S)-1-(1-methyl-1H-1,2,3,4-tetrazol-5-yl)-4-(piperidin-1-yl)butan-2-yl]-1H-pyrazole-3-carboxamide (3S)-3-{[5-(2-chlorophenyl)-1-cyclopentyl-1H-pyrazol-3-yl]formamido}-5-(3,3-difluoropiperidin-1-yl)-N-methyl-N-(1,3-thiazol-2-yl)pentanamide 1-cyclopentyl-5-(2,6-dimethoxyphenyl)-N-[(2S)-4-(piperidin-1-yl)-1-(1,3-thiazol-2-yl)butan-2-yl]-1H-pyrazole-3-carboxamide 3-({1-cyclopentyl-5-[2-(trifluoromethyl)phenyl]-1H-pyrazol-3-yl}formamido)-N-(1,3-thiazol-2-yl)propanamide 5-(2-chlorophenyl)-1-cyclopentyl-N-[(2S)-4-(3,3-difluoropiperidin-1-yl)-1-(4H-1,2,4-triazol-3-yl)butan-2-yl]-1H-pyrazole-3-carboxamide (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-oxazol-2-yl)pentanamide (3S)-3-{[5-(2-chlorophenyl)-1-cyclopentyl-1H-pyrazol-3-yl]formamido}-5-(3,3-difluoropiperidin-1-yl)-N-methyl-N-(1,3-oxazol-2-yl)pentanamide (3S)-3-{[5-(3-chloropyridin-4-yl)-1-cyclopentyl-1H-pyrazol-3-yl]formamido}-N-cyclobutyl-5-(3,3-difluoropiperidin-1-yl)pentanamide 5-(2-chlorophenyl)-1-cyclopentyl-N-[(2S)-4-(3,3-difluoropiperidin-1-yl)-1-(5-methyl-4H-1,2,4-triazol-3-yl)butan-2-yl]-1H-pyrazole-3-carboxamide 5-(2-chlorophenyl)-1-cyclopentyl-N-[(2S)-4-(3,3-difluoropiperidin-1-yl)-1-[5-(trifluoromethyl)-4H-1,2,4-triazol-3-yl]butan-2-yl]-1H-pyrazole-3-carboxamide (3S)—N-cyclobutyl-3-({1-cyclopentyl-5-[4-(trifluoromethyl)pyridin-3-yl]-1H-pyrazol-3-yl}formamido)-5-(3,3-difluoropiperidin-1-yl)pentanamide (3S)-3-({1-cyclopentyl-5-[2-(trifluoromethyl)phenyl]-1H-pyrazol-3-yl}formamido)-5-(4-fluorophenyl)pentanoic acid 1-cyclopentyl-N-[(2S)-4-(4-fluorophenyl)-1-(hydrazinecarbonyl)butan-2-yl]-5-[2-(trifluoromethyl)phenyl]-1H-pyrazole-3-carboxamide 5-(2-chlorophenyl)-1-cyclopentyl-N-[(2S)-4-(3,3-difluoropiperidin-1-yl)-1-(hydrazinecarbonyl)butan-2-yl]-1H-pyrazole-3-carboxamide (3S)-3-{[5-(4-chloropyridin-3-yl)-1-cyclopentyl-1H-pyrazol-3-yl]formamido}-N-cyclobutyl-5-(3,3-difluoropiperidin-1-yl)pentanamide (3S)-3-{[5-(4-chloropyridin-3-yl)-1-cyclopentyl-1H-pyrazol-3-yl]formamido}-5-(3,3-difluoropiperidin-1-yl)pentanoic acid (3S)-3-{[5-(2-chloropyridin-3-yl)-1-cyclopentyl-1H-pyrazol-3-yl]formamido}-5-(3,3-difluoropiperidin-1-yl)pentanoic acid (3S)-3-{[5-(2-chloropyridin-3-yl)-1-cyclopentyl-1H-pyrazol-3-yl]formamido}-N-cyclobutyl-5-(3,3-difluoropiperidin-1-yl)pentanamide 1-cyclopentyl-N-[(2S)-4-(4-fluorophenyl)-1-(4H-1,2,4-triazol-3-yl)butan-2-yl]-5-[2-(trifluoromethyl)phenyl]-1H-pyrazole-3-carboxamide 1-cyclopentyl-N-[(2S)-4-(4-fluorophenyl)-1-(5-methyl-4H-1,2,4-triazol-3-yl)butan-2-yl]-5-[2-(trifluoromethyl)phenyl]-1H-pyrazole-3-carboxamide 1-cyclopentyl-N-[(2S)-4-(4-fluorophenyl)-1-[5-(trifluoromethyl)-1,3,4-oxadiazol-2-yl]butan-2-yl]-5-[2-(trifluoromethyl)phenyl]-1H-pyrazole-3-carboxamide (3S)—N-cyclobutyl-3-({1-cyclopentyl-5-[3-(trifluoromethyl)pyridin-2-yl]-1H-pyrazol-3-yl}formamido)-5-(3,3-difluoropiperidin-1-yl)pentanamide (3S)—N-cyclobutyl-3-({1-cyclopentyl-5-[2-(trifluoromethyl)phenyl]-1H-pyrazol-3-yl}formamido)-5-(3,3-difluoropyrrolidin-1-yl)pentanamide (3S)-5-(3-cyanopyrrolidin-1-yl)-N-cyclobutyl-3-({1-cyclopentyl-5-[2-(trifluoromethyl)phenyl]-1H-pyrazol-3-yl}formamido)pentanamide (3S)-3-({1-cyclopentyl-5-[2-(trifluoromethyl)phenyl]-1H-pyrazol-3-yl}formamido)-5-(4-fluorophenyl)-N-(1-methylazetidin-3-yl)pentanamide (3S)—N-cyclobutyl-5-[cyclohexyl(methyl)amino]-3-({1-cyclopentyl-5-[2-(trifluoromethyl)phenyl]-1H-pyrazol-3-yl}formamido)pentanamide (3S)-5-cyclohexyl-3-({1-cyclopentyl-5-[2-(trifluoromethyl) phenyl]-1H-pyrazol-3-yl}formamido)pentanoic acid (3S)-3-({1-cyclopentyl-5-[2-(trifluoromethyl)phenyl]-1H-pyrazol-3-yl}formamido)-5-(3,3-difluoropyrrolidin-1-yl)pentanoic acid (3S)-3-({1-cyclopentyl-5-[2-(trifluoromethyl)phenyl]-1H-pyrazol-3-yl}formamido)-5-(morpholin-4-yl)pentanoic acid (3S)-3-({1-cyclopentyl-5-[2-(trifluoromethyl)phenyl]-1H-pyrazol-3-yl}formamido)-5-[(2S)-2-(trifluoromethyl)piperidin-1-yl]pentanoic acid (3S)-3-({1-cyclopentyl-5-[2-(trifluoromethyl)phenyl]-1H-pyrazol-3-yl}formamido)-5-[(2R)-2-(trifluoromethyl)piperidin-1-yl]pentanoic acid (3S)-3-({1-cyclopentyl-5-[2-(trifluoromethyl)phenyl]-1H-pyrazol-3-yl}formamido)-N-methyl-N-(1,3-thiazol-2-yl)-5-[(2R)-2-(trifluoromethyl)piperidin-1-yl]pentanamide (3S)—N-cyclobutyl-5-[cyclopentyl(methyl)amino]-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-(morpholin-4-yl)pentanamide (3S)—N-cyclobutyl-3-({1-cyclopentyl-5-[2-(trifluoromethyl)phenyl]-1H-pyrazol-3-yl}formamido)-5-(dipropylamino)pentanamide (3S)—N-cyclobutyl-3-({1-cyclopentyl-5-[2-(trifluoromethyl)phenyl]-1H-pyrazol-3-yl}formamido)-5-[methyl(2-methylpropyl)amino]pentanamide (3S)-3-(l{1-cyclopentyl-5-[2-(trifluoromethyl)phenyl]-1H-pyrazol-3-yl}formamido)-5-(piperidin-1-yl)pentanoic acid (3S)-3-({1-cyclopentyl-5-[2-(trifluoromethyl)phenyl]-1H-pyrazol-3-yl}formamido)-N-methyl-5-(morpholin-4-yl)-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-[(2S)-2-(trifluoromethyl)piperidin-1-yl]pentanamide (3S)—N-cyclobutyl-3-({1-cyclopentyl-5-[2-(trifluoromethyl)phenyl]-1H-pyrazol-3-yl}formamido)-5-(4-fluorophenyl)pentanamide (3S)-5-{8-azabicyclo[3.2.1]octan-8-yl}-N-cyclobutyl-3-({1-cyclopentyl-5-[2-(trifluoromethyl)phenyl]-1H-pyrazol-3-yl}formamido)pentanamide (3S)-3-({1-cyclopentyl-5-[2-(trifluoromethyl)phenyl]-1H-pyrazol-3-yl}formamido)-5-(pyrrolidin-1-yl)pentanoic acid (3S)-3-({1-cyclopentyl-5-[2-(trifluoromethyl)phenyl]-1H-pyrazol-3-yl}formamido)-N-methyl-5-(4-methyl-1H-pyrazol-1-yl)-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-(4-methyl-1H-pyrazol-1-yl)pentanamide (3S)-3-({1-cyclopentyl-5-[2-(trifluoromethyl)phenyl]-1H-pyrazol-3-yl}formamido)-5-(3,5-dimethyl-1H-pyrazol-1-yl)-N-methyl-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-(3,5-dimethyl-1H-pyrazol-1-yl)pentanamide (3S)—N-cyclobutyl-3-({1-cyclopentyl-5-[2-(trifluoromethyl)phenyl]-1H-pyrazol-3-yl}formamido)-5-(pyrrolidin-1-yl)pentanamide (3S)-5-(azepan-1-yl)-N-cyclobutyl-3-({1-cyclopentyl-5-[2-(trifluoromethyl)phenyl]-1H-pyrazol-3-yl}formamido)pentanamide (3S)—N-cyclobutyl-5-[cyclobutyl(methyl)amino]-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-{2-oxa-6-azaspiro[3.3]heptan-6-yl}pentanamide (3S)-3-({1-cyclopentyl-5-[2-(trifluoromethyl)phenyl]-1H-pyrazol-3-yl}formamido)-5-oxo-5-(piperidin-1-yl)pentanoic acid (3S)-3-({1-cyclopentyl-5-[2-(trifluoromethyl)phenyl]-1H-pyrazol-3-yl}formamido)-5-(3,3-difluoropiperidin-1-yl)-5-oxopentanoic acid (3S)-3-({1-cyclopentyl-5-[2-(trifluoromethyl)phenyl]-1H-pyrazol-3-yl}formamido)-5-(4-fluorophenyl)-N-(pyrrolidin-1-yl)pentanamide (3S)—N-cyclobutyl-3-({1-cyclopentyl-5-[2-(trifluoromethyl)phenyl]-1H-pyrazol-3-yl}formamido)-5-[methyl(1-methylcyclopentyl)amino]pentanamide (3R)—N-cyclobutyl-3-({1-cyclopentyl-5-[2-(trifluoromethyl)phenyl]-1H-pyrazol-3-yl}formamido)-5-oxo-5-(piperidin-1-yl)pentanamide (3R)—N-cyclobutyl-3-({1-cyclopentyl-5-[2-(trifluoromethyl)phenyl]-1H-pyrazol-3-yl}formamido)-5-(3,3-difluoropiperidin-1-yl)-5-oxopentanamide (3S)—N-cyclobutyl-3-({1-cyclopentyl-5-[2-(trifluoromethyl)phenyl]-1H-pyrazol-3-yl}formamido)-5-(dimethylamino)pentanamide (3S)—N-cyclobutyl-3-({1-cyclopentyl-5-[2-(trifluoromethyl)phenyl]-1H-pyrazol-3-yl}formamido)-5-(2,2-dimethylpiperidin-1-yl)pentanamide (3R)-3-({1-cyclopentyl-5-[2-(trifluoromethyl)phenyl]-1H-pyrazol-3-yl}formamido)-4-(3,3-difluoropyrrolidin-1-yl)butanoic acid (3R)-3-({1-cyclopentyl-5-[2-(trifluoromethyl)phenyl]-1H-pyrazol-3-yl}formamido)-4-(3,3-difluoropiperidin-1-yl)butanoic acid (3S)-3-({1-cyclopentyl-5-[2-(trifluoromethyl)phenyl]-1H-pyrazol-3-yl}formamido)-N-(3,3-difluorocyclobutyl)-5-(piperidin-1-yl)pentanamide (3S)-5-{2-azabicyclo[2.2.2]octan-2-yl}-N-cyclobutyl-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-{2-oxa-5-azaspiro[3.5]nonan-5-yl}pentanamide (3R)—N-cyclobutyl-3-({1-cyclopentyl-5-[2-(trifluoromethyl)phenyl]-1H-pyrazol-3-yl}formamido)-4-(3,3-difluoropyrrolidin-1-yl)butanamide (3R)—N-cyclobutyl-3-({1-cyclopentyl-5-[2-(trifluoromethyl)phenyl]-1H-pyrazol-3-yl}formamido)-4-(3,3-difluoropiperidin-1-yl)butanamide (3S)-3-({1-cyclopentyl-5-[2-(trifluoromethyl)pyridin-3-yl]-1H-1,2,4-triazol-3-yl}formamido)-5-(3,3-difluoropiperidin-1-yl)pentanoic acid (2S)-3-cyclopentyl-2-({1-cyclopentyl-5-[2-(trifluoromethyl)phenyl]-1H-pyrazol-3-yl}formamido)propanoic acid (2S)-2-({1-cyclopentyl-5-[2-(trifluoromethyl)phenyl]-1H-pyrazol-3-yl}formamido)-4-methylpentanoic acid (2S)-2-({1-cyclopentyl-5-[2-(trifluoromethyl)phenyl]-1H-pyrazol-3-yl}formamido)-3-methylbutanoic acid (3S)-3-({1-cyclopentyl-5-[2-(trifluoromethyl)phenyl]-1H-pyrazol-3-yl}formamido)-5-(3,3-difluoropiperidin-1-yl)-N-(trifluoromethane)sulfonylpentanamide (3R)-4-[cyclohexyl(methyl)amino]-3-({1-cyclopentyl-5-[2-(trifluoromethyl)phenyl]-1H-pyrazol-3-yl}formamido)butanoic acid (3S)-3-({1-cyclopentyl-5-[2-(trifluoromethyl)phenyl]-1H-pyrazol-3-yl}formamido)-5-(3,3-difluoroazetidin-1-yl)pentanoic acid (3S)—N-cyclobutyl-3-({1-cyclopentyl-5-[2-(trifluoromethyl)phenyl]-1H-pyrazol-3-yl}formamido)-5-(3,3-difluoroazetidin-1-yl)pentanamide
(3S)—N-cyclobutyl-3-({1-cyclopentyl-5-[2-(trifluoromethyl)phenyl]-1H-pyrazol-3-yl}formamido)-5-(cyclopentylformamido)pentanamide
(3S)-3-({1-cyclopentyl-5-[2-(1,1-difluoroethyl)phenyl]-1H-pyrazol-3-yl}formamido)-5-(3,3-difluoropyrrolidin-1-yl)pentanoic acid
(3S)-3-({1-cyclopentyl-5-[2-(trifluoromethyl)phenyl]-1H-pyrazol-3-yl}formamido)-5-(cyclopentylformamido)pentanoic acid
(3S)—N-cyclobutyl-3-({1-cyclopentyl-5-[2-(trifluoromethyl)phenyl]-1H-pyrazol-3-yl}formamido)-5-(oxetan-3-ylformamido)pentanamide
1-cyclopentyl-N-[(2S)-4-(3,3-difluoropiperidin-1-yl)-4-oxo-1-sulfamoylbutan-2-yl]-5-[2-(trifluoromethyl)phenyl]-1H-pyrazole-3-carboxamide
N-[(2S)-1-(cyclobutylsulfamoyl)-4-(3,3-difluoropiperidin-1-yl)-4-oxobutan-2-yl]-1-cyclopentyl-5-[2-(trifluoromethyl)phenyl]-1H-pyrazole-3-carboxamide
(2S)-2-({1-cyclopentyl-5-[2-(trifluoromethyl)phenyl]-1H-pyrazol-3-yl}formamido)-N-(2-methoxyethyl)-N-methyl-4-phenylbutanamide
(3R)-3-(cyclohexylcarbamoyl)-3-({1-cyclopentyl-5-[2-(trifluoromethyl)phenyl]-1H-pyrazol-3-yl}formamido)propanoic acid
(3R)-3-({1-cyclopentyl-5-[2-(trifluoromethyl)phenyl]-1H-pyrazol-3-yl}formamido)-4-(4-fluorophenoxy)butanoic acid
(3R)—N-cyclobutyl-3-({1-cyclopentyl-5-[2-(trifluoromethyl)phenyl]-1H-pyrazol-3-yl}formamido)-4-(4-fluorophenoxy)butanamide
(3R)—N-cyclobutyl-4-[cyclohexyl(methyl)amino]-3-({1-cyclopentyl-5-[2-(trifluoromethyl)phenyl]-1H-pyrazol-3-yl}formamido)butanamide
(3S)-3-({1-cyclopentyl-5-[2-(trifluoromethyl)phenyl]-1H-pyrazol-3-yl}formamido)-5-[(3,3-difluorocyclobutyl)amino]pentanoic acid
(2R)—N-cyclobutyl-N'-cyclohexyl-2-({1-cyclopentyl-5-[2-(trifluoromethyl)phenyl]-1H-pyrazol-3-yl}formamido)butanediamide
(3R)-3-({1-cyclopentyl-5-[2-(trifluoromethyl)phenyl]-1H-pyrazol-3-yl}formamido)-N-(3-methyloxetan-3-yl)-5-oxo-5-(piperidin-1-yl)pentanamide
1-cyclopentyl-N-[(2S)-4-(3,3-difluoropiperidin-1-yl)-1-(1H-1,2,3,4-tetrazol-5-yl)butan-2-yl]-5-[2-(trifluoromethyl)phenyl]-1H-pyrazole-3-carboxamide
(3S)-3-({1-cyclobutyl-5-[2-(trifluoromethyl)phenyl]-1H-pyrazol-3-yl}formamido)-5-(3,3-difluoropiperidin-1-yl)pentanoic acid
(3S)-5-(3,3-difluoropiperidin-1-yl)-3-{[1-(oxan-4-yl)-5-[2-(trifluoromethyl)phenyl]-1H-pyrazol-3-yl]formamido}pentanoic acid
(3S)-3-({1-cyclopentyl-5-[4-fluoro-2-(trifluoromethyl)phenyl]-1H-pyrazol-3-yl}formamido)-5-(3,3-difluoropiperidin-1-yl)pentanoic acid
(3S)-3-({5-[4-chloro-2-(trifluoromethyl)phenyl]-1-cyclopentyl-1H-pyrazol-3-yl}formamido)-5-(3,3-difluoropiperidin-1-yl)pentanoic acid
(3S)-3-({5-[2-chloro-6-(trifluoromethyl)phenyl]-1-cyclopentyl-1H-pyrazol-3-yl}formamido)-5-(3,3-difluoropiperidin-1-yl)pentanoic acid
(3S)-3-{[1-(cyclopropylmethyl)-5-[2-(trifluoromethyl)phenyl]-1H-pyrazol-3-yl]formamido}-5-(3,3-difluoropiperidin-1-yl)pentanoic acid
(3R)-3-[cyclohexyl(methyl)carbamoyl]-3-({1-cyclopentyl-5-[2-(trifluoromethyl)phenyl]-1H-pyrazol-3-yl}formamido)propanoic acid
(3R)-3-({1-cyclopentyl-5-[2-(trifluoromethyl)phenyl]-1H-pyrazol-3-yl}formamido)-3-[(oxan-4-yl)carbamoyl]propanoic acid
(3R)-3-({1-cyclopentyl-5-[2-(trifluoromethyl)phenyl]-1H-pyrazol-3-yl}formamido)-3-[(4-fluorophenyl)carbamoyl]propanoic acid
(2R)—N-cyclobutyl-N'-cyclohexyl-2-({1-cyclopentyl-5-[2-(trifluoromethyl)phenyl]-1H-pyrazol-3-yl}formamido)-N'-methylbutanediamide
(2R)—N-cyclobutyl-2-({1-cyclopentyl-5-[2-(trifluoromethyl)phenyl]-1H-pyrazol-3-yl}formamido)-N'-(oxan-4-yl)butanediamide
1-cyclopentyl-N-[(3R)-1-(4-fluorophenyl)-2,5-dioxopyrrolidin-3-yl]-5-[2-(trifluoromethyl)phenyl]-1H-pyrazole-3-carboxamide
(2S)-2-({1-cyclopentyl-5-[3-(trifluoromethyl)pyridin-2-yl]-1H-1,2,4-triazol-3-yl}formamido)-N-(2-methoxyethyl)-N-methyl-4-phenylbutanamide
(3S)-5-(3,3-difluoropiperidin-1-yl)-3-{[1-(2-methylpropyl)-5-[2-(trifluoromethyl)phenyl]-1H-pyrazol-3-yl]formamido}pentanoic acid
(3S)-3-({1-cyclopentyl-5-[2-(trifluoromethyl)phenyl]-1H-pyrazol-3-yl}formamido)-5-(3,3,4,4,5,5-hexafluoropiperidin-1-yl)pentanoic acid
(3S)-3-({1-cyclopentyl-5-[2-(trifluoromethyl)phenyl]-1H-pyrazol-3-yl}formamido)-5-(3,3-difluoropyrrolidin-1-yl)hexanoic acid
(3S)-5-(3,3-difluoropiperidin-1-yl)-3-{[1-(2,2-dimethylpropyl)-5-[2-(trifluoromethyl)phenyl]-1H-pyrazol-3-yl]formamido}pentanoic acid
(2S)-2-({1-cyclopentyl-5-[2-(trifluoromethyl)phenyl]-1H-pyrazol-3-yl}formamido)-N-(2-methoxyethyl)-N-methyl-3-phenoxypropanamide
(3S)-3-{[1-(cyclobutylmethyl)-5-[2-(trifluoromethyl)phenyl]-1H-pyrazol-3-yl]formamido}-5-(3,3-difluoropiperidin-1-yl)pentanoic acid
(3S,5S)-3-({1-cyclopentyl-5-[2-(trifluoromethyl)phenyl]-1H-pyrazol-3-yl}formamido)-5-(3,3-difluoropyrrolidin-1-yl)hexanoic acid
(3S)—N-cyclobutyl-3-({1-cyclopentyl-5-[2-(trifluoromethyl)phenyl]-1H-pyrazol-3-yl}formamido)-5-(3,3-difluoropyrrolidin-1-yl)hexanamide
(3S)-3-({1-cyclopentyl-5-[2-(trifluoromethyl)phenyl]-1H-pyrazol-3-yl}formamido)-5-(3,3,4,4-tetrafluoropyrrolidin-1-yl)pentanoic acid
(3S,5R)-3-({1-cyclopentyl-5-[2-(trifluoromethyl)phenyl]-1H-pyrazol-3-yl}formamido)-5-(3,3-difluoropiperidin-1-yl)hexanoic acid
(3S,5S)-3-({1-cyclopentyl-5-[2-(trifluoromethyl)phenyl]-1H-pyrazol-3-yl}formamido)-5-(3,3-difluoropiperidin-1-yl)hexanoic acid
(2S)-3-cyclohexyl-2-({1-cyclopentyl-5-[2-(trifluoromethyl)phenyl]-1H-pyrazol-3-yl}formamido)propanoic acid
(3S)-3-({1-cyclopentyl-5-[2-(trifluoromethyl)phenyl]-1H-pyrazol-3-yl}formamido)-5-[3-(trifluoromethyl)pyrrolidin-1-yl]pentanoic acid
(3R)-3-({1-cyclopentyl-5-[2-(trifluoromethyl)phenyl]-1H-pyrazol-3-yl}formamido)-5-(3,3-difluoropiperidin-1-yl)pentanoic acid
(3S)-5-(3,3-difluoropiperidin-1-yl)-3-({1-propyl-5-[2-(trifluoromethyl)phenyl]-1H-pyrazol-3-yl}formamido)pentanoic acid (3S)-3-({1-cyclopentyl-5-[2-(trifluoromethyl)phenyl]-1H-pyrazol-3-yl}formamido)-5-[(3R,4S)-3,4-difluoropyrrolidin-1-yl]pentanoic acid (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid (3S)-3-({1-cyclopentyl-5-[2-(trifluoromethyl)phenyl]-1H-pyrazol-3-yl}formamido)-5-[(3 S)-3-fluoropiperidin-1-yl]pentanoic acid (3S)-3-({1-cyclopentyl-5-[2-(trifluoromethyl)phenyl]-1H-pyrazol-3-yl}formamido)-5-[(3R)-3-fluoropiperidin-1-yl]pentanoic acid (3S)-3-({1-cyclopentyl-5-[2-(trifluoromethyl)phenyl]-1H-pyrazol-3-yl}formamido)-5-[(3S)-3-fluoropyrrolidin-1-yl]pentanoic acid (3S)-3-({1-cyclopentyl-5-[2-(trifluoromethyl)phenyl]-1H-pyrazol-3-yl}formamido)-5-(2-oxopiperidin-1-yl)pentanoic acid (3S)-3-({1-cyclopentyl-5-[2-(trifluoromethyl)phenyl]-1H-pyrazol-3-yl}formamido)-5-(3,3-dimethylazetidin-1-yl)pentanoic acid (3S)-3-({1-cyclopentyl-5-[2-(1,1-difluoroethyl)phenyl]-1H-pyrazol-3-yl}formamido)-5-(3,3-difluoroazetidin-1-yl)pentanoic acid (3S)-3-({1-cyclopentyl-5-[2-(trifluoromethyl)phenyl]-1H-pyrazol-3-yl}formamido)-5-[(3R)-3-fluoropyrrolidin-1-yl]pentanoic acid (3S)-3-({1-cyclopentyl-5-[2-(trifluoromethyl)phenyl]-1H-pyrazol-3-yl}formamido)-5-{5,5-difluoro-2-azaspiro[3.3]heptan-2-yl}pentanoic acid (2S)-3-(tert-butoxy)-2-({1-cyclopentyl-5-[2-(trifluoromethyl)phenyl]-1H-pyrazol-3-yl}formamido)-N-(2-methoxyethyl)-N-methylpropanamide (3S)-3-({1-cyclopentyl-5-[2-(1,1-difluoroethyl)phenyl]-1H-pyrazol-3-yl}formamido)-5-[(3R)-3-fluoropiperidin-1-yl]pentanoic acid (3S)-3-({1-cyclopentyl-5-[2-(1,1-difluoroethyl)phenyl]-1H-pyrazol-3-yl}formamido)-5-[trans-3,4-difluoropyrrolidin-1-yl]pentanoic acid (3S)-3-({1-cyclopentyl-5-[2-(1,1-difluoroethyl)phenyl]-1H-pyrazol-3-yl}formamido)-5-[trans-3,4-dimethylpyrrolidin-1-yl]hexanoic acid (2S,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid (2R,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid (3S)-3-({1-cyclopentyl-5-[2-(1,1-difluoroethyl)phenyl]-1H-pyrazol-3-yl}formamido)-5-[cis-3,4-difluoropyrrolidin-1-yl]pentanoic acid (3S,5R)-3-({1-cyclopentyl-5-[2-(1,1-difluoroethyl)phenyl]-1H-pyrazol-3-yl}formamido)-5-[trans-3,4-difluoropyrrolidin-1-yl]hexanoic acid (3S,5S)-3-({1-cyclopentyl-5-[2-(1,1-difluoroethyl)phenyl]-1H-pyrazol-3-yl}formamido)-5-(3,3-difluoropyrrolidin-1-yl)hexanoic acid (3S)-3-({1-cyclopentyl-5-[2-(trifluoromethyl)phenyl]-1H-pyrazol-3-yl}formamido)-5-[3-(trifluoromethyl)azetidin-1-yl]pentanoic acid (3S)-3-({1-cyclopentyl-5-[2-(trifluoromethyl)phenyl]-1H-pyrazol-3-yl}formamido)-5-{3,3-difluoro-8-azabicyclo[3.2.1]octan-8-yl}pentanoic acid (3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}pentanoic acid (3S)-3-({1-cyclopentyl-5-[2-(trifluoromethyl)phenyl]-1H-pyrazol-3-yl}formamido)-5-(2,6-dioxopiperidin-1-yl)pentanoic acid (3S)-3-({1-cyclopentyl-5-[2-(1,1-difluoroethyl)phenyl]-1H-pyrazol-3-yl}formamido)-5-[(2R)-4,4-difluoro-2-methylpyrrolidin-1-yl]pentanoic acid (3S)-3-({1-cyclopentyl-5-[2-(trifluoromethyl)phenyl]-1H-pyrazol-3-yl}formamido)-5-{8,8-difluoro-3-azabicyclo[3.2.1]octan-3-yl}pentanoic acid (3S)-3-({1-cyclopentyl-5-[2-(1,1-difluoroethyl)phenyl]-1H-pyrazol-3-yl}formamido)-5-(5,5-difluoro-2-methylpiperidin-1-yl)pentanoic acid (3S)-3-({1-cyclopentyl-5-[2-(trifluoromethyl)phenyl]-1H-pyrazol-3-yl}formamido)-5-(2,2-dimethyl-4-oxopyrrolidin-1-yl)pentanoic acid (3S)-3-({1-cyclopentyl-5-[2-(trifluoromethyl)phenyl]-1H-pyrazol-3-yl}formamido)-5-(3-fluoro-3-methylpyrrolidin-1-yl)pentanoic acid (3S)-3-({1-cyclopentyl-5-[2-(trifluoromethyl)phenyl]-1H-pyrazol-3-yl}formamido)-5-[(3S,4R)-3,4-difluoropiperidin-1-yl]pentanoic acid (3S)-3-({1-cyclopentyl-5-[2-(1,1-difluoroethyl)phenyl]-1H-pyrazol-3-yl}formamido)-5-(2,2-dimethyl-4-oxopiperidin-1-yl)pentanoic acid (3S)-3-({1-cyclopentyl-5-[2-(trifluoromethyl)phenyl]-1H-pyrazol-3-yl}formamido)-5-(4,4-difluoro-2,2-dimethylpyrrolidin-1-yl)pentanoic acid (3S)-3-({1-cyclopentyl-5-[2-(trifluoromethyl)phenyl]-1H-pyrazol-3-yl}formamido)-5-(3-fluoro-3-methylpiperidin-1-yl)pentanoic acid trifluoroacetate (3S)-3-({1-cyclopentyl-5-[2-(trifluoromethyl)phenyl]-1H-pyrazol-3-yl}formamido)-5-[(3S)-3-fluoro-3-methylpiperidin-1-yl]pentanoic acid (3S)-3-({1-cyclopentyl-5-[2-(trifluoromethyl)phenyl]-1H-pyrazol-3-yl}formamido)-5-{[1-(trifluoromethyl)cyclopentyl]amino}pentanoic acid trifluoroacetate (3S)—N-cyclobutyl-5-cyclohexyl-3-{[5-(2,6-dimethoxyphenyl)-1-(4-fluorophenyl)-1H-pyrazol-3-yl]formamido}pentanamide (3S)-5-cyclohexyl-3-{[1-cyclopentyl-5-(2,6-dimethoxyphenyl)-1H-pyrazol-3-yl]formamido}pentanoic acid (3S)-5-cyclohexyl-3-{[1-cyclohexyl-5-(2,6-dimethoxyphenyl)-1H-pyrazol-3-yl]formamido}pentanoic acid (3S)-5-cyclohexyl-3-{[5-(2,6-dimethoxyphenyl)-1-propyl-1H-pyrazol-3-yl]formamido}pentanoic acid (3S)—N-cyclobutyl-5-cyclohexyl-3-{[1-cyclopentyl-5-(2,6-dimethoxyphenyl)-1H-pyrazol-3-yl]formamido}pentanamide (3S)—N-cyclobutyl-5-cyclohexyl-3-{[1-cyclohexyl-5-(2,6-dimethoxyphenyl)-1H-pyrazol-3-yl]formamido}pentanamide (3S)—N-cyclobutyl-5-cyclohexyl-3-{[5-(2,6-dimethoxyphenyl)-1-propyl-1H-pyrazol-3-yl]formamido}pentanamide 1-cyclopentyl-N-[(2S)-4-{6,6-difluoro-3-azabicyclo[3.1.0]hexan-3-yl}-1-(1H-1,2,3,4-tetrazol-5-yl)butan-2-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid 1-cyclopentyl-N-[(2S)-4-[(3S,4S)-3,4-difluoropyrrolidin-1-yl]-1-(1H-1,2,3,4-tetrazol-5-yl)butan-2-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-[(3R,4R)-3,4-difluoropyrrolidin-1-yl]pentanoic acid (2S,3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanoic acid (2R,3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanoic acid (3S)—N-cyclobutyl-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanamide 1-cyclopentyl-N-[(3S)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide 1-cyclopentyl-N-[(3S,4R)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-(3,5-difluoropiperidin-1-yl)pentanoic acid 1-cyclopentyl-N-[(2S)-4-(3,3-difluoropiperidin-1-yl)-1-(1H-1,2,3,4-tetrazol-5-yl)butan-2-yl]-5-[3-(trifluoromethyl)pyridin-2-yl]-1H-pyrazole-3-carboxamide (3S)-3-({1-cyclopentyl-5-[2-(trifluoromethyl)phenyl]-1H-pyrazol-3-yl}formamido)-5-(2,5-dioxopyrrolidin-1-yl)pentanoic acid (3S)-5-cyclohexyl-3-{[5-(2,6-dimethoxyphenyl)-1-methyl-1H-pyrazol-3-yl]formamido}pentanoic acid (3S)-5-cyclohexyl-3-{[1-cyclooctyl-5-(2,6-dimethoxyphenyl)-1H-pyrazol-3-yl]formamido}pentanoic acid (3S)-5-cyclohexyl-3-{[1-(cyclohexylmethyl)-5-(2,6-dimethoxyphenyl)-1H-pyrazol-3-yl]formamido}pentanoic acid (3S)-5-cyclohexyl-3-{[5-(2,6-dimethoxyphenyl)-1-(pentan-3-yl)-1H-pyrazol-3-yl]formamido}pentanoic acid 1-cyclopentyl-N-[(2S)-4-(2,6-dioxopiperidin-1-yl)-1-(1H-1,2,3,4-tetrazol-5-yl)butan-2-yl]-5-[2-(trifluoromethyl)phenyl]-1H-pyrazole-3-carboxamide (3S)—N-cyclobutyl-3-({5-cyclopentyl-1-[2-(trifluoromethyl)phenyl]-1H-1,2,4-triazol-3-yl}formamido)-5-(piperidin-1-yl)pentanamide (3S)—N-cyclobutyl-3-({1-cyclopentyl-5-[2-(trifluoromethyl)phenyl]-1H-1,2,4-triazol-3-yl}formamido)-5-(piperidin-1-yl)pentanamide (3S)—N-cyclobutyl-3-({1-cyclopentyl-5-[2-(trifluoromethyl)phenyl]-1H-1,2,4-triazol-3-yl}formamido)-5-(3,3-difluoropiperidin-1-yl)pentanamide (3S)—N-cyclobutyl-3-({5-cyclopentyl-1-[2-(trifluoromethyl)phenyl]-1H-1,2,4-triazol-3-yl}formamido)-5-(3,3-difluoropiperidin-1-yl)pentanamide (3S)-3-({5-cyclopentyl-1-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide (3S)-3-({1-cyclopentyl-5-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide (3S)-3-({5-cyclopentyl-1-[2-(trifluoromethyl)phenyl]-1H-1,2,4-triazol-3-yl}formamido)-5-(3,3-difluoropiperidin-1-yl)pentanoic acid (3S)-3-({1-cyclopentyl-5-[2-(trifluoromethyl)phenyl]-1H-1,2,4-triazol-3-yl}formamido)-5-(3,3-difluoropiperidin-1-yl)pentanoic acid (3S)—N-cyclobutyl-3-({2-cyclopentyl-1-[2-(trifluoromethyl)phenyl]-1H-imidazol-4-yl}formamido)-5-(3,3-difluoropiperidin-1-yl)pentanamide (3S)-3-({2-cyclopentyl-1-[2-(trifluoromethyl)phenyl]-1H-imidazol-4-yl}formamido)-5-(3,3-difluoropiperidin-1-yl)-N-methyl-N-(1,3-thiazol-2-yl)pentanamide (3S)-3-(1-{5-cyclopentyl-1-[2-(trifluoromethyl)phenyl]-1H-1,2,4-triazol-3-yl}-N-methylformamido)-5-(3,3-difluoropiperidin-1-yl)-N-methyl-N-(1,3-thiazol-2-yl)pentanamide (3S)-3-{[4-(2-chlorophenyl)-1-methyl-5-(2-methylpropyl)-1H-imidazol-2-yl]formamido}-5-(3,3-difluoropiperidin-1-yl)pentanoic acid (3S)-3-{[4-(2-chlorophenyl)-1-methyl-5-(2-methylpropyl)-1H-imidazol-2-yl]formamido}-5-(3,3-difluoropiperidin-1-yl)-N-methyl-N-(1,3-thiazol-2-yl)pentanamide (3S)-3-{[4-(2-chlorophenyl)-1-methyl-5-(2-methylpropyl)-1H-imidazol-2-yl]formamido}-N-cyclobutyl-5-(3,3-difluoropiperidin-1-yl)pentanamide (3S)-3-({1-cyclopentyl-5-[3-(trifluoromethyl)pyridin-2-yl]-1H-1,2,4-triazol-3-yl}formamido)-5-(3,3-difluoropiperidin-1-yl)pentanoic acid (3S)-3-({5-cyclopentyl-1-[2-(trifluoromethyl)pyridin-3-yl]-1H-1,2,4-triazol-3-yl}formamido)-5-(3,3-difluoropiperidin-1-yl)pentanoic acid (3S)—N-cyclobutyl-3-({1-cyclopentyl-5-[3-(trifluoromethyl)pyridin-2-yl]-1H-1,2,4-triazol-3-yl}formamido)-5-(3,3-difluoropiperidin-1-yl)pentanamide (3S)—N-cyclobutyl-3-({5-cyclopentyl-1-[2-(trifluoromethyl)pyridin-3-yl]-1H-1,2,4-triazol-3-yl}formamido)-5-(3,3-difluoropiperidin-1-yl)pentanamide (3S)—N-cyclobutyl-3-({1-cyclopentyl-5-[2-(trifluoromethyl)pyridin-3-yl]-1H-1,2,4-triazol-3-yl}formamido)-5-(3,3-difluoropiperidin-1-yl)pentanamide (2S)-2-({5-cyclopentyl-1-[2-(trifluoromethyl)phenyl]-1H-1,2,4-triazol-3-yl}formamido)-N-(2-methoxyethyl)-N-methyl-4-phenylbutanamide (2S)-2-({1-cyclopentyl-5-[2-(trifluoromethyl)phenyl]-1H-1,2,4-triazol-3-yl}formamido)-N-(2-methoxyethyl)-N-methyl-4-phenylbutanamide (3S)-3-({5-cyclopentyl-1-[2-(trifluoromethyl)phenyl]-1H-1,2,4-triazol-3-yl}formamido)-5-(3,3-difluoropyrrolidin-1-yl)pentanoic acid 5-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-1,2,4-triazole-3-carboxamide (3S)-3-({2-cyclopentyl-1-[2-(trifluoromethyl)phenyl]-1H-imidazol-4-yl}formamido)-5-(3,3-difluoropiperidin-1-yl)pentanoic acid; and 2-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-imidazole-4-carboxamide, or a pharmaceutically acceptable salt, prodrug, or salt of a prodrug thereof.

One aspect of an embodiment of the present disclosure includes wherein capillary function is improved.

One aspect of an embodiment of the present disclosure includes wherein receptor occupancy is prolonged.

One aspect of an embodiment of the present disclosure includes wherein the apelin receptor agonist is dosed as an aerosol.

One aspect of an embodiment of the present disclosure includes wherein the apelin receptor agonist is dosed systemically.

One aspect of an embodiment of the present disclosure further comprises one or more additional agent. One aspect of an embodiment of the present disclosure includes wherein the additional agent is one or more of perfenidone, nintedinib, one or more corticosteroids, and one or more antibiotics.

One aspect of an embodiment of the present disclosure includes wherein the mean survival time of the patient is improved.

One aspect of any one of the embodiments and aspects of the present disclosure includes where the method of the present disclosure is used to treat one or more of asthma, chronic obstructive pulmonary disease (COPD), bronchitis, emphysema, pulmonary edema, acute respiratory disease syndrome (ARDS), interstitial lung disease, sarcoidosis, co-morbid pulmonary disorder, an autoimmune condition, rheumatoid arthritis, vascular leak syndrome including Clarkson Disease, pulmonary veno-occlusive disorder (PVOD), and scleroderma.

The scope of the present invention includes all combinations of aspects, embodiments, and preferences herein described.

DETAILED DESCRIPTION OF THE INVENTION

Figure 1:
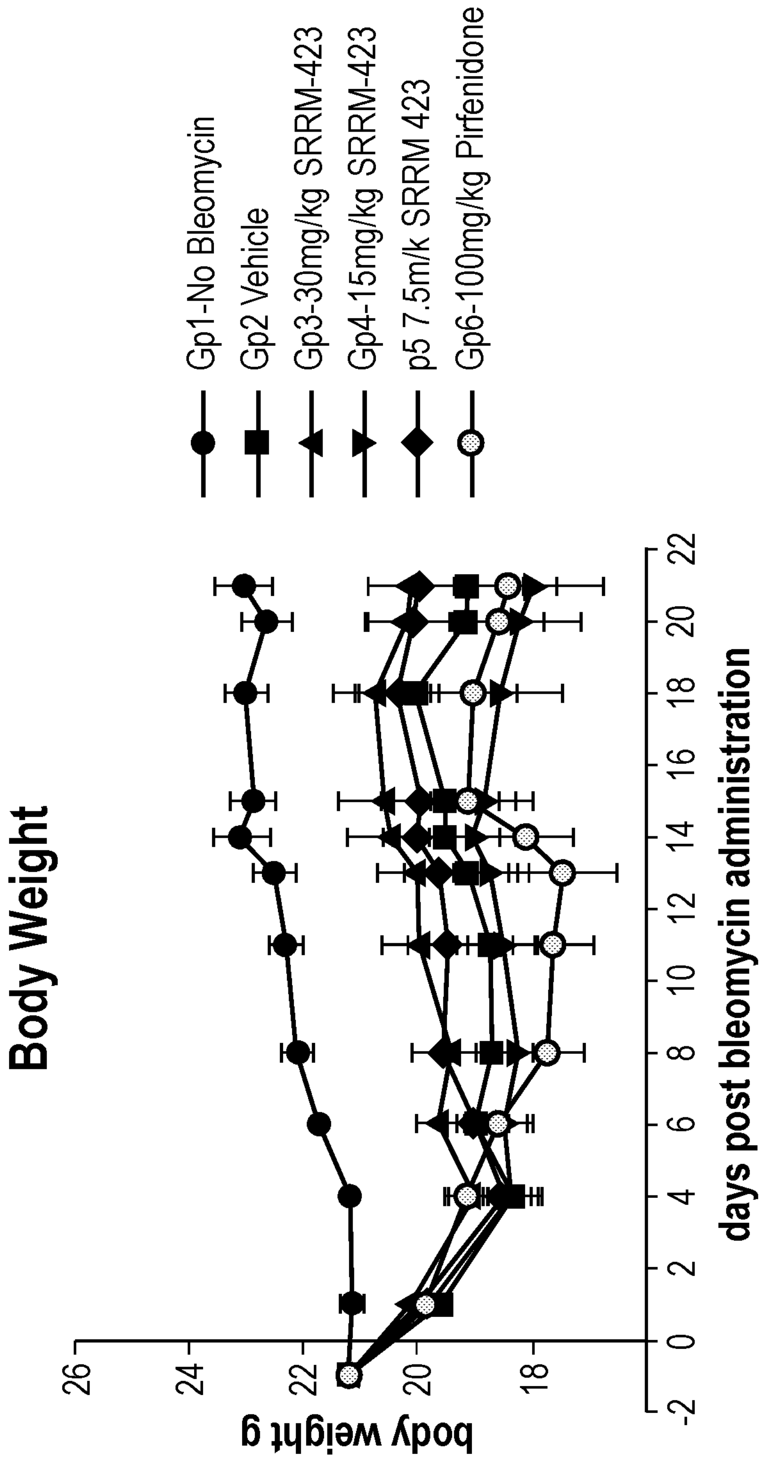
FIG. 1 illustrates average test animal body weight for each experimental group.
Figure 2A:
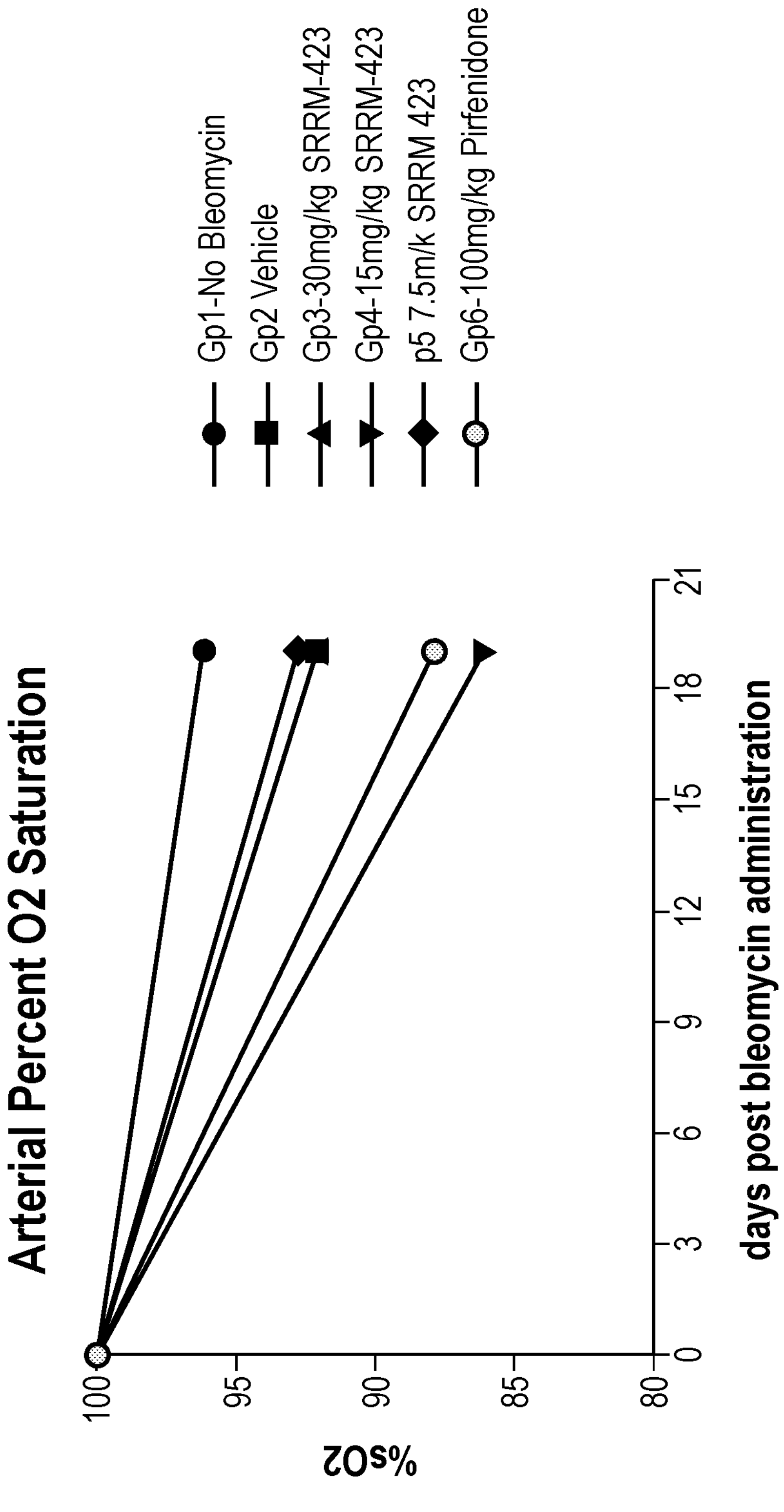
FIGS. 2A and 2B illustrate hypoxia data for each experimental group.
Figure 2B:
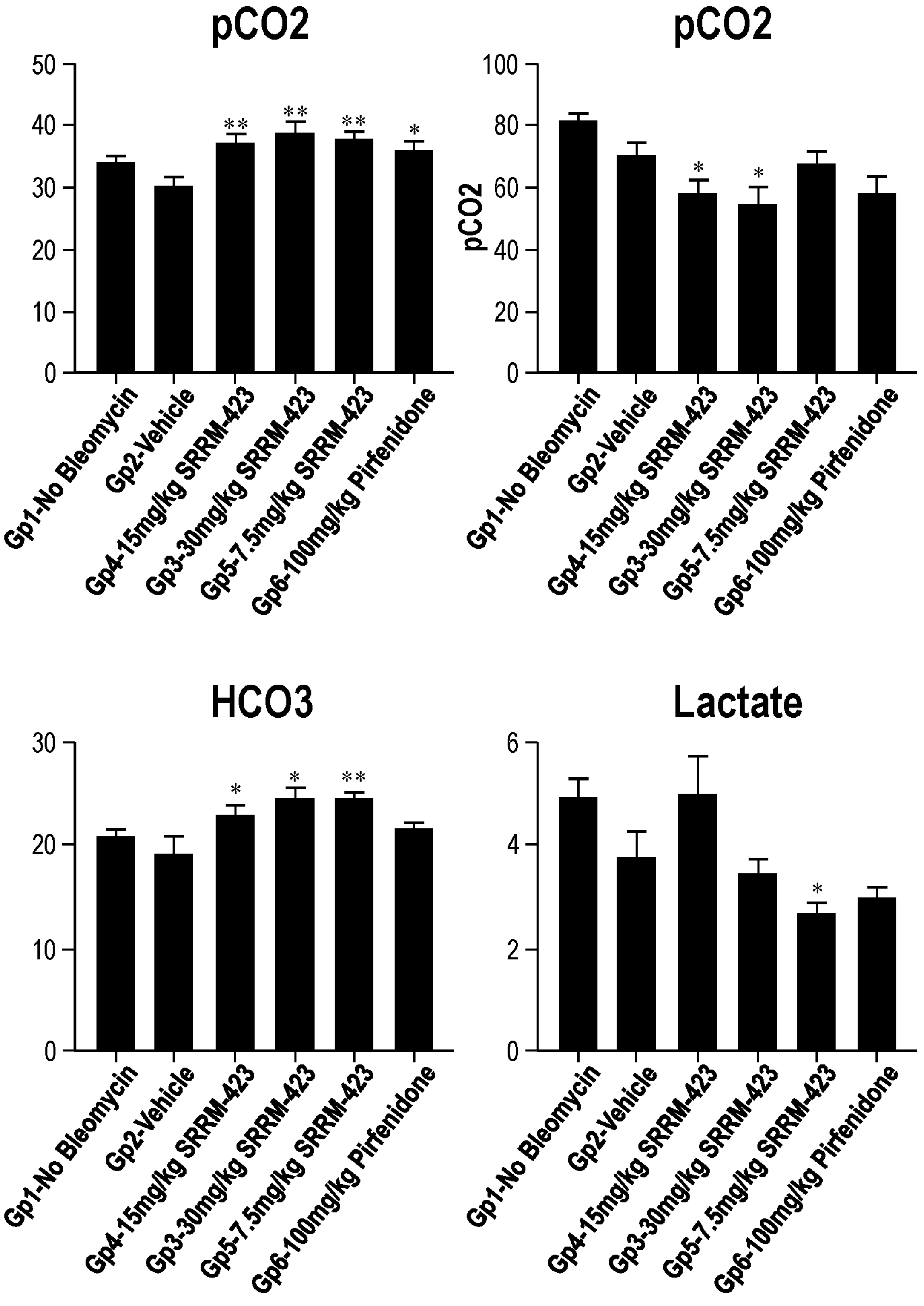

Apelin receptors are widely expressed in endothelial cell lining lung capillaries and vessels. IPF, which is believed to be cause by prolonged airway insult, leads to basement membrane degradation as endothelial cells are lost. As a result, fibroblasts proliferate, scar tissue is formed, and lung function is compromised. APJ agonists, which may block endothelial cell injury present a novel treatment strategy for IPF. APJ agonists are believed to either block endothelial cell injury or promote regeneration or both. Apelinergic systems are believed to facilitate post-injury vascular development through endothelial cell signaling. Reference is made to Hou, Exp Mol Pathol (2017), 103, 203; Azizi, Eur J Pharmacol (2015), 761, 101; and Lathen, Circulation (2014), 130, 1179, each of which is incorporated by reference with regard to background teaching of IPF etiology. Apelinergic system activation may preserve lung architecture and promote vascular regeneration in IPF.

Compounds useful as APJ agonists are described in international patent applications PCT/US2015/034427, which published as WO 2015/188073, PCT/US2016/065808, which published as WO 2017/100558, and PCT/US2017/056117, which published as WO 2018/071526. Each of these applications is incorporated herein by reference in their entirety.

As used herein, the term "effective amount" means that amount of a compound that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound, as well as salts or solvates thereof, may be administered as the raw chemical. Additionally, the active ingredient may be presented as a pharmaceutical composition.

Accordingly, the invention further provides pharmaceutical compositions that include effective amounts of one or more compounds, or a salt or solvate thereof, and one or more pharmaceutically acceptable carriers, diluents, or excipients. The carrier(s), diluent(s), or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

The therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 0.1 to 20 mg/kg body weight per day. Thus, for a 70 kg adult mammal one example of an actual amount per day would usually be from 10 to 2000 mg. This amount may be given in a single dose per day or in a number (such as two, three, four, five, or more) of sub-doses per day such that the total daily dose is the same. An effective amount of a salt or solvate thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose. Such a unit may contain, as a non-limiting example, 1 mg to 2 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. In addition, pharmaceutical formulations may be used to allow delayed or extended exposure to compound of formula (I) under circumstances where delayed or extended exposure would improve therapy.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

Pharmaceutical formulations adapted for topical administration in the mouth include lozenges, pastilles, and mouthwashes.

A compound of the present invention or a salt or solvate thereof, may be employed alone or in combination with other therapeutic agents. The compound of formula (I) and the other pharmaceutically active agent(s) may be administered together or separately and, when administered separately, administration may occur simultaneously or sequentially, in any order. The amounts of the compound of formula (I) and the other pharmaceutically active agent(s) and the relative timings of administration will be selected in order to achieve the desired combined therapeutic effect. The administration in combination of a compound of formula (I) or a salt or solvate thereof with other treatment agents may be in combination by administration concomitantly in: (1) a unitary pharmaceutical composition including a combination of compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Those skilled in the art of organic synthesis will appreciate that there exist multiple means of producing compounds of the present invention, which are labeled with a radioisotope appropriate to various uses.

EXAMPLES

Example 1: Non-GLP Evaluation of Prophylactic Efficacy of Compound 1 in a 21-Day Bleomycin-Induced Lung Fibrosis Model in Male C57B/L6 Mice Bleomycin is widely used to induce pulmonary fibrosis in rodents in order to study potential novel therapies for fibrosis. This study was designed to evaluate the prophylactic efficacy of test compound, Compound 1, also referred to as SRRM-423, in a 21-day model of bleomycin-induced pulmonary fibrosis in male C57BL/6 mice.

Prophylactic treatment of three different doses of 30 mg/kg, 15 mg/kg, and 7.5 mg/kg of Compound 1 was commenced a day before induction of disease and continued until the end of the study, namely 21 days after bleomycin administration. Treatment was administered twice daily via oral gavage.

Overall, test compound Compound 1 showed positive impact on one or more end-point readouts for fibrosis that were evaluated in the study. Prophylactic treatment with Compound 1 twice daily improved the overt symptoms associated with bleomycin administration in this 21-day non-GLP study. Compound 1 at 30 mg/kg appeared somewhat more effective. The administration of test compound reduced absolute and normalized lung weights, and decreased total number of leukocytes from bronchoalveolar lavage (BAL) fluid.

The objective of this non-GLP study was to evaluate the prophylactic efficacy of Compound 1 in a 21-day model of bleomycin-induced pulmonary fibrosis in mice.

Materials and Methods

Mice were administered bleomycin (Catalog number C-61703-323-22, lot number D011495AA, Hospira) via oropharyngeal route to induce lung fibrosis.

Bleomycin-induced animals were treated twice daily with either of the three different doses of test compound Compound 1 or pirfenidone starting from a day prior to disease induction and continued till study termination. Study animals were harvested on day 21 post-bleomycin administration. As an end point analysis, fibrosis symptoms such as body weight, absolute lung weight, lung weight normalized to body weight, and total leukocytes in BAL fluid were evaluated and compared with vehicle-treated mice.

Study Animals

One week prior to study initiation, 75 male C57BL/6 mice, six to eight weeks of age were obtained from Simonsen Laboratories (Gilroy, CA). Animals were weighed prior to study initiation and 60 animals were randomized into groups such that mean body weights were similar for the different groups. Remaining animals with lower or higher body weight were not included into the study. Food and water was provided ad libitum, with a light/dark cycle of 12 hours.

Study Design

A summary of study design is shown in Table 1:

TABLE 1

| Gp# | # Mice | Bleomycin | Treatment BID (Day −1 to 21 days post-bleomycin) | Termination Activities Day 21 post Bleomycin |
|---|---|---|---|---|
| 1 | 10 | None/Saline | Vehicle | Body weights and lung weights. |
| 2 | 10 | 1.5 U/kg Bleomycin | Vehicle | BAL fluid harvest, |
| 3 | 10 | 1.5 U/kg Bleomycin | Compound 1 30 mg/kg/dose | BAL leukocytes processed, counted. |
| 4 | 10 | 1.5 U/kg Bleomycin | Compound 1 15 mg/kg/dose | Lungs inflated (fixed in 10% NBF) |
| 5 | 10 | 1.5 U/kg Bleomycin | Compound 1 7.5 mg/kg/dose | Plasma from terminal bleed. |
| 6 | 10 | 1.5 U/kg Bleomycin | Pirfenidone (100 mg/kg/dose) | |

On day 0, all mice in groups 2-6 received a 1.5 U/kg oropharyngeal administration of bleomycin to induce pulmonary fibrosis. Animals in group 1 were not administered bleomycin, but instead received a single dose of normal saline via the oropharyngeal route, and were considered sham control mice.

Dosing was initiated one day prior to induction of disease. Animals were dosed twice daily orally with Compound 1 and Pirfenidone and treatment was continued until 21 days after bleomycin administration. Animals from group 2 were treated with vehicle (0.5% methylcellulose). Animals in groups 3, 4 and 5 received Compound 1 at 30, 15, and 7.5 mg/kg respectively, and animals in group 6 received Pirfenidone 100 mg/kg.

On day 19 post bleomycin administration, hypoxia related analytical parameters such as Partial Oxygen ($PO_2$), Partial Carbon Dioxide ($CO_2$), and Saturated Oxygen ($SO_2$), were evaluated.

Surviving animals were euthanized 21 days post bleomycin administration. Animals were weighed, then blood and lungs were collected. Blood was processed for plasma. Lungs, were weighed, flushed with HBSS for BAL collection, and fixed in 10% NBF. Supernatant from BAL fluid was frozen while the pellet was used for total leukocyte cell count.

Clinical Observations and Body Weights

Individual animals were monitored daily for clinical observations of pulmonary fibrosis, including general activity levels and morbidity.

Body weights were recorded three times a week during the study period. Body weights are shown in FIG. 1.

Bleomycin-Induced Pulmonary Fibrosis

In order to induce pulmonary fibrosis, mice in groups 2-6 were administered 1.5 U/kg bleomycin (Catalog number C-61703-323-22, lot number D011495AA, Hospira) in 70 µl via oropharyngeal administration. Animals from group 1 were administered 70 µl of saline by the oropharyngeal route, instead of bleomycin, and served as sham controls.

Bleomycin (15 U) from a sealed bottle was re-suspended in 1 ml of PBS. A fresh stock solution of 15 U/ml was used and diluted in PBS to prepare a dose of 1.5 U/kg in a 70 µl volume for each mouse. The method for instilling bleomycin in mice is described in Current Protocols in Pharmacology: 5.46.1, entitled "Mouse Models of Bleomycin-induced Pulmonary Fibrosis", incorporated herein by reference with regard to such teaching. Briefly, mice were anesthetized with Isoflurane inhalant anesthesia. The animal was then suspended on its back at a ~60° angle with a rubber band running under the upper incisors on an inclined surface (Biolite RIS-100, small animal intubation system, Braintree Scientific, Braintree, MA). The airway was opened while securing the tongue, which was held with padded forceps. Seventy µl of bleomycin was then administered into the back of the oral cavity with a syringe using a blunt needle. The animal's tongue and mouth were held open until the liquid disappeared from the oral cavity. The animal was then returned to its cage and monitored until fully recovered from the anesthesia.

Compound or Vehicle Formulations

Compound 1 was provided as a trifluoroacetic acid (TFA) salt and requires a salt correction of 1.0654. All dose amounts were calculated as the free base content of the test article using the correction factor. Vehicle used for formulation of test compound, Compound 1, was 0.3% Tween 80 and 1% N-methylpyrollidinone in 0.5% aqueous methylcellulose. Vehicle and dosing formulation of Compound 1 was prepared fresh weekly. Dosing formulations and vehicles were stored at 4±2° C. protected from heat and light. The expiration date for the test article dosing solutions were set at 7 days after preparation. Pirfenidone was sourced from a vendor and formulated in the same vehicle as Compound 1, i.e., 0.3% Tween 80 and 1% N-methylpyrollidinone in 0.5% aqueous methylcellulose.

Animals were dosed twice daily with volume of 100 µl/dose by oral gavage from a day prior to disease induction and same treatment was continued till study termination, i.e., day 21 post bleomycin administration. Surviving animals were harvested within 2 to 4 hours post final dosing on day 21.

Harvest Procedures and Blood Collection

The study was terminated on day 21-post bleomycin administration. Animals were harvested starting from group 1 to group 6 in serial order. Treated animals were harvested ~2 to 4 hours after final dose and the time of harvest was recorded. Upon study termination on day 21, study animals were anesthetized with isoflurane inhalant anesthesia and terminal cardiac blood was collected from each animal using a 1 ml syringe with a 25-gauge ⅝" needle. Promptly following collection, blood was transferred to EDTA tubes (BD Biosciences) and plasma was separated by centrifugation at 1,300 g for 10 minutes at 4° C., stored at −80° C. Death was ensured by cervical dislocation. Plasma was separated by centrifugation, transferred label tube and stored at −80° C. The internal organs of each animal were exposed and observed for abnormalities.

The lungs from each animal were harvested following Aragen's Standard Operating Procedure (WA-004-01). Each lung was dissected from the animal and weighed. The BAL fluid was collected by lavaging the lung twice with 0.5 ml Hanks Balanced Salt Solution (HBSS, VWR Radnor, PA). After collection of BAL fluid, whole lungs were inflated with 10% neutral buffered formalin (NBF), fixed in 10% NBF, and shipped to Seventh Wave, Missouri, for histopathology.

BAL Fluid Collection and BAL Cell Count

After collection, the BAL fluid from each mouse was centrifuged at 1,000 rpm at 4° C. for 5 minutes. The BAL fluid supernatant was transferred into three separate tubes with aliquots of 200 µl aliquots each, snap frozen on dry ice, and stored at −80° C. The BAL cell pellets were then re-suspended in 2 mL of 1× PharmaLyse buffer (BD Biosciences, San Jose, CA) to lyse RBCs. PBS supplemented with 2% FBS was added to stop further cell lysis. The BAL cells were again centrifuged and suspended in 250 µl of PBS. Viable cells were counted using a hemocytometer and trypan blue staining and recorded for each mouse.

Statistical Analysis

Endpoint data on day 21 is shown per experimental group, with standard error of the mean (SEM). Statistical differences (defined as $p<0.05$) between groups were analyzed using t-tests in Prism version 7.0 software (GraphPad, La Jolla, CA). Groups treated with Compound 1 and Pirfenidone were compared to bleomycin-instilled vehicle control treated mice.

Results

Clinical Observations and Body Weights

Bleomycin administration induced several changes in the animals that are consistent with the induction of pulmonary fibrosis. Few animals did not tolerate the treatment, and one animal each from groups 2, 3, and 5 and two animals each from group 4 and 6 succumbed to disease.

The body weights of all study animals were recorded three times a week from the day prior to bleomycin exposure and continued until the end of the study on day 21. Animals treated in group 4 (Compound 1 at 15 mg/kg) lost more weight compared to other groups. Sham control animals showed no weight lost and gained weight throughout the study. FIG. 1 shows the average animal body weights for each experimental group throughout the study.

Lung Weights

Figure 3A:
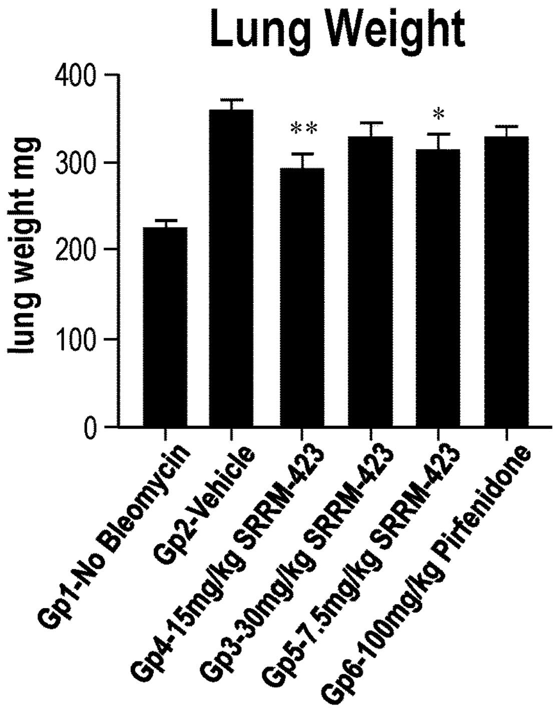
FIGS. 3A and 3B, respectively illustrate: (3a) the average absolute lung weights for each experimental group; and (3b) the lung weights normalized to animal body weight.
Figure 3B:
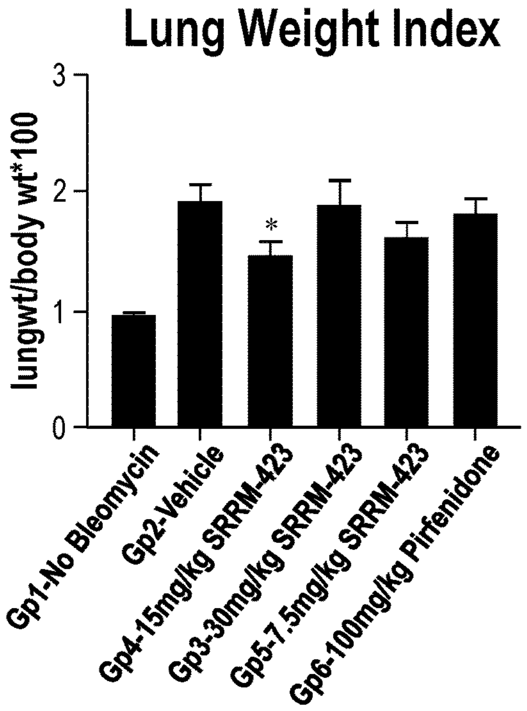

FIG. 3*a* shows the average absolute lung weights for each experimental group and FIG. 3*b* shows the lung weights normalized to animal body weight. Bleomycin administration led to an increase in lung weight when compared to non-bleomycin sham controls, impacting both absolute lung weight as well as lung weight normalized to animal body weight ($p<0.0001$ t test).

The highest average lung weights 355 mg±11.38 was observed in bleomycin induced vehicle treated group 2. Treatment of the test compounds showed lower lung weight in bleomycin administrated animals. Absolute lung weights 92.12% of 310 mg±13.17 in group 3 animals treated with 30 mg/kg Compound 1, and 313 mg±14.46 in group 5 treated animals with 7.5 mg/kg in Compound 1 was recorded, which were significantly lower compared to vehicle treated control animals ($p<0.05$). Statistical significance was not reached in group 4 treated with 15 mg/kg Compound 1 and group 6 animals treated with Pirfenidone. A similar trend was observed on lung weight normalized with body weight of animal. Lung weights, absolute and normalized, for mice in each experimental group were recorded.

Bronchoalveolar Lavage (BAL) Fluid Analysis

Figure 4:
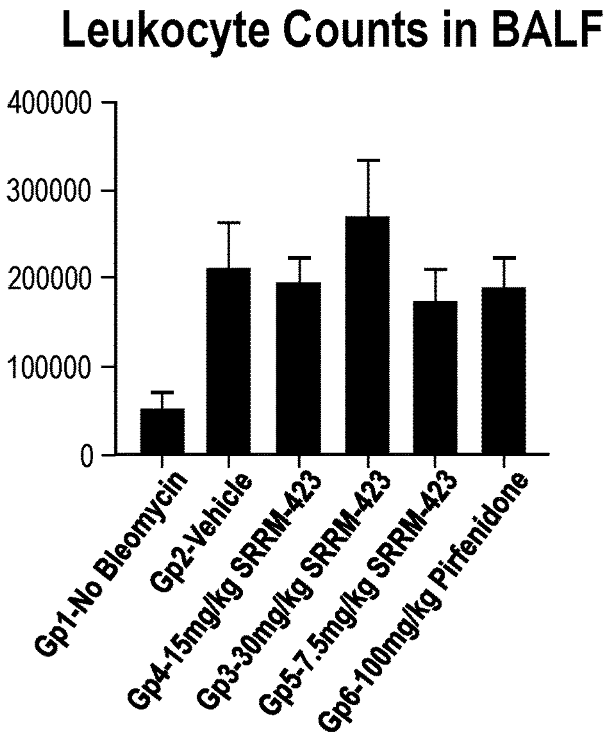
FIG. 4 illustrates the average total leukocyte cell counts recovered in the bronchoalveolar lavage fluid.

FIG. 4 shows the average total leukocyte cell counts recovered in the BAL fluid.

Total viable leukocyte counts increased in bleomycin-administered control group 2 (21,2000±50000) when compared to the sham control group 1 animals (52,250±52000) ($p<0.0001$).

In comparison to the vehicle-treated group 2, administration of Compound 1 compound reduced the average leukocyte count in BAL fluid in all test groups. Statistical significant was not reached any of the treatment group. BAL cell counts in each experimental group is shown in Appendix 4 but a trend towards reduced inflammation was observed.

Figure 15A:
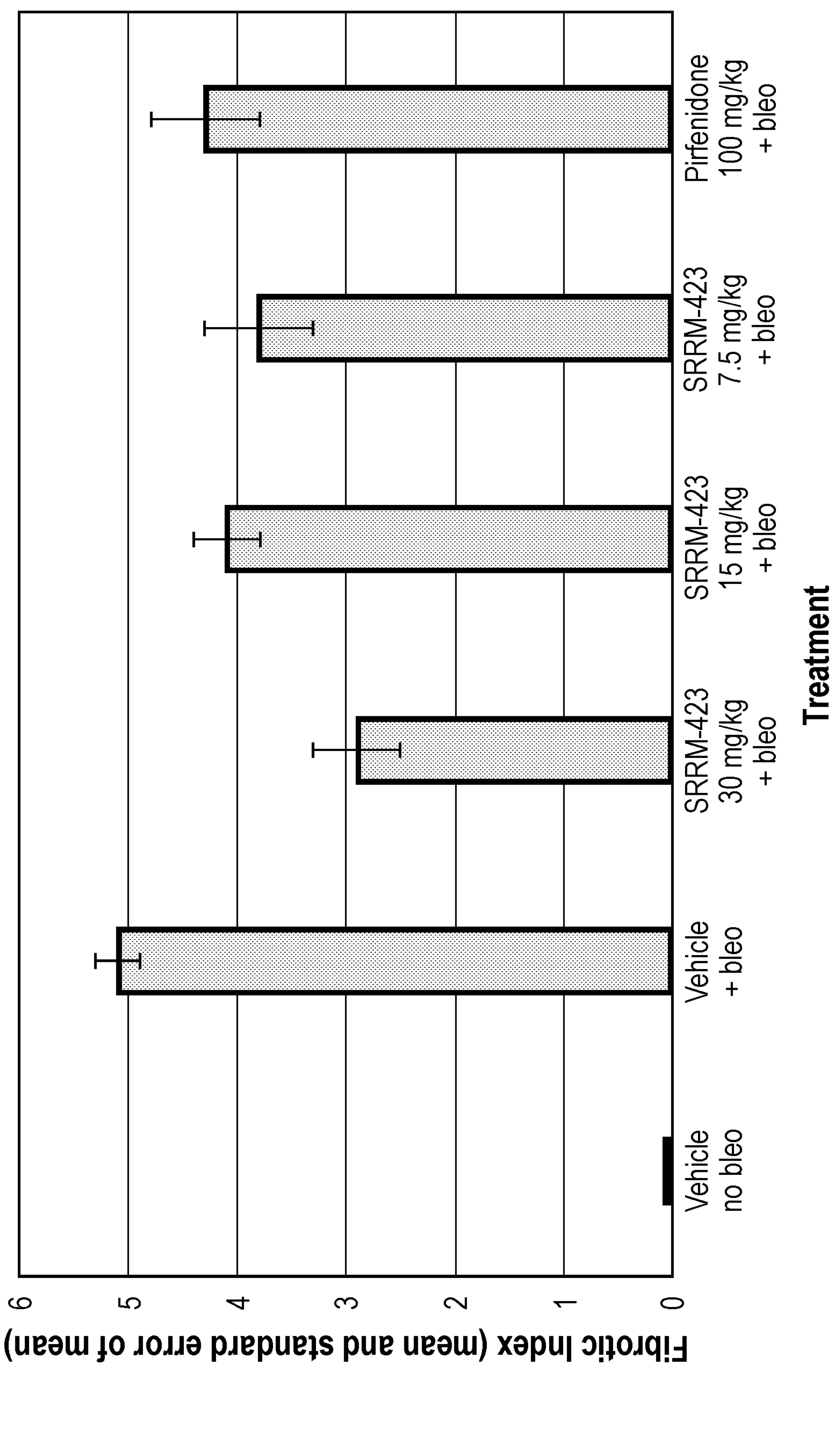
FIG. 15A is a graphical representation of histopathology results illustrating an Ashcroft mean fibrotic index for the test compound demonstrating substantial decrease in fibrosis.

FIG. 15A shows that treatment with compound 1 also reduced proliferation of activated myofibroblasts as assessed using an antibody to α-SMA, which is a marker of myofibroblast proliferation. Lung injury and fibrosis are quantified by a certified pathologist and given a score called an Ashcroft Score [T. Ashcroft et al. J Clin Pathol. 1988 April; 41(4): 467-470, herein incorporated by reference with regard to such scoring]. Compound 1 reduced Ashcroft score index along with Pirfenidone as indicated in FIG. 15A showing improvement of lung histology and reduced damage caused by bleomycin treatment.

Thus, administration of compound 1 twice daily resulted in substantially less fibrosis in the lungs of mice following bleomycin induction, compared to induced controls. According to the Ashcroft scores, administration of 30 mg/kg compound 1 twice daily resulted in the greatest reduction in fibrosis compared to induced controls and a substantial reduction in fibrosis compared to bleomycin-induced mice treated with 100 mg/kg Pirfenidone twice daily. Administration of 15 or 7.5 mg/kg of compound 1 resulted in substantially less fibrosis following bleomycin induction compared to induced controls, however the reduction in fibrosis was not as great as when 30 mg/kg was administered, and was similar compared to BID administration of 100 mg/kg Pirfenidone.

Figure 15B:
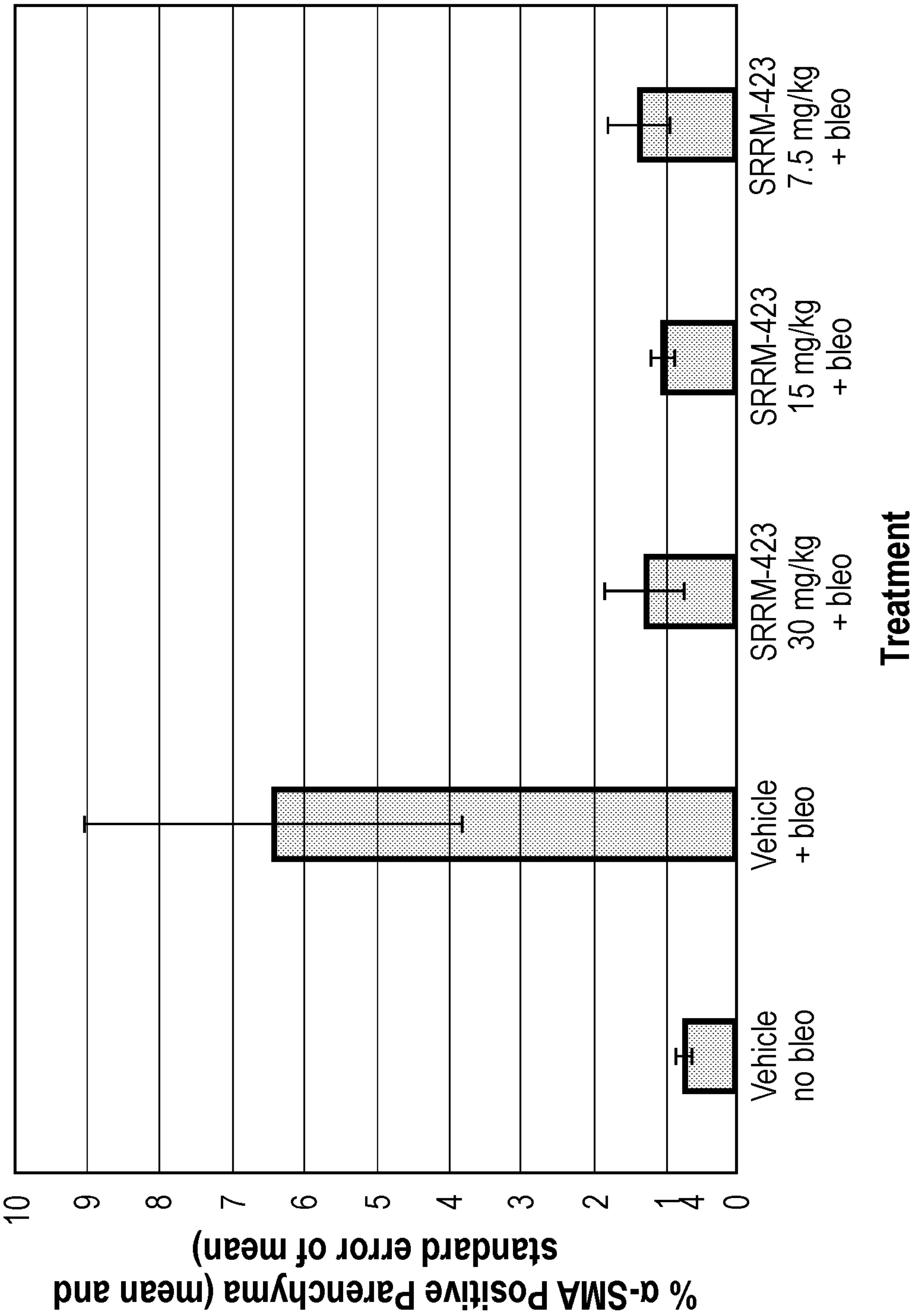
FIG. 15B is a graphical representation of a group mean percentage of α-SMA positive parenchyma tissue demonstrating that animals treated with test compound had substantially less α-SMA positive lung tissue as a percent of the total lung parenchyma compared to tissue controls.

As shown in FIG. 15B Induction with bleomycin resulted in substantial increases in the percent of α-SMA positive lung tissue. Animals treated with >7.5 mg/kg of compound 1 had substantially less α-SMA positive lung tissue as a percent of the total lung parenchyma compared to induced controls, with no clear relationship to the dose.

Conclusions

The study was performed to evaluate the prophylactic efficacy of test compounds, such as Compound 1, in a 21-day model of bleomycin-induced pulmonary fibrosis in mice.

The prophylactic treatment of Compound 1 at 3 different concentrations (30 mg/kg, 15 mg/kg and 7.5 mg/kg) began one day prior to bleomycin administration and continued until study termination, i.e. 21 days after bleomycin administration as described in the study design above and with reference to Table 1. At the termination of the study, end point analysis of pulmonary fibrosis parameters were evaluated.

Bleomycin administration induced several changes in the animals that are consistent with the induction of pulmonary fibrosis. Bleomycin administration resulted in weight loss, increased absolute and normalized lung weights and increase in total leukocyte counts in group 2 control animals related to sham control animals ($p<0.0001$).

Overall, animals treated with prophylactic administrations of test compound showed positive impact on in-life parameters that typically resulted in fibrosis in bleomycin administered lungs. The highest dose of 30 mg/kg of Compound 1 significantly ameliorated fibrosis symptoms and showed improvement on different parameters evaluated in the present study such as body weight, lung weight, lung weight index, total leukocyte counts and myofibroblast proliferation.

Example 2: Histomorphologic Review of Sections of Liver, Heart, Lung, and Brain from the Apelin Knockout Mouse Model for Beta-Galactosidase Staining

Objective

Sections of liver, heart, lung, and brain were reviewed for beta-galactosidase staining. Associated images were collected and are herein provided.

Materials and Methods

A total of 25 slides were received for evaluation that consisted of six sections of brain (5 and 10 m); six sections of heart (5 and 10 m); six sections of liver (5 and 10 μm); and seven section of lung (5, 10, and 20 μm). To optimize the location, frequency, and intensity of beta galactosidase staining, the 10 m section of each tissue was elected for examination.

Results

As shown in FIGS. 5-14, positive beta galactosidase staining was definitively observed. Positive staining was observed in the myocardial interstitium, gallbladder lamina propria, and alveolar walls of study animals. There was occasional (albeit less consistent) staining of cardiac myocyte nuclei.

Figure 5:
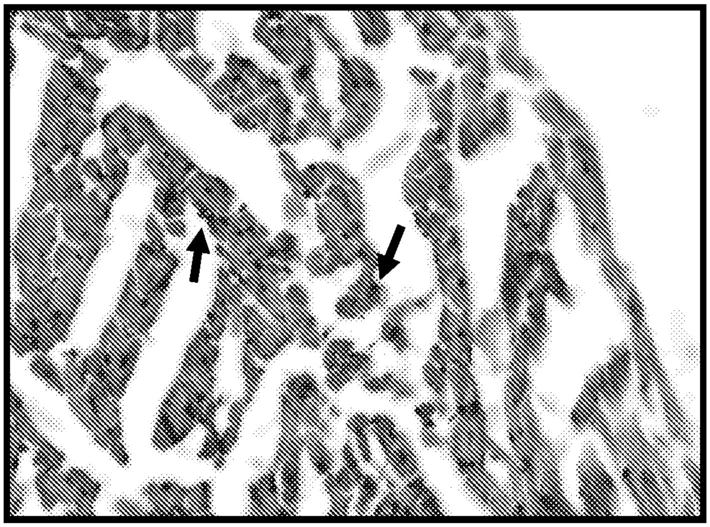
FIG. 5 illustrates sections of test animal heart tissue with positive staining in interstitial tissue, likely representing endothelial cells.

More specifically, FIG. 5 illustrates sections of test animal heart tissue with scant to moderate amounts of positive staining in the right ventricle, intraventricular septum, and apex. Staining appears most prominently around nuclei (perinuclear) in the interstitium between cardiac myofibers. Some of these mesenchymal cells may represent endothelial cells. There appeared to be occasional perinuclear staining within cardiac myocytes, however, it was less intense and definitive (image not provided).

Figure 6:
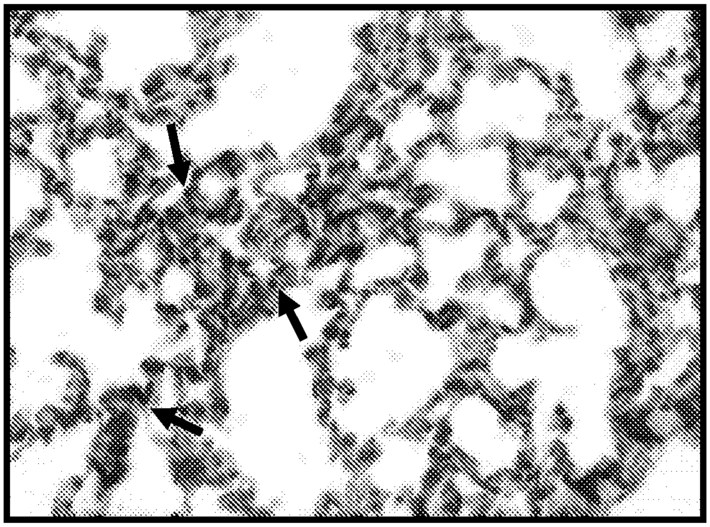
FIG. 6 illustrates sections of test animal lung tissue with positive staining in alveolar walls.

FIG. 6 illustrates sections of test animal lung tissue with patchy, moderate staining in alveolar walls. Cellular distribution (endothelium vs. epithelium) within alveoli was difficult to determine due to tissue folding resulting from sectioning.

Figure 7:
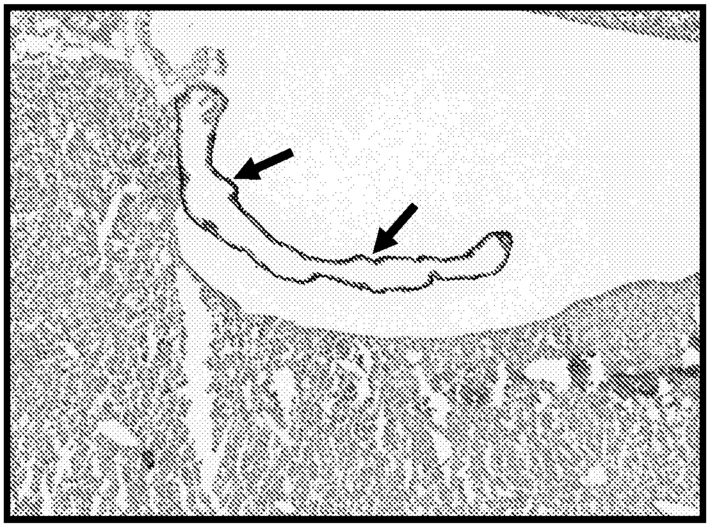
FIG. 7 illustrates sections of test animal liver tissue with positive staining of the gallbladder. Hepatocytes are unstained.
Figure 8:
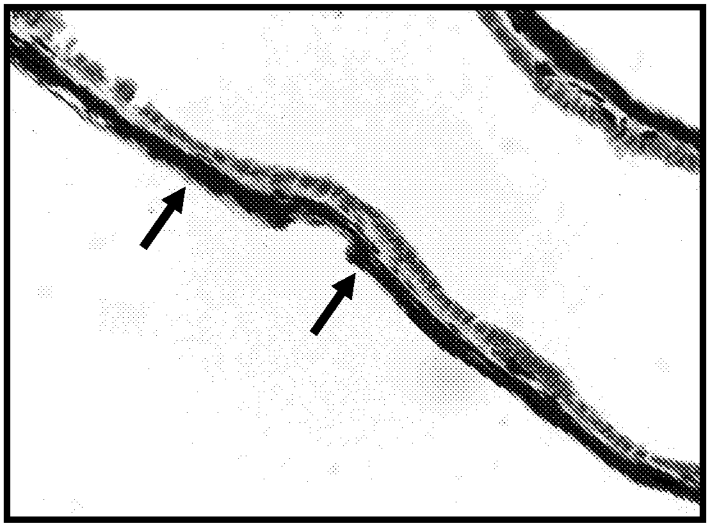
FIG. 8 illustrates sections of test animal liver tissue (40×, higher magnification) showing positive staining of the gallbladder lamina propria.

FIGS. 7 and 8 illustrate sections of test animal liver tissue with intense staining in the lamina propria of the gallbladder. Other cells and structures of the liver were unstained.

Figure 9:
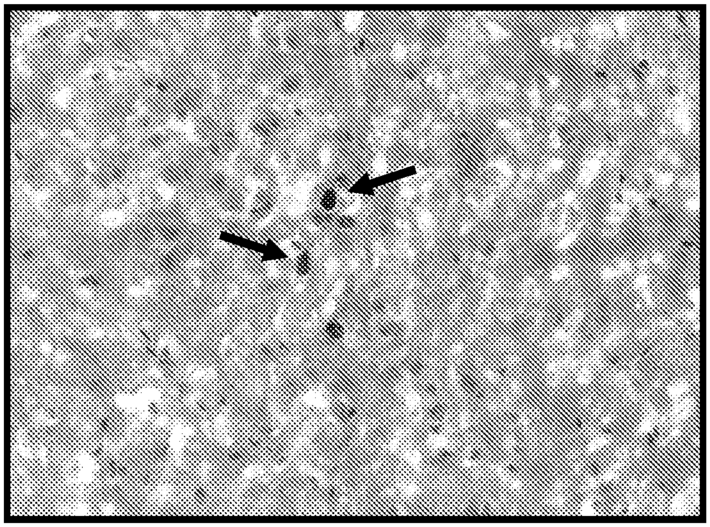
FIG. 9 illustrates sections of test animal brain tissue with positive nuclear staining in a small aggregate of nuclei of cerebrocortical cells of unknown identity.

FIG. 9 illustrates sections of test animal brain tissue with a small aggregate of nuclear staining in the cerebral cortex; significance undetermined. There was also abundant non-specific staining in the brain stem (image not provided).

Figure 10:
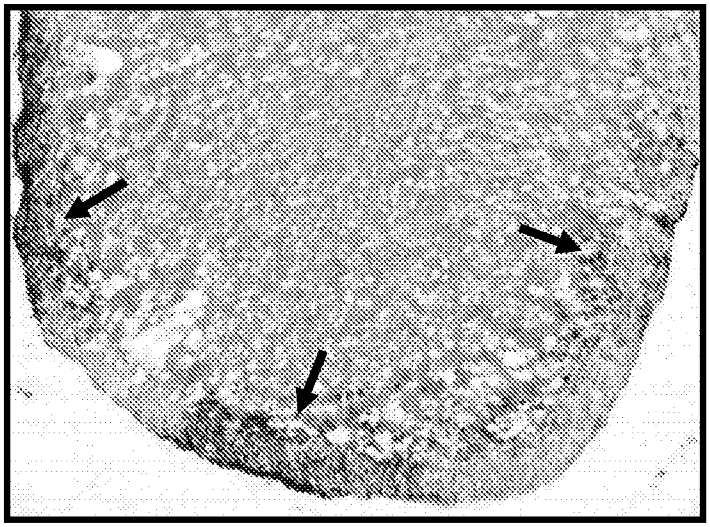
FIG. 10 illustrates sections of test animal brain tissue with nonspecific staining involving the brain stem.

FIG. 10 illustrates sections of test animal brain tissue with nonspecific staining in the brain stem.

Figure 11:
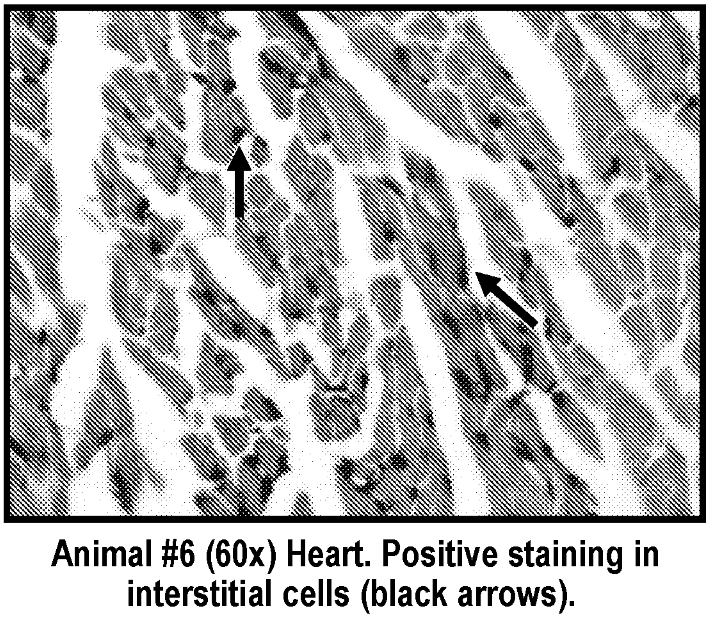
FIG. 11 illustrates sections of test animal heart tissue with positive staining in interstitial cells.
Figure 12:
FIG. 12 illustrates sections of test animal heart tissue with positive staining in nuclei of cardiac myocyte.

FIG. 11 illustrates sections of test animal heart tissue with moderate to intense positive staining of the interstitium in the right ventricle, left ventricle, intraventricular septum, and apex; less intense staining was observed in the atria. Some positive staining of mesenchymal cells may represent endothelial cells (FIG. 11). Positive staining of cardiac myocyte nuclei was occasional (FIG. 12).

Figure 13:
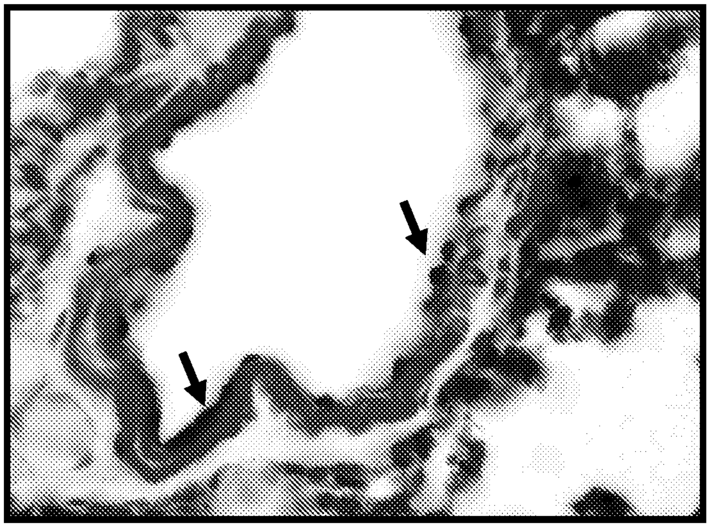
FIG. 13 illustrates sections of test animal lung tissue with positive staining in endothelial cells, namely lining a medium sized, thin walled blood vessel, likely a vein, shown with black arrows.

FIG. 13 illustrates sections of test animal lung tissue with scattered, moderate staining in alveolar walls; cellular distribution was difficult to determine (image not provided). There was definitive staining of endothelial cells lining thin walled blood vessels (likely veins).

Figure 14:
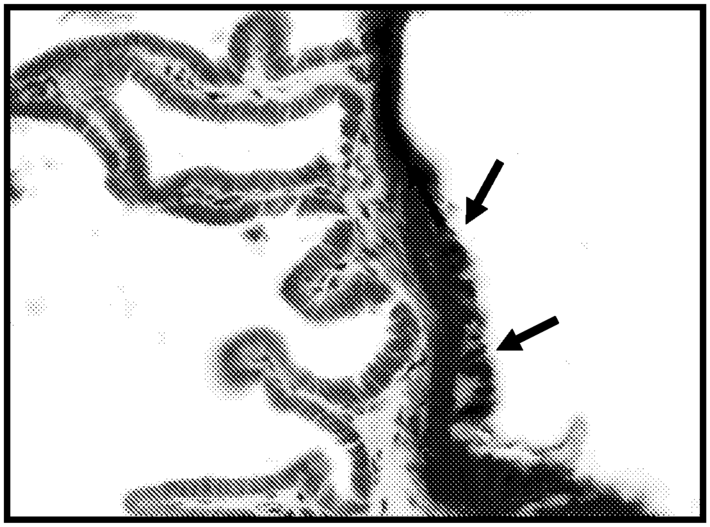
FIG. 14 illustrates sections of test animal gallbladder tissue with positive staining of the gallbladder lamina propria, shown with black arrows.

FIG. 14 illustrates sections of test animal liver tissue with scant staining in the lamina propria of the gallbladder. Other cells of the liver were unstained.

Figure 16:
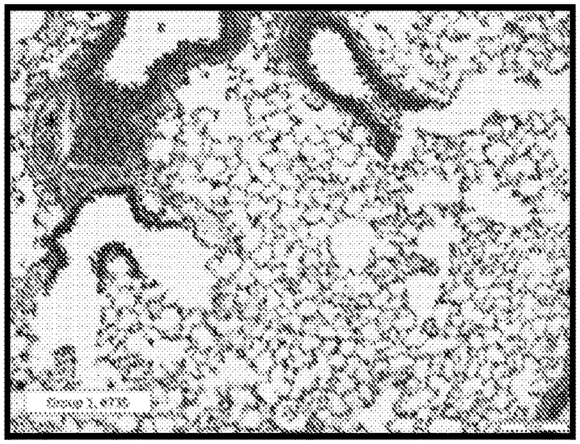
FIG. 16 illustrates that the compounds of the present disclosure, in a therapeutic dose, reduce collagen deposition in a bleomycin-induced male mouse IPF model (histopathology).
Figure 16:
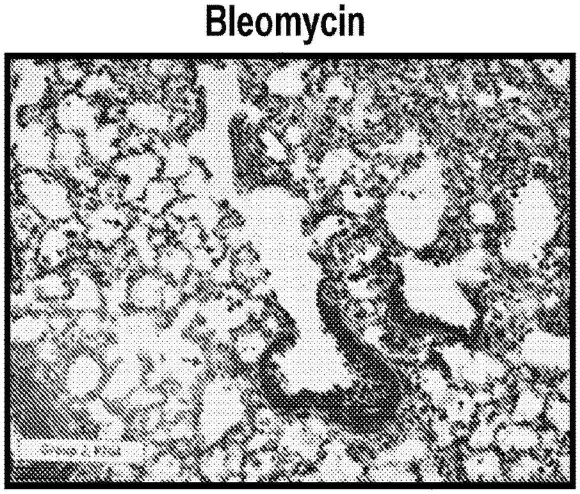
Figure 16:
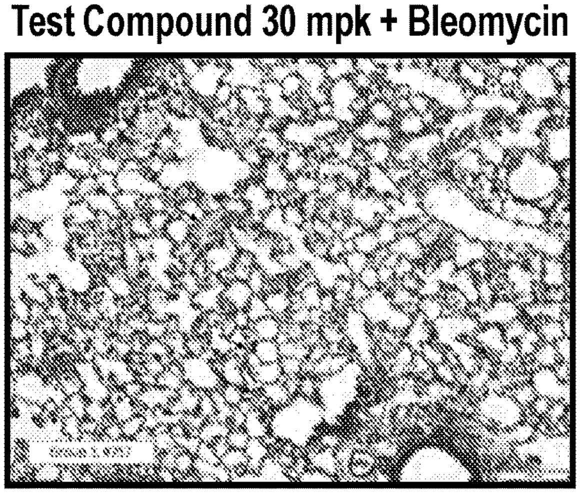

FIG. 16 illustrates that the compounds of the present disclosure, in a therapeutic dose, reduce collagen deposition in a bleomycin-induced male mouse IPF model (histopathology). Masson's trichome staining is widely used to study muscular pathologies/collagen fibers and muscle and keratin are contrast stained. In IPF patients, the collagen synthesis addresses injury of the lung epithelial cells, however, it is excessively stimulated resulting in abnormal fibrosis. The test compound shows influence in stopping the lung epithelial cells injury, when compared to the Bleo induced vehicle, as seen by limited observation of collagen deposition. As shown, the designation of Normal demonstrates positively staining collagen primarily surrounding bronchioles and blood vessels. The designation of Bleomycin/No Treatment demonstrates masses of fibrosis similar to an Ashcroft score of 5 (upper right side). Additionally, remaining alveolar septae are fibrotic (arrows). The designation of APT 30 mg mpk/+Bleomycin demonstrates that fibrosis is present, similar to an Ashcroft score of 2. Additionally, there is an area with marked thickening of the contiguous alveolar septae and knot-like formation.

Figure 17:
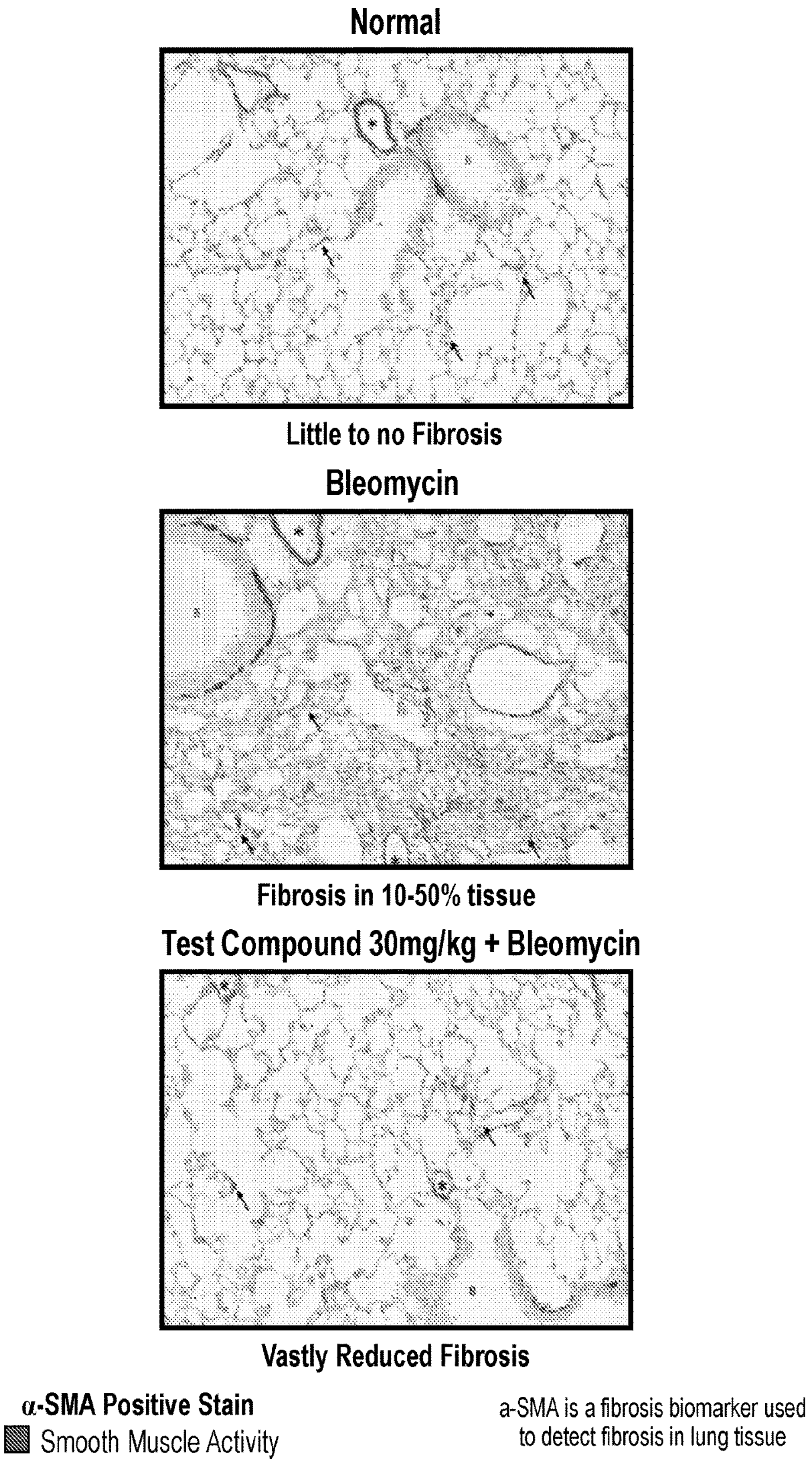
FIG. 17 illustrates that the compounds of the present disclosure, in a therapeutic dose, reduce fibrosis in a bleomycin-induced male mouse IPF model (histopathology).
Figure 18:
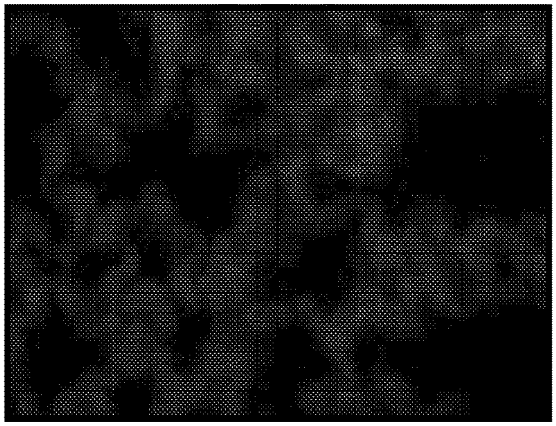
FIG. 18 illustrates that the compounds of the present disclosure, in a therapeutic dose, reduce apoptosis in a bleomycin-induced male mouse IPF model (histopathology).
Figure 18:
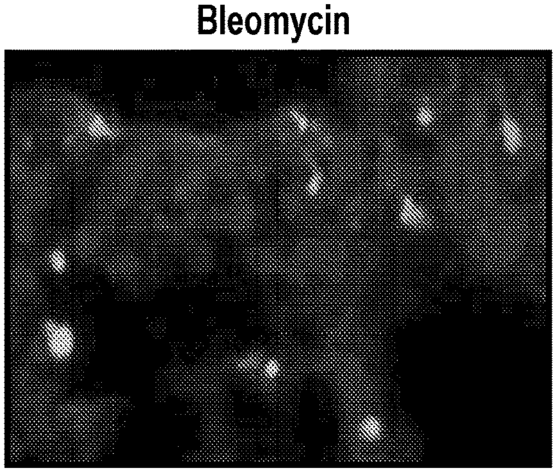
Figure 18:
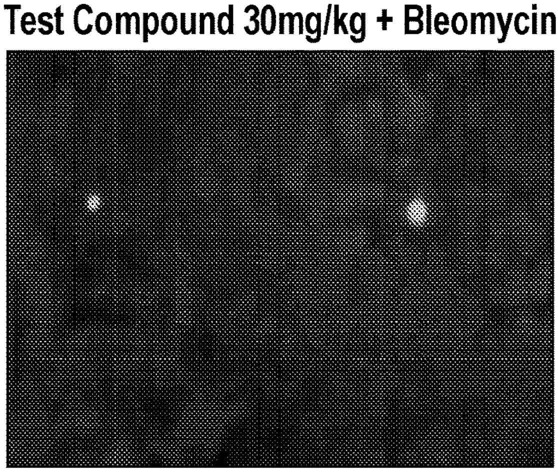
Figure 19:
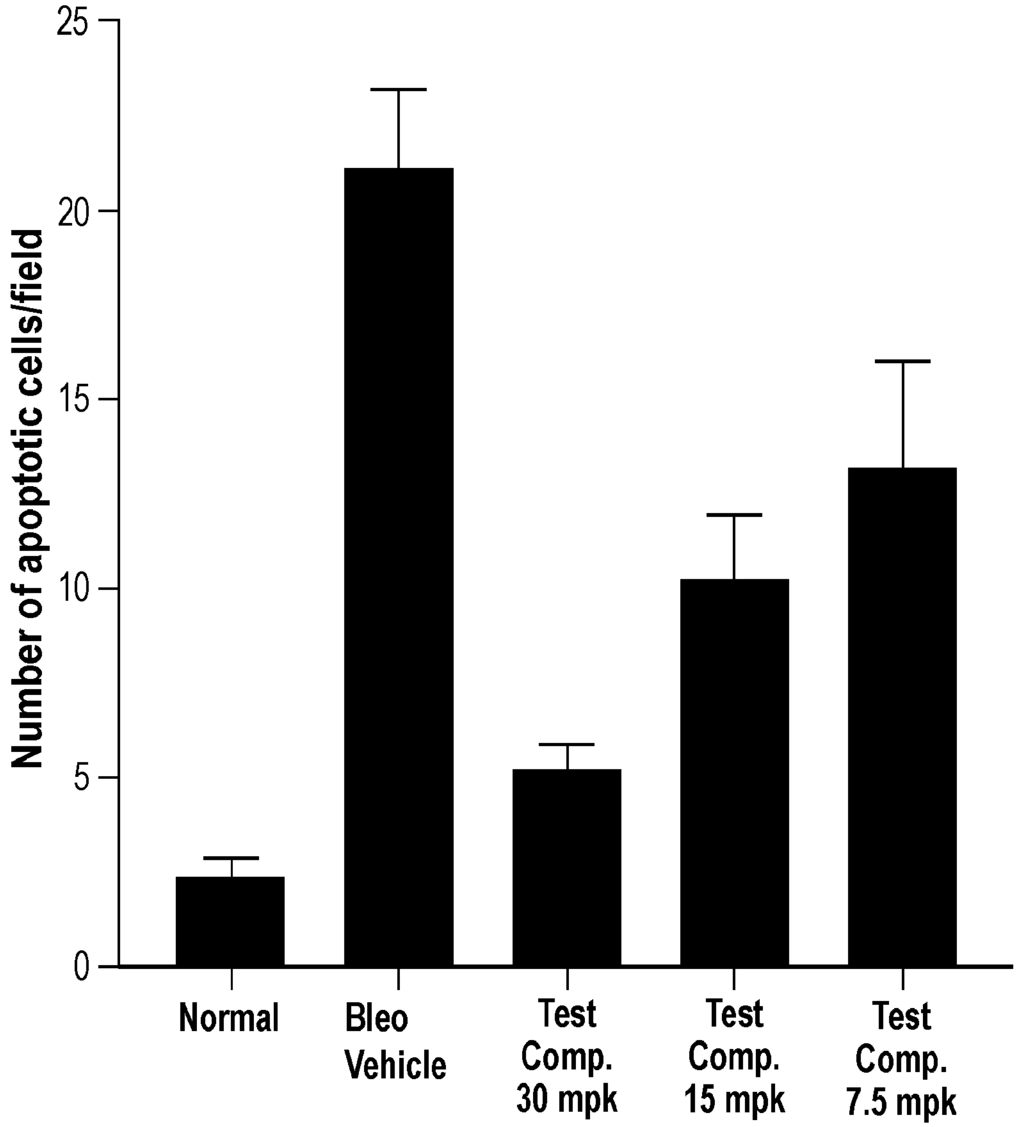
FIG. 19 is a graphical representation demonstrating the reduction is apoptotic cells as compared to a vehicle comparator.

FIG. 17 illustrates that the compounds of the present disclosure, in a therapeutic dose, reduce fibrosis in a bleomycin-induced male mouse IPF model (histopathology). The test compound is shown to be efficacious in preventing/limiting fibrosis formation, when compared to the bleomycin induced (lung injury) vehicle without treatment. The designation Normal demonstrates positive staining, primarily surrounding bronchioles (B) and blood vessels (asterisk). Smaller blood vessels (arrows) in the lung parenchyma account primarily for the low percentage of α-SMA recorded in normal lung. The designation Bleomycin demonstrates that there is a substantial increase in α-SMA positive staining corresponding to areas of fibrosis and within remaining alveolar septa (arrows). B=bronchiole, asterisk=blood vessel. The designation APT101 30 mpk+Bleomycin demonstrates that in addition to small blood vessels (asterisks) there is positive staining within alveolar septae (arrows) as well as scattered fibrotic areas (not pictured), but is substantially less compared to induced controls FIG. 18 illustrates that the compounds of the present disclosure, in a therapeutic dose, reduce apoptosis in a bleomycin-induced male mouse IPF model (histopathology). Apoptosis is observed in alveolar epithelial cells rather than fibroblasts, which is believed to be involved in IPF pathogenesis (reference is made to Cell Death Discovery, Vol 5, Article Number: 146, 2019, herein incorporated by reference with regard to such teaching). Both FIG. 18 (tunel stained) and FIG. 19 (graphical representation) show that the test compound reduced apoptosis as compared to the bleomycin vehicle. Apoptosis is a form of programmed cell death, or so-called cellular suicide. It is different from necrosis, in which cells die due to injury. Apoptosis is an orderly process in which the cell's contents are packaged into small packets of membrane for "garbage collection" by immune cells.

Definitive positive staining was not observed in one animal, other than a small aggregate of nuclei in the cerebral cortex. The significance of this finding remains undetermined.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A method for regenerating tissue damaged by idiopathic pulmonary fibrosis in a patient, comprising administering a therapeutically effective amount of an apelin receptor agonist, wherein the apelin receptor agonist is a compound of Formula B:

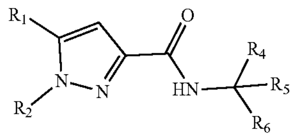

B or a pharmaceutically acceptable salt, a prodrug, or a salt of a prodrug, wherein $R_1$ is represented by the formula:

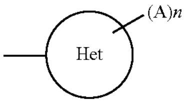

wherein

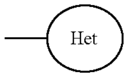

is a monocyclic aryl or heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $—CF_3$, $—(CH_2)_xNR_7R_8$, —CN, $—CONR_7R_8$, $—COR_7$, $—CO_2(CH_2)_xNR_7R_8$, $—CO_2R_7$, halogen, hydroxyl, $—N_3$, $—NHCOR_7$, $—NHSO_2C_{1-8}$ alkyl, $—NHCO_2C_{1-8}$ alkyl, $—NO_2$, $—NR_7R_8$, $—O(CH_2)_xNR_7R_8$, $—O(CH_2)_xCO_2R_7$, $—OCOC_{1-8}$ alkyl, $—OCO(CH_2)_xNR_7R_8$, $—SF_5$, $—SO_2NR_7R_8$, $—SO_{(1-3)}R_7$, $—SR_7$, or tetrazolone;

$R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, $—(CH_2)_xCONHR_9$, $—(CH_2)_xCOR_9$, $—(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups;

n is 1, 2, 3, 4 or 5;

$R_2$ is $C_{3-8}$ alkyl, $C_{1-8}$ alkyl ($C_{3-8}$ cycloalkyl), $C_{3-8}$ cycloalkyl, heteroaryl, or substituted aryl;

$R_4$, $R_5$ and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $—(CH_2)_xNR_7R_8$, $—(CH_2)_xOR_7$, $—(CH_2)_xNR_9COR_7$, $—(CH_2)_xNR_9SO_2R_7$, $—(CH_2)_xNR_9CO_2R_7$, $—(CH_2)_xNHCOR_7$, $—(CH_2)_xNHSO_2R_7$, $—(CH_2)_xNHCO_2R_7$, $—(CH_2)_xCONR_7R_8$, $—(CH_2)_xCONR_7(CH_2)_yCO_2R_9$, $—(CH_2)_xCONR_7(CH_2)_yCONR_7R_8$, $—(CH_2)_xCONR_7(CH_2)_yR_9$, $—(CH_2)_xCOR_7$, $—(CH_2)_xCO_2R_7$, $—(CH_2)_xSO_2NR_7(CH_2)_yR_9$, $—CHR_7COR_9$, $—CHR_7CONHCHR_8COR_9$, $—CONR_7R_8$, $—CONR_7(CH_2)_xCO_2R_8$, $—CONR_7CHR_8CO_2R_9$, $—CO_2R_9$, H, or $—NHCO_2R_7$, $—(CH_2)_xSO_2NR_7R_8$; $—SF_5$; or $R_4$ and $R_5$ together make a 4-8 member ring which may be substituted with one or more heteroatoms; or $R_4$ and $R_5$ together make a 5-8 nitrogen containing member ring with one or more carbonyl groups;

wherein the group $R_4$ is optionally substituted with one or more fluorine atoms;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each x is independently 0-8; and each y is independently 1-8.

2. The method of claim 1, wherein the apelin receptor agonist is Compound 1, which is (3S)-3-({1-cyclopentyl-5-[2-(trifluoromethyl)phenyl]-1H-pyrazol-3-yl}formamido)-5-(3,3-difluoropiperidin-1-yl)pentanoic acid.

3. The method of claim 1, wherein the apelin receptor agonist is selected from:

(2S)-2-{[5-(2,6-dimethoxyphenyl)-1-(4-fluorophenyl)-1H-pyrazol-3-yl]formamido}-4-methylpentanoic acid;

(3S)-3-{[5-(2,6-dimethoxyphenyl)-1-(4-fluorophenyl)-1H-pyrazol-3-yl]formamido}-5-methylhexanoic acid;

(3S)-3-{[5-(2,6-dimethoxyphenyl)-1-(4-fluorophenyl)-1H-pyrazol-3-yl]formamido}-5-methylhexanamide;

(3R)-3-{[5-(2,6-dimethoxyphenyl)-1-(4-fluorophenyl)-1H-pyrazol-3-yl]formamido}-5-methylhexanoic acid;

2-(2-cyclohexyl-2-{[5-(2,6-dimethoxyphenyl)-1-(4-fluorophenyl)-1H-pyrazol-3-yl]formamido}acetamido) acetic acid;

(2S)-2-cyclohexyl-2-{[5-(2,6-dimethoxyphenyl)-1-(4-fluorophenyl)-1H-pyrazol-3-yl]formamido}acetic acid;

2-[(3S)-3-{[5-(2,6-dimethoxyphenyl)-1-(4-fluorophenyl)-1H-pyrazol-3-yl]formamido}-5-methylhexanamido]acetic acid;

(3S)-3-{[1-cyclohexyl-5-(2,6-dimethoxyphenyl)-1H-pyrazol-3-yl]formamido}-5-methylhexanoic acid;

2-[(3S)-3-{[1-cyclohexyl-5-(2,6-dimethoxyphenyl)-1H-pyrazol-3-yl]formamido}-5-methylhexanamido]acetic acid;

(3S)-3-({5-[2-(benzyloxy)-6-methoxyphenyl]-1-(4-fluorophenyl)-1H-pyrazol-3-yl}formamido)-5-methylhexanoic acid;

(3S)-3-{[1-(4-fluorophenyl)-5-[2-methoxy-6-(2-methoxy-2-oxoethoxy)phenyl]-1H-pyrazol-3-yl]formamido}-5-methylhexanoic acid;

2-cyclohexyl-2-{[1-cyclohexyl-5-(2,6-dimethoxyphenyl)-1H-pyrazol-3-yl]formamido}acetic acid;

(3S)-3-{[1-(cyclohexylmethyl)-5-(2,6-dimethoxyphenyl)-1H-pyrazol-3-yl]formamido}-5-methylhexanoic acid;

methyl 2-[(3S)-3-{[1-cyclohexyl-5-(2,6-dimethoxyphenyl)-1H-pyrazol-3-yl]formamido}-5-methylhexanamido]acetate;

(3S)-3-{[5-(2,6-dimethoxyphenyl)-1-(2-methylpropyl)-1H-pyrazol-3-yl]formamido}-5-methylhexanoic acid;

(3S)-3-({5-[2-(benzyloxy)-6-methoxyphenyl]-1-cyclohexyl-1H-pyrazol-3-yl}formamido)-5-methylhexanoic acid methyl 2-[(3S)-3-({5-[2-(benzyloxy)-6-methoxyphenyl]-1-cyclohexyl-1H-pyrazol-3-yl}formamido)-5-methylhexanamido]acetate 2-[(3S)-3-({5-[2-(benzyloxy)-6-methoxyphenyl]-1-cyclohexyl-1H-pyrazol-3-yl}formamido)-5-methylhexanamido]acetic acid methyl 2-[(3S)-3-{[5-(2,6-dimethoxyphenyl)-1-(2-methylpropyl)-1H-pyrazol-3-yl]formamido}-5-methylhexanamido]acetate (3S)—N-benzyl-3-({5-[2-(benzyloxy)-6-methoxyphenyl]-1-cyclohexyl-1H-pyrazol-3-yl}formamido)-5-methylhexanamide (3S)-3-({5-[2-(benzyloxy)-6-methoxyphenyl]-1-cyclohexyl-1H-pyrazol-3-yl}formamido)-N-butyl-5-methylhexanamide (3S)-3-({5-[2-(benzyloxy)-6-methoxyphenyl]-1-cyclohexyl-1H-pyrazol-3-yl}formamido)-5-methyl-N-(1,3-oxazol-2-ylmethyl)hexanamide (3S)-3-({5-[2-(benzyloxy)-6-methoxyphenyl]-1-cyclohexyl-1H-pyrazol-3-yl}formamido)-N-[(dimethylcarbamoyl)methyl]-5-methylhexanamide methyl 2-[(3S)-3-{[5-(2,6-dimethoxyphenyl)-1-(4-fluorophenyl)-1H-pyrazol-3-yl]formamido}-5-methylhexanamido]acetate ethyl 3-[(3S)-3-({5-[2-(benzyloxy)-6-methoxyphenyl]-1-cyclohexyl-1H-pyrazol-3-yl}formamido)-5-methylhexanamido]propanoate (3S)-3-{[5-(2,6-dimethoxyphenyl)-1-(2-methylpropyl)-1H-pyrazol-3-yl]formamido}-5-methyl-N-(1,3-oxazol-2-ylmethyl)hexanamide (3S)-3-{[5-(2,6-dimethoxyphenyl)-1-(2-methylpropyl)-1H-pyrazol-3-yl]formamido}-N,5-dimethylhexanamide (3S)-3-{[5-(2,6-dimethoxyphenyl)-1-(2-methylpropyl)-1H-pyrazol-3-yl]formamido}-N-(2-hydroxyethyl)-5-methylhexanamide (3S)—N-butyl-3-{[5-(2,6-dimethoxyphenyl)-1-(2-methylpropyl)-1H-pyrazol-3-yl]formamido}-5-methylhexanamide (3R)—N-butyl-3-{[5-(2,6-dimethoxyphenyl)-1-(2-methylpropyl)-1H-pyrazol-3-yl]formamido}-5-methylhexanamide (3S)-3-{[5-(2,6-dimethoxyphenyl)-1-(2-methylpropyl)-1H-pyrazol-3-yl]formamido}-N-hexyl-5-methylhexanamide (3S)—N-(cyclohexylmethyl)-3-{[5-(2,6-dimethoxyphenyl)-1-(2-methylpropyl)-1H-pyrazol-3-yl]formamido}-5-methylhexanamide (3S)-3-{[5-(2,6-dimethoxyphenyl)-1-(2-methylpropyl)-1H-pyrazol-3-yl]formamido}-5-methyl-N-pentyl-hexanamide (3S)-3-{[5-(2,6-dimethoxyphenyl)-1-(2-methylpropyl)-1H-pyrazol-3-yl]formamido}-5-methyl-N-propyl-hexanamide (3S)-3-{[5-(2,6-dimethoxyphenyl)-1-(2-methylpropyl)-1H-pyrazol-3-yl]formamido}-N-ethyl-5-methyl-hexanamide (3S)-3-{[5-(2,6-dimethoxyphenyl)-1-(2-methylpropyl)-1H-pyrazol-3-yl]formamido}-5-methyl-N-(propan-2-yl)hexanamide (3S)-3-{[5-(2,6-dimethoxyphenyl)-1-(2-methylpropyl)-1H-pyrazol-3-yl]formamido}-N-(4-fluorophenyl)-5-methylhexanamide methyl (3S)-3-{[5-(2,6-dimethoxyphenyl)-1-(2-methyl-propyl)-1H-pyrazol-3-yl]formamido}-5-methyl-hexanoate (3S)-3-{[5-(3,5-difluoro-2,6-dimethoxyphenyl)-1-(2-methylpropyl)-1H-pyrazol-3-yl]formamido}-5-meth-ylhexanoic acid (3S)—N-butyl-3-{[5-(3,5-difluoro-2,6-dimethoxyphe-nyl)-1-(2-methylpropyl)-1H-pyrazol-3-yl]forma-mido}-5-methylhexanamide (2S)-2-cyclohexyl-2-{[5-(2,6-dimethoxyphenyl)-1-(2-methylpropyl)-1H-pyrazol-3-yl]formamido}acetic acid (3S)-3-{[5-(2,6-dimethoxyphenyl)-1-(2-methylpropyl)-1H-pyrazol-3-yl]formamido}-N,5-dimethyl-N-propyl-hexanamide (3S)—N-cyclopropyl-3-{[5-(2,6-dimethoxyphenyl)-1-(2-methylpropyl)-1H-pyrazol-3-yl]formamido}-5-meth-ylhexanamide (3S)—N-cyclobutyl-3-{[5-(2,6-dimethoxyphenyl)-1-(2-methylpropyl)-1H-pyrazol-3-yl]formamido}-5-meth-ylhexanamide 2-[(3S)-3-{[5-(2,6-dimethoxyphenyl)-1-(2-methylpro-pyl)-1H-pyrazol-3-yl]formamido}-5-methylhexana-mido]acetic acid (3S)—N-(carbamoylmethyl)-3-{[5-(2,6-dimethoxyphe-nyl)-1-(2-methylpropyl)-1H-pyrazol-3-yl]forma-mido}-5-methylhexanamide (3S)-3-{[5-(2,6-dimethoxyphenyl)-1-(2-methylpropyl)-1H-pyrazol-3-yl]formamido}-5-methyl-N-[(methyl-carbamoyl)methyl]hexanamide (3S)-3-{[1-(cyclopropylmethyl)-5-(2,6-dimethoxyphe-nyl)-1H-pyrazol-3-yl]formamido}-5-methylhexanoic acid (3S)-3-{[1-cyclopentyl-5-(2,6-dimethoxyphenyl)-1H-pyrazol-3-yl]formamido}-5-methylhexanoic acid methyl 2-[(3S)-3-{[1-(cyclopropylmethyl)-5-(2,6-dime-thoxyphenyl)-1H-pyrazol-3-yl]formamido}-5-methyl-hexanamido]acetate methyl 2-[(3S)-3-{[1-cyclopentyl-5-(2,6-dimethoxyphe-nyl)-1H-pyrazol-3-yl]formamido}-5-methylhexana-mido]acetate (3S)—N-cyclopentyl-3-{[5-(2,6-dimethoxyphenyl)-1-(2-methylpropyl)-1H-pyrazol-3-yl]formamido}-5-meth-ylhexanamide methyl 2-[(3S)-3-{[5-(2,6-dimethoxyphenyl)-1-propyl-1H-pyrazol-3-yl]formamido}-5-methylhexanamido]acetate methyl 2-[(3S)-3-{[5-(2,6-dimethoxyphenyl)-1-(2,2-dim-ethylpropyl)-1H-pyrazol-3-yl]formamido}-5-methyl-hexanamido]acetate methyl 2-[(2S)-2-{[5-(2,6-dimethoxyphenyl)-1-(2-meth-ylpropyl)-1H-pyrazol-3-yl]formamido}-4-methylpen-tanamido]acetate methyl 2-[(2S)-2-{[1-cyclohexyl-5-(2,6-dimethoxyphe-nyl)-1H-pyrazol-3-yl]formamido}-4-methylpentana-mido]acetate ethyl 3-[(2S)-2-{[5-(2,6-dimethoxyphenyl)-1-(2-methyl-propyl)-1H-pyrazol-3-yl]formamido}-4-methylpen-tanamido]propanoate methyl 2-[(2S)-3-cyclohexyl-2-{[5-(2,6-dimethoxyphe-nyl)-1-(2-methylpropyl)-1H-pyrazol-3-yl]formamido}propanamido]acetate (2S)-3-cyclohexyl-2-{[5-(2,6-dimethoxyphenyl)-1-(2-methylpropyl)-1H-pyrazol-3-yl]formamido}propanoic acid methyl 2-[(2S)-2-{[5-(2,6-dimethoxyphenyl)-1-(2-meth-ylpropyl)-1H-pyrazol-3-yl]formamido}-3-phenylpro-panamido]acetate methyl 2-[(2S)-2-{[5-(2,6-dimethoxyphenyl)-1-(2-meth-ylpropyl)-1H-pyrazol-3-yl]formamido}hexanamido]acetate methyl 2-[(2S)-2-{[5-(2,6-dimethoxyphenyl)-1-(2-meth-ylpropyl)-1H-pyrazol-3-yl]formamido}-4-phenylbu-tanamido]acetate (3S)-5-cyclohexyl-3-{[5-(2,6-dimethoxyphenyl)-1-(2-methylpropyl)-1H-pyrazol-3-yl]formamido}pentanoic acid methyl 2-[(3S)-5-cyclohexyl-3-{[5-(2,6-dimethoxyphe-nyl)-1-(2-methylpropyl)-1H-pyrazol-3-yl]formamido}pentanamido]acetate methyl 2-[(2S)-3-cyclohexyl-2-{[5-(2,5-dimethoxyphe-nyl)-1-(2-methylpropyl)-1H-pyrazol-3-yl]formamido}propanamido]acetate methyl 2-[(3S)-3-{[5-(2,6-dimethoxyphenyl)-1-(2-meth-ylpropyl)-1H-pyrazol-3-yl]formamido}-N,5-dimethyl-hexanamido]acetate methyl 2-[(2S)-2-{[5-(2,6-dimethoxyphenyl)-1-(2-meth-ylpropyl)-1H-pyrazol-3-yl]formamido}-N,4-dimethyl-pentanamido]acetate 2-[(3S)-5-cyclohexyl-3-{[5-(2,6-dimethoxyphenyl)-1-(2-methylpropyl)-1H-pyrazol-3-yl]formamido}pentanamido]acetic acid (2S)-2-{[5-(2,6-dimethoxyphenyl)-1-(2-methylpropyl)-1H-pyrazol-3-yl]formamido}-4-phenyl-N-propylbu-tanamide 5-(2,6-dimethoxyphenyl)-1-(2-methylpropyl)-N-[(2S)-1-oxo-4-phenyl-1-(pyrrolidin-1-yl)butan-2-yl]-1H-pyra-zole-3-carboxamide methyl 2-[(2S)-2-{[5-(2,6-dimethoxyphenyl)-1-(2-meth-ylpropyl)-1H-pyrazol-3-yl]formamido}-N-methyl-4-phenylbutanamido]acetate (2S)-2-{[5-(2,6-dimethoxyphenyl)-1-(2-methylpropyl)-1H-pyrazol-3-yl]formamido}-N-(2-methoxyethyl)-4-phenylbutanamide (3S)—N-cyclobutyl-5-cyclohexyl-3-{[5-(2,6-dimethoxy-phenyl)-1-(2-methylpropyl)-1H-pyrazol-3-yl]formamido}pentanamide (3S)-5-cyclohexyl-3-{[5-(2,6-dimethoxyphenyl)-1-(2-methylpropyl)-1H-pyrazol-3-yl]formamido}pentanamide (3S)-5-cyclohexyl-3-{[5-(2,6-dimethoxyphenyl)-1-(2-methylpropyl)-1H-pyrazol-3-yl]formamido}-N-(2-hy-droxybutyl)pentanamide (2S)-2-{[5-(2,6-dimethoxyphenyl)-1-(2-methylpropyl)-1H-pyrazol-3-yl]formamido}-N-(2-hydroxybutyl)-4-phenylbutanamide (2S)-2-{[5-(2,6-dimethoxyphenyl)-1-(2-methylpropyl)-1H-pyrazol-3-yl]formamido}-N-(2-oxobutyl)-4-phe-nylbutanamide (3S)-5-cyclohexyl-3-{[5-(2,6-dimethoxyphenyl)-1-(2-methylpropyl)-1H-pyrazol-3-yl]formamido}-N-(2-oxobutyl)pentanamide methyl 2-[(3S)-3-{1-[5-(2,6-dimethoxyphenyl)-1-(2-methylpropyl)-1H-pyrazol-3-yl]-N-methylformamido}-5-methylhexanamido]acetate (3S)-5-cyclohexyl-3-{[5-(2,6-dimethoxyphenyl)-1-(2-methylpropyl)-1H-pyrazol-3-yl]formamido}-N-(2-methoxyethyl)pentanamide methyl 2-[(3S)-5-cyclohexyl-3-{[5-(2,6-dimethoxyphenyl)-1-(2-methylpropyl)-1H-pyrazol-3-yl]formamido}-N-methylpentanamido]acetate (2S)—N-cyclobutyl-2-{[5-(2,6-dimethoxyphenyl)-1-(2-methylpropyl)-1H-pyrazol-3-yl]formamido}-4-phenylbutanamide methyl 2-[(3S)-6-cyclohexyl-3-{[5-(2,6-dimethoxyphenyl)-1-(2-methylpropyl)-1H-pyrazol-3-yl]formamido}hexanamido]acetate (3S)-3-{[5-(2,6-dimethoxyphenyl)-1-(2-methylpropyl)-1H-pyrazol-3-yl]formamido}-N-(2-hydroxybutyl)-5-(piperidin-1-yl)pentanamide (3S)—N-cyclobutyl-3-{[5-(2,6-dimethoxyphenyl)-1-(2-methylpropyl)-1H-pyrazol-3-yl]formamido}-5-(piperidin-1-yl)pentanamide (3S)-3-{[5-(2,6-dimethoxyphenyl)-1-(2-methylpropyl)-1H-pyrazol-3-yl]formamido}-N-(2-methoxyethyl)-5-(piperidin-1-yl)pentanamide (3S)-3-{[5-(2,6-dimethoxyphenyl)-1-(2-methylpropyl)-1H-pyrazol-3-yl]formamido}-5-(piperidin-1-yl)pentanoic acid (3S)-3-{[1-cyclopentyl-5-(2,6-dimethoxyphenyl)-1H-pyrazol-3-yl]formamido}-5-(piperidin-1-yl)pentanoic acid (3S)—N-cyclobutyl-3-{[1-cyclopentyl-5-(2,6-dimethoxyphenyl)-1H-pyrazol-3-yl]formamido}-5-(piperidin-1-yl)pentanamide (2S)-4-cyclohexyl-2-{[5-(2,6-dimethoxyphenyl)-1-(2-methylpropyl)-1H-pyrazol-3-yl]formamido}-N-(2-methoxyethyl)-N-methylbutanamide (3R)-3-cyclohexyl-3-{[5-(2,6-dimethoxyphenyl)-1-(4-fluorophenyl)-1H-pyrazol-3-yl]formamido}propanoic acid methyl 2-(3-cyclohexyl-3-{[5-(2,6-dimethoxyphenyl)-1-(4-fluorophenyl)-1H-pyrazol-3-yl]formamido}propanamido)acetate (3S)-5-cyclohexyl-3-{[5-(2,6-dimethoxyphenyl)-1-(2-methylpropyl)-1H-pyrazol-3-yl]formamido}-N-[(2R)-2-hydroxybutyl]pentanamide (3R)—N-cyclobutyl-3-{[1-cyclopentyl-5-(2,6-dimethoxyphenyl)-1H-pyrazol-3-yl]formamido}pent-4-enamide;

N-[(2S)-4-cyclohexyl-1-(1H-1,2,3,4-tetrazol-5-yl)butan-2-yl]-5-(2,6-dimethoxyphenyl)-1-(2-methylpropyl)-1H-pyrazole-3-carboxamide;

(3S)—N-cyclobutyl-3-{[1-cyclopentyl-5-(2,6-dimethoxyphenyl)-1H-pyrazol-3-yl]formamido}-5-(piperidin-1-yl)pentanamide;

(3S)—N-cyclobutyl-3-{[5-(2,6-dimethoxyphenyl)-1-(2-methylpropyl)-1H-pyrazol-3-yl]formamido}-5-phenylpentanamide;

(3S)-3-{[5-(2,6-dimethoxyphenyl)-1-(2-methylpropyl)-1H-pyrazol-3-yl]formamido}-4-phenylbutanoic acid;

(3S)-5-cyclohexyl-3-{[5-(2,6-dimethoxyphenyl)-1-(4-fluorophenyl)-1H-pyrazol-3-yl]formamido}pentanoic acid;

(3S)-3-{[5-(2,6-dimethoxyphenyl)-1-(4-fluorophenyl)-1H-pyrazol-3-yl]formamido}-5-phenylpentanoic acid;

(3R)-3-{[5-(2,6-dimethoxyphenyl)-1-(2-methylpropyl)-1H-pyrazol-3-yl]formamido}-3-phenylpropanoic acid;

(3S)-6-cyclohexyl-3-{[5-(2,6-dimethoxyphenyl)-1-(2-methylpropyl)-1H-pyrazol-3-yl]formamido}hexanoic acid (2S)—N-cyclobutyl-2-{[5-(2,6-dimethoxyphenyl)-1-(2-methylpropyl)-1H-pyrazol-3-yl]formamido}-3-phenylpropanamide tert-butyl (3S)-3-{[1-cyclopentyl-5-(2,6-dimethoxyphenyl)-1H-pyrazol-3-yl]formamido}-5-(morpholin-4-yl)pentanoate tert-butyl (3S)-3-{[1-cyclopentyl-5-(2,6-dimethoxyphenyl)-1H-pyrazol-3-yl]formamido}-5-(4-methylpiperazin-1-yl)pentanoate tert-butyl (3S)-3-{[1-cyclopentyl-5-(2,6-dimethoxyphenyl)-1H-pyrazol-3-yl]formamido}-5-(diethylamino)pentanoate tert-butyl (3S)-3-{[1-cyclopentyl-5-(2,6-dimethoxyphenyl)-1H-pyrazol-3-yl]formamido}-5-[(pyridin-4-ylmethyl)amino]pentanoate (3S)-3-{[1-cyclopentyl-5-(2,6-dimethoxyphenyl)-1H-pyrazol-3-yl]formamido}-5-(morpholin-4-yl)pentanoic acid (3S)-3-{[1-cyclopentyl-5-(2,6-dimethoxyphenyl)-1H-pyrazol-3-yl]formamido}-5-(4-methylpiperazin-1-yl)pentanoic acid (3S)-3-{[1-cyclopentyl-5-(2,6-dimethoxyphenyl)-1H-pyrazol-3-yl]formamido}-5-(diethylamino)pentanoic acid (3S)-3-{[1-cyclopentyl-5-(2,6-dimethoxyphenyl)-1H-pyrazol-3-yl]formamido}-5-[(pyridin-4-ylmethyl)amino]pentanoic acid (2S)-2-{[5-(2,6-dimethoxyphenyl)-1-(2-methylpropyl)-1H-pyrazol-3-yl]formamido}-4-phenylbutanoic acid (3S)—N-cyclobutyl-3-{[1-cyclopentyl-5-(2,6-dimethoxyphenyl)-1H-pyrazol-3-yl]formamido}-5-(morpholin-4-yl)pentanamide (3S)—N-cyclobutyl-3-{[1-cyclopentyl-5-(2,6-dimethoxyphenyl)-1H-pyrazol-3-yl]formamido}-5-(4-methylpiperazin-1-yl)pentanamide (3S)—N-cyclobutyl-3-{[1-cyclopentyl-5-(2,6-dimethoxyphenyl)-1H-pyrazol-3-yl]formamido}-5-(diethylamino)pentanamide 1-cyclopentyl-5-(2,6-dimethoxyphenyl)-N-[(4S)-2-oxo-1-(pyridin-4-ylmethyl)piperidin-4-yl]-1H-pyrazole-3-carboxamide tert-butyl (3S)-3-{[1-cyclopentyl-5-(2,6-dimethoxyphenyl)-1H-pyrazol-3-yl]formamido}-5-(pyrrolidin-1-yl)pentanoate (3S)-3-{[1-cyclopentyl-5-(2,6-dimethoxyphenyl)-1H-pyrazol-3-yl]formamido}-5-(pyrrolidin-1-yl)pentanoic acid hydrochloride (3S)—N-cyclobutyl-3-{[1-cyclopentyl-5-(2,6-dimethoxyphenyl)-1H-pyrazol-3-yl]formamido}-5-(pyrrolidin-1-yl)pentanamide tert-butyl (3S)-5-(azepan-1-yl)-3-{[1-cyclopentyl-5-(2,6-dimethoxyphenyl)-1H-pyrazol-3-yl]formamido}pentanoate tert-butyl (3S)-5-{7-azabicyclo[2.2.1]heptan-7-yl}-3-{[1-cyclopentyl-5-(2,6-dimethoxyphenyl)-1H-pyrazol-3-yl]formamido}pentanoate (3S)—N-cyclobutyl-3-{[5-(2,6-dimethoxyphenyl)-1-(2-methylpropyl)-1H-pyrazol-3-yl]formamido}-4-phenylbutanamide (3S)-5-(azepan-1-yl)-3-{[1-cyclopentyl-5-(2,6-dimethoxyphenyl)-1H-pyrazol-3-yl]formamido}pentanoic acid (3S)-5-{7-azabicyclo[2.2.1]heptan-7-yl}-3-{[1-cyclopentyl-5-(2,6-dimethoxyphenyl)-1H-pyrazol-3-yl]formamido}pentanoic acid (3S)-5-(azepan-1-yl)-N-cyclobutyl-3-{[1-cyclopentyl-5-(2,6-dimethoxyphenyl)-1H-pyrazol-3-yl]formamido}pentanamide (3S)-5-{7-azabicyclo[2.2.1]heptan-7-yl}-N-cyclobutyl-3-{[1-cyclopentyl-5-(2,6-dimethoxyphenyl)-1H-pyrazol-3-yl]formamido}pentanamide (3S)-3-{[1-cyclopentyl-5-(2,6-dimethoxyphenyl)-1H-pyrazol-3-yl]formamido}-N-(1-methylcyclobutyl)-5-(piperidin-1-yl)pentanamide (3S)-3-{[1-cyclopentyl-5-(2,6-dimethoxyphenyl)-1H-pyrazol-3-yl]formamido}-N-(3-methyloxetan-3-yl)-5-(piperidin-1-yl)pentanamide (3S)-3-{[1-cyclopentyl-5-(2,6-dimethoxyphenyl)-1H-pyrazol-3-yl]formamido}-N-(1-methylcyclopropyl)-5-(piperidin-1-yl)pentanamide (3S)—N-cyclobutyl-3-{[1-cyclopentyl-5-(2,6-dimethoxyphenyl)-1H-pyrazol-3-yl]formamido}-5-(2,6-dimethylpiperidin-1-yl)pentanamide (3S)-3-{[1-cyclopentyl-5-(2,6-dimethoxyphenyl)-1H-pyrazol-3-yl]formamido}-5-(2,6-dimethylpiperidin-1-yl)pentanoic acid (3S)—N-cyclobutyl-3-{[1-cyclopentyl-5-(2,6-dimethoxyphenyl)-1H-pyrazol-3-yl]formamido}-N-methyl-5-(piperidin-1-yl)pentanamide (3S)-3-{[1-cyclopentyl-5-(2,6-dimethoxyphenyl)-1H-pyrazol-3-yl]formamido}-N-(oxan-4-yl)-5-(piperidin-1-yl)pentanamide (3S)—N-tert-butyl-3-{[1-cyclopentyl-5-(2,6-dimethoxyphenyl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-N-(2-methoxyethyl)-N-methyl-5-(piperidin-1-yl)pentanamide (3S)—N-cyclobutyl-3-{[1-cyclopentyl-5-(2,6-dimethoxyphenyl)-1H-pyrazol-3-yl]formamido}-5-(4,4-difluoropiperidin-1-yl)pentanamide (3S)-3-{[1-cyclopentyl-5-(2,6-dimethoxyphenyl)-1H-pyrazol-3-yl]formamido}-N-(2-methoxyethyl)-5-(piperidin-1-yl)pentanamide 1-cyclopentyl-5-(2,6-dimethoxyphenyl)-N-[(3S)-1-{2-oxa-6-azaspiro[3.3]heptan-6-yl}-1-oxo-5-(piperidin-1-yl)pentan-3-yl]-1H-pyrazole-3-carboxamide (3S)-3-{[1-cyclopentyl-5-(2,6-dimethoxyphenyl)-1H-pyrazol-3-yl]formamido}-5-(piperidin-1-yl)-N-(1,3-thiazol-2-yl)pentanamide (3S)-3-{[1-cyclopentyl-5-(2,6-dimethoxyphenyl)-1H-pyrazol-3-yl]formamido}-N-(1,3-oxazol-2-yl)-5-(piperidin-1-yl)pentanamide (3S)-3-{[1-cyclopentyl-5-(2,6-dimethoxyphenyl)-1H-pyrazol-3-yl]formamido}-N-(1,3-oxazol-2-ylmethyl)-5-(piperidin-1-yl)pentanamide cyclobutyl (3S)-3-{[1-cyclopentyl-5-(2,6-dimethoxyphenyl)-1H-pyrazol-3-yl]formamido}-5-(piperidin-1-yl)pentanoate (3S)-3-(1-{5-[2,6-bis(2,2,2-trifluoroethoxy)phenyl]-1-cyclopentyl-1H-pyrazol-3-yl}-N-ethylformamido)-N-cyclobutyl-5-(piperidin-1-yl)pentanamide 1-cyclopentyl-5-(2,6-dimethoxyphenyl)-N-[(2S)-1-(5-methyl-1,3,4-oxadiazol-2-yl)-4-(piperidin-1-yl)butan-2-yl]-1H-pyrazole-3-carboxamide (3S)—N-cyclobutyl-3-(1-{1-cyclopentyl-5-[2-(trifluoromethoxy)phenyl]-1H-pyrazol-3-yl}-N-ethylformamido)-5-(piperidin-1-yl)pentanamide (3S)—N-cyclobutyl-3-{1-[1-cyclopentyl-5-(2-fluoro-6-methoxyphenyl)-1H-pyrazol-3-yl]-N-ethylformamido}-5-(piperidin-1-yl)pentanamide (3S)—N-cyclobutyl-3-{1-[5-(2,6-dimethoxyphenyl)-1-(pentan-3-yl)-1H-pyrazol-3-yl]-N-ethylformamido}-5-(piperidin-1-yl)pentanamide (3S)—N-cyclobutyl-3-{1-[1-cyclopentyl-5-(thiophen-2-yl)-1H-pyrazol-3-yl]-N-ethylformamido}-5-(piperidin-1-yl)pentanamide (3S)—N-cyclobutyl-3-{[1-cyclopentyl-5-(2,6-dimethoxyphenyl)-1H-pyrazol-3-yl]formamido}-5-(3,3-difluoropiperidin-1-yl)pentanamide (3S)-5-{2-azaspiro[3.3]heptan-2-yl}-N-cyclobutyl-3-{[1-cyclopentyl-5-(2,6-dimethoxyphenyl)-1H-pyrazol-3-yl]formamido}pentanamide (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-yl)pentanamide (3S)-3-{[1-cyclopentyl-5-(2,6-dimethoxyphenyl)-1H-pyrazol-3-yl]formamido}-N-methyl-5-(piperidin-1-yl)-N-(1,3-thiazol-2-yl)pentanamide (3S)-3-{[1-cyclopentyl-5-(2,6-dimethoxyphenyl)-1H-pyrazol-3-yl]formamido}-5-(piperidin-1-yl)pentanamide (3S)-3-({5-[2,6-bis(2,2,2-trifluoroethoxy)phenyl]-1-cyclopentyl-1H-pyrazol-3-yl}formamido)-N-cyclobutyl-5-(piperidin-1-yl)pentanamide (3S)—N-cyclobutyl-3-{[1-cyclopentyl-5-(2,4,6-trifluorophenyl)-1H-pyrazol-3-yl]formamido}-5-(piperidin-1-yl)pentanamide (3S)—N-cyclobutyl-3-{[1-cyclopentyl-5-(4-ethoxy-2,6-difluorophenyl)-1H-pyrazol-3-yl]formamido}-5-(piperidin-1-yl)pentanamide (3S)—N-cyclobutyl-3-{[5-(2,6-dimethoxyphenyl)-1-(2-methylcyclohexyl)-1H-pyrazol-3-yl]formamido}-5-(piperidin-1-yl)pentanamide (3S)—N-cyclobutyl-3-{[5-(2,6-dimethoxyphenyl)-1-(pentan-3-yl)-1H-pyrazol-3-yl]formamido}-5-(piperidin-1-yl)pentanamide 1-cyclopentyl-5-(2,6-dimethoxyphenyl)-N-[(3S)-1-hydroxy-5-(piperidin-1-yl)pentan-3-yl]-1H-pyrazole-3-carboxamide (3S)—N-cyclobutyl-3-({1-cyclopentyl-5-[2-(trifluoromethoxy)phenyl]-1H-pyrazol-3-yl}formamido)-5-(piperidin-1-yl)pentanamide (3S)—N-cyclobutyl-3-({1-cyclopentyl-5-[2-(methylsulfanyl)phenyl]-1H-pyrazol-3-yl}formamido)-5-(piperidin-1-yl)pentanamide (3S)—N-cyclobutyl-3-{[1-cyclopentyl-5-(2-methoxyphenyl)-1H-pyrazol-3-yl]formamido}-5-(piperidin-1-yl)pentanamide (3S)—N-cyclobutyl-3-{[1-cyclopentyl-5-(thiophen-2-yl)-1H-pyrazol-3-yl]formamido}-5-(piperidin-1-yl)pentanamide (3S)—N-cyclobutyl-3-{[1-cyclopentyl-5-(2-ethylphenyl)-1H-pyrazol-3-yl]formamido}-5-(piperidin-1-yl)pentanamide 1-cyclopentyl-5-(2,6-dimethoxyphenyl)-N-[(2S)-4-(piperidin-1-yl)-1-(1H-1,2,3,4-tetrazol-5-yl)butan-2-yl]-1H-pyrazole-3-carboxamide (3S)—N-cyclobutyl-3-[(1-cyclopentyl-5-phenyl-1H-pyrazol-3-yl)formamido]-5-(piperidin-1-yl)pentanamide (3S)—N-cyclobutyl-3-({1-cyclopentyl-5-[4-fluoro-2-(2,2,2-trifluoroethoxy)phenyl]-1H-pyrazol-3-yl}formamido)-5-(piperidin-1-yl)pentanamide (3S)—N-cyclobutyl-3-{[1-cyclopentyl-5-(2-methanesulfonylphenyl)-1H-pyrazol-3-yl]formamido}-5-(piperidin-1-yl)pentanamide (3S)—N-cyclobutyl-3-{[1-cyclopentyl-5-(pyrimidin-5-yl)-1H-pyrazol-3-yl]formamido}-5-(piperidin-1-yl)pentanamide (3S)—N-cyclobutyl-3-{[1-cyclopentyl-5-(dimethyl-1,2-oxazol-4-yl)-1H-pyrazol-3-yl]formamido}-5-(piperidin-1-yl)pentanamide (3S)-3-{[5-(2-chloro-6-methoxyphenyl)-1-cyclopentyl-1H-pyrazol-3-yl]formamido}-N-cyclobutyl-5-(piperidin-1-yl)pentanamide (3S)—N-cyclobutyl-3-{[1-cyclopentyl-5-(2,6-dimethylphenyl)-1H-pyrazol-3-yl]formamido}-5-(piperidin-1-yl)pentanamide (3S)—N-cyclobutyl-3-{[1-cyclopentyl-5-(2-fluoro-6-methoxyphenyl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-5-(piperidin-1-yl)-N-[2-(1H-1,2,3,4-tetrazol-5-yl)ethyl]pentanamide 2-(3-{[(2S)-1-(cyclobutylcarbamoyl)-4-(piperidin-1-yl)butan-2-yl]carbamoyl}-1-cyclopentyl-1H-pyrazol-5-yl)pyridin-1-ium-1-olate (3S)—N-cyclobutyl-3-{[1-cyclopentyl-5-(pyridin-2-yl)-1H-pyrazol-3-yl]formamido}-5-(piperidin-1-yl)pentanamide (2S)—N-cyclobutyl-2-{[1-cyclopentyl-5-(2,6-dimethoxyphenyl)-1H-pyrazol-3-yl]formamido}-3-cyclopropylpropanamide (2S)—N,3-dicyclobutyl-2-{[1-cyclopentyl-5-(2,6-dimethoxyphenyl)-1H-pyrazol-3-yl]formamido}propanamide (3S)—N-cyclobutyl-3-{[1-cyclopentyl-5-(1,3-thiazol-4-yl)-1H-pyrazol-3-yl]formamido}-5-(piperidin-1-yl)pentanamide (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-ylmethyl)pentanamide (3S)-3-{[1-cyclopentyl-5-(2,6-dimethoxyphenyl)-1H-pyrazol-3-yl]formamido}-5-phenyl-N-(1,3-thiazol-2-yl)pentanamide (3S)-3-{[1-cyclopentyl-5-(2,6-dimethoxyphenyl)-1H-pyrazol-3-yl]formamido}-5-phenyl-N-(1H-1,2,3,4-tetrazol-5-yl)pentanamide (3S)-3-{[1-cyclopentyl-5-(2,6-dimethoxyphenyl)-1H-pyrazol-3-yl]formamido}-5-phenyl-N-(1,3-thiazol-2-ylmethyl)pentanamide (3S)-3-{[1-cyclopentyl-5-(2,6-dimethoxyphenyl)-1H-pyrazol-3-yl]formamido}-5-phenyl-N-(1H-1,2,3,4-tetrazol-5-ylmethyl)pentanamide (3S)-3-{[1-cyclopentyl-5-(2,6-dimethoxyphenyl)-1H-pyrazol-3-yl]formamido}-5-(3,3-difluoropiperidin-1-yl)-N-(1,3-thiazol-2-yl)pentanamide (2S)-2-{[1-cyclopentyl-5-(2,6-dimethoxyphenyl)-1H-pyrazol-3-yl]formamido}-3-cyclopropylpropanoic acid (2S)-3-cyclobutyl-2-{[1-cyclopentyl-5-(2,6-dimethoxyphenyl)-1H-pyrazol-3-yl]formamido}propanoic acid (2S)-2-{[1-cyclopentyl-5-(2,6-dimethoxyphenyl)-1H-pyrazol-3-yl]formamido}-4-phenyl-N-(1H-1,2,3,4-tetrazol-5-ylmethyl)butanamide (2S)-2-{[1-cyclopentyl-5-(2,6-dimethoxyphenyl)-1H-pyrazol-3-yl]formamido}-4-phenyl-N-(1,3-thiazol-2-ylmethyl)butanamide (2S)-2-{[1-cyclopentyl-5-(2,6-dimethoxyphenyl)-1H-pyrazol-3-yl]formamido}-4-phenylbutanoic acid 1-cyclopentyl-5-(2,6-dimethoxyphenyl)-N-[(2S)-4-phenyl-1-(1H-1,2,3,4-tetrazol-5-yl)butan-2-yl]-1H-pyrazole-3-carboxamide N-[(2S)-1-cyano-4-phenylbutan-2-yl]-1-cyclopentyl-5-(2,6-dimethoxyphenyl)-1H-pyrazole-3-carboxamide (3S)-3-{[1-cyclopentyl-5-(2,6-dimethoxyphenyl)-1H-pyrazol-3-yl]formamido}-5-phenylpentanamide (2S)-3-cyclopentyl-2-{[1-cyclopentyl-5-(2,6-dimethoxyphenyl)-1H-pyrazol-3-yl]formamido}propanoic acid (2S)-2-{[1-cyclopentyl-5-(2,6-dimethoxyphenyl)-1H-pyrazol-3-yl]formamido}-4-phenyl-N-(1H-1,2,3,4-tetrazol-5-yl)butanamide (2S)-2-{[1-cyclopentyl-5-(2,6-dimethoxyphenyl)-1H-pyrazol-3-yl]formamido}-4-phenyl-N-(1,3-thiazol-2-yl)butanamide (3S)—N-cyclobutyl-3-({1-cyclopentyl-5-[2-(propan-2-yl)phenyl]-1H-pyrazol-3-yl}formamido)-5-(piperidin-1-yl)pentanamide N-[(3R)-1-(cyclobutylamino)-5-(piperidin-1-yl)pentan-3-yl]-1-cyclopentyl-5-(2,6-dimethoxyphenyl)-1H-pyrazole-3-carboxamide (3S)—N-cyclobutyl-3-{[1-cyclopentyl-5-(2-ethyl-4-fluorophenyl)-1H-pyrazol-3-yl]formamido}-5-(piperidin-1-yl)pentanamide (3S)—N-cyclobutyl-3-({1-cyclopentyl-5-[2-(1,1-difluoroethyl)phenyl]-1H-pyrazol-3-yl}formamido)-5-(piperidin-1-yl)pentanamide (3S)-3-{[1-cyclopentyl-5-(2,6-dimethoxyphenyl)-1H-pyrazol-3-yl]formamido}-4-phenylbutanoic acid (3S)-3-{[1-cyclopentyl-5-(2,6-dimethoxyphenyl)-1H-pyrazol-3-yl]formamido}-4-phenyl-N-(1,3-thiazol-2-yl)butanamide (3S)-3-{[1-cyclopentyl-5-(2-ethylphenyl)-1H-pyrazol-3-yl]formamido}-5-(piperidin-1-yl)pentanoic acid hydrochloride (3S)-3-{[1-cyclopentyl-5-(2-ethylphenyl)-1H-pyrazol-3-yl]formamido}-5-(3,3-difluoropiperidin-1-yl)pentanoic acid (3S)-3-{[1-cyclopentyl-5-(2-ethylphenyl)-1H-pyrazol-3-yl]formamido}-5-(4,4-difluoropiperidin-1-yl)pentanoic acid (3S)-3-{[1-cyclopentyl-5-(2-ethylphenyl)-1H-pyrazol-3-yl]formamido}-5-(piperidin-1-yl)-N-(1,3-thiazol-2-yl)pentanamide (3S)-3-{[5-(2-chlorophenyl)-1-cyclopentyl-1H-pyrazol-3-yl]formamido}-N-cyclobutyl-5-(piperidin-1-yl)pentanamide (3S)—N-cyclobutyl-3-({1-cyclopentyl-5-[2-(trifluoromethyl)phenyl]-1H-pyrazol-3-yl}formamido)-5-(piperidin-1-yl)pentanamide (3S)-3-{[1-cyclopentyl-5-(2-ethylphenyl)-1H-pyrazol-3-yl]formamido}-5-(4,4-difluoropiperidin-1-yl)-N-(1,3-thiazol-2-yl)pentanamide (3S)-3-{[1-cyclopentyl-5-(2-ethylphenyl)-1H-pyrazol-3-yl]formamido}-5-(3,3-difluoropiperidin-1-yl)-N-(1,3-thiazol-2-yl)pentanamide (3S)—N-cyclobutyl-3-{[1-cyclopentyl-5-(2-ethylphenyl)-1H-pyrazol-3-yl]formamido}-5-(4,4-difluoropiperidin-1-yl)pentanamide (3S)—N-cyclobutyl-3-{[1-cyclopentyl-5-(2-ethylphenyl)-1H-pyrazol-3-yl]formamido}-5-(3,3-difluoropiperidin-1-yl)pentanamide (3S)—N-cyclobutyl-3-{[1-cyclopentyl-5-(2-cyclopropylphenyl)-1H-pyrazol-3-yl]formamido}-5-(piperidin-1-yl)pentanamide 1-cyclopentyl-5-(2,6-dimethoxyphenyl)-N-[(2S)-4-(piperidin-1-yl)-1-(4H-1,2,4-triazol-3-yl)butan-2-yl]-1H-pyrazole-3-carboxamide (3R,4E)-N-cyclobutyl-3-{[1-cyclopentyl-5-(2,6-dimethoxyphenyl)-1H-pyrazol-3-yl]formamido}-5-(4-fluorophenyl)pent-4-enamide (3S)—N-cyclobutyl-3-{[1-cyclopentyl-5-(2,6-dimethoxyphenyl)-1H-pyrazol-3-yl]formamido}-5-(4-fluorophenyl)pentanamide (3S)-3-{[1-cyclopentyl-5-(2,6-dimethoxyphenyl)-1H-pyrazol-3-yl]formamido}-5-(4-fluorophenyl)-N-(1,3-thiazol-2-yl)pentanamide (3R,4E)-N-cyclobutyl-3-{[1-cyclopentyl-5-(2,6-dimethoxyphenyl)-1H-pyrazol-3-yl]formamido}-5-(pyridin-3-yl)pent-4-enamide (3R,4E)-N-cyclobutyl-3-{[1-cyclopentyl-5-(2,6-dimethoxyphenyl)-1H-pyrazol-3-yl]formamido}-5-(pyridin-4-yl)pent-4-enamide (3S)—N-cyclobutyl-3-{[1-cyclopentyl-5-(2,6-dimethoxyphenyl)-1H-pyrazol-3-yl]formamido}-5-(pyridin-3-yl)pentanamide (3S)—N-cyclobutyl-3-{[1-cyclopentyl-5-(2,6-dimethoxyphenyl)-1H-pyrazol-3-yl]formamido}-5-(1-methylpiperidin-4-yl)pentanamide 1-cyclopentyl-5-(2,6-dimethoxyphenyl)-N-[(2S)-1-(1,3,4-oxadiazol-2-yl)-4-(piperidin-1-yl)butan-2-yl]-1H-pyrazole-3-carboxamide (3S)-3-({1-cyclopentyl-5-[2-(trifluoromethyl)phenyl]-1H-pyrazol-3-yl}formamido)-5-(3,3-difluoropiperidin-1-yl)pentanoic acid (3S)-3-({1-cyclopentyl-5-[2-(trifluoromethyl)phenyl]-1H-pyrazol-3-yl}formamido)-5-(4,4-difluoropiperidin-1-yl)pentanoic acid (3S)—N-cyclobutyl-3-({1-cyclopentyl-5-[2-(trifluoromethyl)phenyl]-1H-pyrazol-3-yl}formamido)-5-(3,3-difluoropiperidin-1-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-(1,3-oxazol-2-yl)pentanamide (3S)-3-({1-cyclopentyl-5-[2-(1,1-difluoroethyl)phenyl]-1H-pyrazol-3-yl}formamido)-5-(3,3-difluoropiperidin-1-yl)-N-(1,3-thiazol-2-yl)pentanamide (3S)-3-{[5-(2-chlorophenyl)-1-cyclopentyl-1H-pyrazol-3-yl]formamido}-5-(3,3-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(4,4-difluoropiperidin-1-yl)-N-(1,3-thiazol-2-yl)pentanamide (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-thiazol-2-yl)pentanamide (3S)-3-({1-cyclopentyl-5-[2-(1,1-difluoroethyl)phenyl]-1H-pyrazol-3-yl}formamido)-5-(3,3-difluoropiperidin-1-yl)pentanoic acid (3S)-3-{[5-(2-chlorophenyl)-1-cyclopentyl-1H-pyrazol-3-yl]formamido}-5-(3,3-difluoropiperidin-1-yl)pentanoic acid (3S)—N-cyclobutyl-3-({1-cyclopentyl-5-[2-(trifluoromethyl)thiophen-3-yl]-1H-pyrazol-3-yl}formamido)-5-(piperidin-1-yl)pentanamide (3R,4E)-N-cyclobutyl-3-{[1-cyclopentyl-5-(2,6-dimethoxyphenyl)-1H-pyrazol-3-yl]formamido}-5-(pyridin-2-yl)pent-4-enamide (3S)-3-({1-cyclopentyl-5-[2-(trifluoromethyl)phenyl]-1H-pyrazol-3-yl}formamido)-5-(4,4-difluoropiperidin-1-yl)-N-(5-methyl-1,3-thiazol-2-yl)pentanamide 1-cyclopentyl-N-[(2S)-4-(3,3-difluoropiperidin-1-yl)-1-(4H-1,2,4-triazol-3-yl)butan-2-yl]-5-[2-(trifluoromethyl)phenyl]-1H-pyrazole-3-carboxamide (3S)—N-cyclobutyl-3-{[1-cyclopentyl-5-(2-ethynylphenyl)-1H-pyrazol-3-yl]formamido}-5-(piperidin-1-yl)pentanamide (3S)—N-benzyl-3-({1-cyclopentyl-5-[2-(trifluoromethyl)phenyl]-1H-pyrazol-3-yl}formamido)-5-(4,4-difluoropiperidin-1-yl)pentanamide (3S)—N-(cyclohexylmethyl)-3-({1-cyclopentyl-5-[2-(trifluoromethyl)phenyl]-1H-pyrazol-3-yl}formamido)-5-(4,4-difluoropiperidin-1-yl)pentanamide (3S)—N-benzyl-3-({1-cyclopentyl-5-[2-(trifluoromethyl)phenyl]-1H-pyrazol-3-yl}formamido)-5-methylhexanamide N-benzyl-3-({1-cyclopentyl-5-[2-(trifluoromethyl)phenyl]-1H-pyrazol-3-yl}formamido)propanamide (3S)-3-{[1-cyclopentyl-5-(2,6-dimethoxyphenyl)-1H-pyrazol-3-yl]formamido}-N-(3,3-difluorocyclobutyl)-5-(piperidin-1-yl)pentanamide 1-cyclopentyl-5-(2,6-dimethoxyphenyl)-N-[(2S)-1-(1-methyl-1H-1,2,3,4-tetrazol-5-yl)-4-(piperidin-1-yl)butan-2-yl]-1H-pyrazole-3-carboxamide (3S)-3-{[5-(2-chlorophenyl)-1-cyclopentyl-1H-pyrazol-3-yl]formamido}-5-(3,3-difluoropiperidin-1-yl)-N-methyl-N-(1,3-thiazol-2-yl)pentanamide 1-cyclopentyl-5-(2,6-dimethoxyphenyl)-N-[(2S)-4-(piperidin-1-yl)-1-(1,3-thiazol-2-yl)butan-2-yl]-1H-pyrazole-3-carboxamide 3-({1-cyclopentyl-5-[2-(trifluoromethyl)phenyl]-1H-pyrazol-3-yl}formamido)-N-(1,3-thiazol-2-yl)propanamide 5-(2-chlorophenyl)-1-cyclopentyl-N-[(2S)-4-(3,3-difluoropiperidin-1-yl)-1-(4H-1,2,4-triazol-3-yl)butan-2-yl]-1H-pyrazole-3-carboxamide (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-oxazol-2-yl)pentanamide (3S)-3-{[5-(2-chlorophenyl)-1-cyclopentyl-1H-pyrazol-3-yl]formamido}-5-(3,3-difluoropiperidin-1-yl)-N-methyl-N-(1,3-oxazol-2-yl)pentanamide (3S)-3-{[5-(3-chloropyridin-4-yl)-1-cyclopentyl-1H-pyrazol-3-yl]formamido}-N-cyclobutyl-5-(3,3-difluoropiperidin-1-yl)pentanamide 5-(2-chlorophenyl)-1-cyclopentyl-N-[(2S)-4-(3,3-difluoropiperidin-1-yl)-1-(5-methyl-4H-1,2,4-triazol-3-yl)butan-2-yl]-1H-pyrazole-3-carboxamide 5-(2-chlorophenyl)-1-cyclopentyl-N-[(2S)-4-(3,3-difluoropiperidin-1-yl)-1-[5-(trifluoromethyl)-4H-1,2,4-triazol-3-yl]butan-2-yl]-1H-pyrazole-3-carboxamide (3S)—N-cyclobutyl-3-({1-cyclopentyl-5-[4-(trifluoromethyl)pyridin-3-yl]-1H-pyrazol-3-yl}formamido)-5-(3,3-difluoropiperidin-1-yl)pentanamide (3S)-3-({1-cyclopentyl-5-[2-(trifluoromethyl)phenyl]-1H-pyrazol-3-yl}formamido)-5-(4-fluorophenyl)pentanoic acid 1-cyclopentyl-N-[(2S)-4-(4-fluorophenyl)-1-(hydrazinecarbonyl)butan-2-yl]-5-[2-(trifluoromethyl)phenyl]-1H-pyrazole-3-carboxamide 5-(2-chlorophenyl)-1-cyclopentyl-N-[(2S)-4-(3,3-difluoropiperidin-1-yl)-1-(hydrazinecarbonyl)butan-2-yl]-1H-pyrazole-3-carboxamide (3S)-3-{[5-(4-chloropyridin-3-yl)-1-cyclopentyl-1H-pyrazol-3-yl]formamido}-N-cyclobutyl-5-(3,3-difluoropiperidin-1-yl)pentanamide (3S)-3-{[5-(4-chloropyridin-3-yl)-1-cyclopentyl-1H-pyrazol-3-yl]formamido}-5-(3,3-difluoropiperidin-1-yl)pentanoic acid (3S)-3-{[5-(2-chloropyridin-3-yl)-1-cyclopentyl-1H-pyrazol-3-yl]formamido}-5-(3,3-difluoropiperidin-1-yl)pentanoic acid (3S)-3-{[5-(2-chloropyridin-3-yl)-1-cyclopentyl-1H-pyrazol-3-yl]formamido}-N-cyclobutyl-5-(3,3-difluoropiperidin-1-yl)pentanamide 1-cyclopentyl-N-[(2S)-4-(4-fluorophenyl)-1-(4H-1,2,4-triazol-3-yl)butan-2-yl]-5-[2-(trifluoromethyl)phenyl]-1H-pyrazole-3-carboxamide 1-cyclopentyl-N-[(2S)-4-(4-fluorophenyl)-1-(5-methyl-4H-1,2,4-triazol-3-yl)butan-2-yl]-5-[2-(trifluoromethyl)phenyl]-1H-pyrazole-3-carboxamide 1-cyclopentyl-N-[(2S)-4-(4-fluorophenyl)-1-[5-(trifluoromethyl)-1,3,4-oxadiazol-2-yl]butan-2-yl]-5-[2-(trifluoromethyl)phenyl]-1H-pyrazole-3-carboxamide (3S)—N-cyclobutyl-3-({1-cyclopentyl-5-[3-(trifluoromethyl)pyridin-2-yl]-1H-pyrazol-3-yl}formamido)-5-(3,3-difluoropiperidin-1-yl)pentanamide (3S)—N-cyclobutyl-3-({1-cyclopentyl-5-[2-(trifluoromethyl)phenyl]-1H-pyrazol-3-yl}formamido)-5-(3,3-difluoropyrrolidin-1-yl)pentanamide (3S)-5-(3-cyanopyrrolidin-1-yl)-N-cyclobutyl-3-({1-cyclopentyl-5-[2-(trifluoromethyl)phenyl]-1H-pyrazol-3-yl}formamido)pentanamide (3S)-3-({1-cyclopentyl-5-[2-(trifluoromethyl)phenyl]-1H-pyrazol-3-yl}formamido)-5-(4-fluorophenyl)-N-(1-methylazetidin-3-yl)pentanamide (3S)—N-cyclobutyl-5-[cyclohexyl(methyl)amino]-3-({1-cyclopentyl-5-[2-(trifluoromethyl)phenyl]-1H-pyrazol-3-yl}formamido)pentanamide (3S)-5-cyclohexyl-3-({1-cyclopentyl-5-[2-(trifluoromethyl)phenyl]-1H-pyrazol-3-yl}formamido)pentanoic acid (3S)-3-({1-cyclopentyl-5-[2-(trifluoromethyl)phenyl]-1H-pyrazol-3-yl}formamido)-5-(3,3-difluoropyrrolidin-1-yl)pentanoic acid (3S)-3-({1-cyclopentyl-5-[2-(trifluoromethyl)phenyl]-1H-pyrazol-3-yl}formamido)-5-(morpholin-4-yl)pentanoic acid (3S)-3-({1-cyclopentyl-5-[2-(trifluoromethyl)phenyl]-1H-pyrazol-3-yl}formamido)-5-[(2S)-2-(trifluoromethyl)piperidin-1-yl]pentanoic acid (3S)-3-({1-cyclopentyl-5-[2-(trifluoromethyl)phenyl]-1H-pyrazol-3-yl}formamido)-5-[(2R)-2-(trifluoromethyl)piperidin-1-yl]pentanoic acid (3S)-3-({1-cyclopentyl-5-[2-(trifluoromethyl)phenyl]-1H-pyrazol-3-yl}formamido)-N-methyl-N-(1,3-thiazol-2-yl)-5-[(2R)-2-(trifluoromethyl)piperidin-1-yl]pentanamide (3S)—N-cyclobutyl-5-[cyclopentyl(methyl)amino]-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-(morpholin-4-yl)pentanamide (3S)—N-cyclobutyl-3-({1-cyclopentyl-5-[2-(trifluoromethyl)phenyl]-1H-pyrazol-3-yl}formamido)-5-(dipropylamino)pentanamide (3S)—N-cyclobutyl-3-({1-cyclopentyl-5-[2-(trifluoromethyl)phenyl]-1H-pyrazol-3-yl}formamido)-5-[methyl(2-methylpropyl)amino]pentanamide (3S)-3-({1-cyclopentyl-5-[2-(trifluoromethyl)phenyl]-1H-pyrazol-3-yl}formamido)-5-(piperidin-1-yl)pentanoic acid (3S)-3-({1-cyclopentyl-5-[2-(trifluoromethyl)phenyl]-1H-pyrazol-3-yl}formamido)-N-methyl-5-(morpholin-4-yl)-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-[(2S)-2-(trifluoromethyl)piperidin-1-yl]pentanamide (3S)—N-cyclobutyl-3-({1-cyclopentyl-5-[2-(trifluoromethyl)phenyl]-1H-pyrazol-3-yl}formamido)-5-(4-fluorophenyl)pentanamide (3S)-5-{8-azabicyclo[3.2.1]octan-8-yl}-N-cyclobutyl-3-({1-cyclopentyl-5-[2-(trifluoromethyl)phenyl]-1H-pyrazol-3-yl}formamido)pentanamide (3S)-3-({1-cyclopentyl-5-[2-(trifluoromethyl)phenyl]-1H-pyrazol-3-yl}formamido)-5-(pyrrolidin-1-yl)pentanoic acid (3S)-3-({1-cyclopentyl-5-[2-(trifluoromethyl)phenyl]-1H-pyrazol-3-yl}formamido)-N-methyl-5-(4-methyl-1H-pyrazol-1-yl)-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-(4-methyl-1H-pyrazol-1-yl)pentanamide (3S)-3-({1-cyclopentyl-5-[2-(trifluoromethyl)phenyl]-1H-pyrazol-3-yl}formamido)-5-(3,5-dimethyl-1H-pyrazol-1-yl)-N-methyl-N-(1,3-thiazol-2-yl)pentanamide (3S)—N-cyclobutyl-3-({1-cyclopentyl-5-[2-(trifluoromethyl)phenyl]-1H-pyrazol-3-yl}formamido)-5-(3,5-dimethyl-1H-pyrazol-1-yl)pentanamide (3S)—N-cyclobutyl-3-({1-cyclopentyl-5-[2-(trifluoromethyl)phenyl]-1H-pyrazol-3-yl}formamido)-5-(pyrrolidin-1-yl)pentanamide (3S)-5-(azepan-1-yl)-N-cyclobutyl-3-({1-cyclopentyl-5-[2-(trifluoromethyl)phenyl]-1H-pyrazol-3-yl}formamido)pentanamide (3S)—N-cyclobutyl-5-[cyclobutyl(methyl)amino]-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-{2-oxa-6-azaspiro[3.3]heptan-6-yl}pentanamide (3S)-3-({1-cyclopentyl-5-[2-(trifluoromethyl)phenyl]-1H-pyrazol-3-yl}formamido)-5-oxo-5-(piperidin-1-yl)pentanoic acid (3S)-3-({1-cyclopentyl-5-[2-(trifluoromethyl)phenyl]-1H-pyrazol-3-yl}formamido)-5-(3,3-difluoropiperidin-1-yl)-5-oxopentanoic acid (3S)-3-({1-cyclopentyl-5-[2-(trifluoromethyl)phenyl]-1H-pyrazol-3-yl}formamido)-5-(4-fluorophenyl)-N-(pyrrolidin-1-yl)pentanamide (3S)—N-cyclobutyl-3-({1-cyclopentyl-5-[2-(trifluoromethyl)phenyl]-1H-pyrazol-3-yl}formamido)-5-[methyl(1-methylcyclopentyl)amino]pentanamide (3R)—N-cyclobutyl-3-({1-cyclopentyl-5-[2-(trifluoromethyl)phenyl]-1H-pyrazol-3-yl}formamido)-5-oxo-5-(piperidin-1-yl)pentanamide (3R)—N-cyclobutyl-3-({1-cyclopentyl-5-[2-(trifluoromethyl)phenyl]-1H-pyrazol-3-yl}formamido)-5-(3,3-difluoropiperidin-1-yl)-5-oxopentanamide (3S)—N-cyclobutyl-3-({1-cyclopentyl-5-[2-(trifluoromethyl)phenyl]-1H-pyrazol-3-yl}formamido)-5-(dimethylamino)pentanamide (3S)—N-cyclobutyl-3-({1-cyclopentyl-5-[2-(trifluoromethyl)phenyl]-1H-pyrazol-3-yl}formamido)-5-(2,2-dimethylpiperidin-1-yl)pentanamide (3R)-3-({1-cyclopentyl-5-[2-(trifluoromethyl)phenyl]-1H-pyrazol-3-yl}formamido)-4-(3,3-difluoropyrrolidin-1-yl)butanoic acid (3R)-3-({1-cyclopentyl-5-[2-(trifluoromethyl)phenyl]-1H-pyrazol-3-yl}formamido)-4-(3,3-difluoropiperidin-1-yl)butanoic acid (3S)-3-({1-cyclopentyl-5-[2-(trifluoromethyl)phenyl]-1H-pyrazol-3-yl}formamido)-N-(3,3-difluorocyclobutyl)-5-(piperidin-1-yl)pentanamide (3S)-5-{2-azabicyclo[2.2.2]octan-2-yl}-N-cyclobutyl-3-({1-cyclopentyl-5-[2-(trifluoromethyl)phenyl]-1H-pyrazol-3-yl}formamido)pentanamide (3S)—N-cyclobutyl-3-({1-cyclopentyl-5-[2-(trifluoromethyl)phenyl]-1H-pyrazol-3-yl}formamido)-5-{2-oxa-5-azaspiro[3.5]nonan-5-yl}pentanamide (3R)—N-cyclobutyl-3-({1-cyclopentyl-5-[2-(trifluoromethyl)phenyl]-1H-pyrazol-3-yl}formamido)-4-(3,3-difluoropyrrolidin-1-yl)butanamide (3R)—N-cyclobutyl-3-({1-cyclopentyl-5-[2-(trifluoromethyl)phenyl]-1H-pyrazol-3-yl}formamido)-4-(3,3-difluoropiperidin-1-yl)butanamide (2S)-3-cyclopentyl-2-({1-cyclopentyl-5-[2-(trifluoromethyl)phenyl]-1H-pyrazol-3-yl}formamido)propanoic acid (2S)-2-({1-cyclopentyl-5-[2-(trifluoromethyl)phenyl]-1H-pyrazol-3-yl}formamido)-4-methylpentanoic acid (2S)-2-({1-cyclopentyl-5-[2-(trifluoromethyl)phenyl]-1H-pyrazol-3-yl}formamido)-3-methylbutanoic acid (3S)-3-({1-cyclopentyl-5-[2-(trifluoromethyl)phenyl]-1H-pyrazol-3-yl}formamido)-5-(3,3-difluoropiperidin-1-yl)-N-(trifluoromethane)sulfonylpentanamide (3R)-4-[cyclohexyl(methyl)amino]-3-({1-cyclopentyl-5-[2-(trifluoromethyl)phenyl]-1H-pyrazol-3-yl}formamido)butanoic acid (3S)-3-({1-cyclopentyl-5-[2-(trifluoromethyl)phenyl]-1H-pyrazol-3-yl}formamido)-5-(3,3-difluoroazetidin-1-yl)pentanoic acid (3S)—N-cyclobutyl-3-({1-cyclopentyl-5-[2-(trifluoromethyl)phenyl]-1H-pyrazol-3-yl}formamido)-5-(3,3-difluoroazetidin-1-yl)pentanamide (3S)—N-cyclobutyl-3-({1-cyclopentyl-5-[2-(trifluoromethyl)phenyl]-1H-pyrazol-3-yl}formamido)-5-(cyclopentylformamido)pentanamide (3S)-3-({1-cyclopentyl-5-[2-(1,1-difluoroethyl)phenyl]-1H-pyrazol-3-yl}formamido)-5-(3,3-difluoropyrrolidin-1-yl)pentanoic acid (3S)-3-({1-cyclopentyl-5-[2-(trifluoromethyl)phenyl]-1H-pyrazol-3-yl}formamido)-5-(cyclopentylformamido)pentanoic acid (3S)—N-cyclobutyl-3-({1-cyclopentyl-5-[2-(trifluoromethyl)phenyl]-1H-pyrazol-3-yl}formamido)-5-(oxetan-3-ylformamido)pentanamide 1-cyclopentyl-N-[(2S)-4-(3,3-difluoropiperidin-1-yl)-4-oxo-1-sulfamoylbutan-2-yl]-5-[2-(trifluoromethyl)phenyl]-1H-pyrazole-3-carboxamide N-[(2S)-1-(cyclobutylsulfamoyl)-4-(3,3-difluoropiperidin-1-yl)-4-oxobutan-2-yl]-1-cyclopentyl-5-[2-(trifluoromethyl)phenyl]-1H-pyrazole-3-carboxamide (2S)-2-({1-cyclopentyl-5-[2-(trifluoromethyl)phenyl]-1H-pyrazol-3-yl}formamido)-N-(2-methoxyethyl)-N-methyl-4-phenylbutanamide (3R)-3-(cyclohexylcarbamoyl)-3-({1-cyclopentyl-5-[2-(trifluoromethyl)phenyl]-1H-pyrazol-3-yl}formamido)propanoic acid (3R)-3-({1-cyclopentyl-5-[2-(trifluoromethyl)phenyl]-1H-pyrazol-3-yl}formamido)-4-(4-fluorophenoxy)butanoic acid (3R)—N-cyclobutyl-3-({1-cyclopentyl-5-[2-(trifluoromethyl)phenyl]-1H-pyrazol-3-yl}formamido)-4-(4-fluorophenoxy)butanamide (3R)—N-cyclobutyl-4-[cyclohexyl(methyl)amino]-3-({1-cyclopentyl-5-[2-(trifluoromethyl)phenyl]-1H-pyrazol-3-yl}formamido)butanamide (3S)-3-({1-cyclopentyl-5-[2-(trifluoromethyl)phenyl]-1H-pyrazol-3-yl}formamido)-5-[(3,3-difluorocyclobutyl)amino]pentanoic acid (2R)—N-cyclobutyl-N'-cyclohexyl-2-({1-cyclopentyl-5-[2-(trifluoromethyl)phenyl]-1H-pyrazol-3-yl}formamido)butanediamide (3R)-3-({1-cyclopentyl-5-[2-(trifluoromethyl)phenyl]-1H-pyrazol-3-yl}formamido)-N-(3-methyloxetan-3-yl)-5-oxo-5-(piperidin-1-yl)pentanamide 1-cyclopentyl-N-[(2S)-4-(3,3-difluoropiperidin-1-yl)-1-(1H-1,2,3,4-tetrazol-5-yl)butan-2-yl]-5-[2-(trifluoromethyl)phenyl]-1H-pyrazole-3-carboxamide (3S)-3-({1-cyclobutyl-5-[2-(trifluoromethyl)phenyl]-1H-pyrazol-3-yl}formamido)-5-(3,3-difluoropiperidin-1-yl)pentanoic acid (3S)-5-(3,3-difluoropiperidin-1-yl)-3-{[1-(oxan-4-yl)-5-[2-(trifluoromethyl)phenyl]-1H-pyrazol-3-yl]formamido}pentanoic acid (3S)-3-({1-cyclopentyl-5-[4-fluoro-2-(trifluoromethyl)phenyl]-1H-pyrazol-3-yl}formamido)-5-(3,3-difluoropiperidin-1-yl)pentanoic acid (3S)-3-({5-[4-chloro-2-(trifluoromethyl)phenyl]-1-cyclopentyl-1H-pyrazol-3-yl}formamido)-5-(3,3-difluoropiperidin-1-yl)pentanoic acid (3S)-3-({5-[2-chloro-6-(trifluoromethyl)phenyl]-1-cyclopentyl-1H-pyrazol-3-yl}formamido)-5-(3,3-difluoropiperidin-1-yl)pentanoic acid (3S)-3-{[1-(cyclopropylmethyl)-5-[2-(trifluoromethyl)phenyl]-1H-pyrazol-3-yl]formamido}-5-(3,3-difluoropiperidin-1-yl)pentanoic acid (3R)-3-[cyclohexyl(methyl)carbamoyl]-3-({1-cyclopentyl-5-[2-(trifluoromethyl)phenyl]-1H-pyrazol-3-yl}formamido)propanoic acid (3R)-3-({1-cyclopentyl-5-[2-(trifluoromethyl)phenyl]-1H-pyrazol-3-yl}formamido)-3-[(oxan-4-yl)carbamoyl]propanoic acid (3R)-3-({1-cyclopentyl-5-[2-(trifluoromethyl)phenyl]-1H-pyrazol-3-yl}formamido)-3-[(4-fluorophenyl)carbamoyl]propanoic acid (2R)—N-cyclobutyl-N'-cyclohexyl-2-({1-cyclopentyl-5-[2-(trifluoromethyl)phenyl]-1H-pyrazol-3-yl}formamido)-N'-methylbutanediamide (2R)—N-cyclobutyl-2-({1-cyclopentyl-5-[2-(trifluoromethyl)phenyl]-1H-pyrazol-3-yl}formamido)-N'-(oxan-4-yl)butanediamide 1-cyclopentyl-N-[(3R)-1-(4-fluorophenyl)-2,5-dioxopyrrolidin-3-yl]-5-[2-(trifluoromethyl)phenyl]-1H-pyrazole-3-carboxamide (3S)-5-(3,3-difluoropiperidin-1-yl)-3-{[1-(2-methylpropyl)-5-[2-(trifluoromethyl)phenyl]-1H-pyrazol-3-yl]formamido}pentanoic acid (3S)-3-({1-cyclopentyl-5-[2-(trifluoromethyl)phenyl]-1H-pyrazol-3-yl}formamido)-5-(3,3,4,4,5,5-hexafluoropiperidin-1-yl)pentanoic acid (3S)-3-({1-cyclopentyl-5-[2-(trifluoromethyl)phenyl]-1H-pyrazol-3-yl}formamido)-5-(3,3-difluoropyrrolidin-1-yl)hexanoic acid (3S)-5-(3,3-difluoropiperidin-1-yl)-3-{[1-(2,2-dimethylpropyl)-5-[2-(trifluoromethyl)phenyl]-1H-pyrazol-3-yl]formamido}pentanoic acid (2S)-2-({1-cyclopentyl-5-[2-(trifluoromethyl)phenyl]-1H-pyrazol-3-yl}formamido)-N-(2-methoxyethyl)-N-methyl-3-phenoxypropanamide (3S)-3-{[1-(cyclobutylmethyl)-5-[2-(trifluoromethyl)phenyl]-1H-pyrazol-3-yl]formamido}-5-(3,3-difluoropiperidin-1-yl)pentanoic acid (3S,5S)-3-({1-cyclopentyl-5-[2-(trifluoromethyl)phenyl]-1H-pyrazol-3-yl}formamido)-5-(3,3-difluoropyrrolidin-1-yl)hexanoic acid (3S)—N-cyclobutyl-3-({1-cyclopentyl-5-[2-(trifluoromethyl)phenyl]-1H-pyrazol-3-yl}formamido)-5-(3,3-difluoropyrrolidin-1-yl)hexanamide (3S)-3-({1-cyclopentyl-5-[2-(trifluoromethyl)phenyl]-1H-pyrazol-3-yl}formamido)-5-(3,3,4,4-tetrafluoropyrrolidin-1-yl)pentanoic acid (3S,5R)-3-({1-cyclopentyl-5-[2-(trifluoromethyl)phenyl]-1H-pyrazol-3-yl}formamido)-5-(3,3-difluoropiperidin-1-yl)hexanoic acid (3S,5S)-3-({1-cyclopentyl-5-[2-(trifluoromethyl)phenyl]-1H-pyrazol-3-yl}formamido)-5-(3,3-difluoropiperidin-1-yl)hexanoic acid (2S)-3-cyclohexyl-2-({1-cyclopentyl-5-[2-(trifluoromethyl)phenyl]-1H-pyrazol-3-yl}formamido)propanoic acid (3S)-3-({1-cyclopentyl-5-[2-(trifluoromethyl)phenyl]-1H-pyrazol-3-yl}formamido)-5-[3-(trifluoromethyl)pyrrolidin-1-yl]pentanoic acid (3R)-3-({1-cyclopentyl-5-[2-(trifluoromethyl)phenyl]-1H-pyrazol-3-yl}formamido)-5-(3,3-difluoropiperidin-1-yl)pentanoic acid (3S)-5-(3,3-difluoropiperidin-1-yl)-3-({1-propyl-5-[2-(trifluoromethyl)phenyl]-1H-pyrazol-3-yl}formamido)pentanoic acid (3S)-3-({1-cyclopentyl-5-[2-(trifluoromethyl)phenyl]-1H-pyrazol-3-yl}formamido)-5-[(3R,4S)-3,4-difluoropyrrolidin-1-yl]pentanoic acid (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid (3S)-3-({1-cyclopentyl-5-[2-(trifluoromethyl)phenyl]-1H-pyrazol-3-yl}formamido)-5-[(3S)-3-fluoropiperidin-1-yl]pentanoic acid (3S)-3-({1-cyclopentyl-5-[2-(trifluoromethyl)phenyl]-1H-pyrazol-3-yl}formamido)-5-[(3R)-3-fluoropiperidin-1-yl]pentanoic acid (3S)-3-({1-cyclopentyl-5-[2-(trifluoromethyl)phenyl]-1H-pyrazol-3-yl}formamido)-5-[(3S)-3-fluoropyrrolidin-1-yl]pentanoic acid (3S)-3-({1-cyclopentyl-5-[2-(trifluoromethyl)phenyl]-1H-pyrazol-3-yl}formamido)-5-(2-oxopiperidin-1-yl)pentanoic acid (3S)-3-({1-cyclopentyl-5-[2-(trifluoromethyl)phenyl]-1H-pyrazol-3-yl}formamido)-5-(3,3-dimethylazetidin-1-yl)pentanoic acid (3S)-3-({1-cyclopentyl-5-[2-(1,1-difluoroethyl)phenyl]-1H-pyrazol-3-yl}formamido)-5-(3,3-difluoroazetidin-1-yl)pentanoic acid (3S)-3-({1-cyclopentyl-5-[2-(trifluoromethyl)phenyl]-1H-pyrazol-3-yl}formamido)-5-[(3R)-3-fluoropyrrolidin-1-yl]pentanoic acid (3S)-3-({1-cyclopentyl-5-[2-(trifluoromethyl)phenyl]-1H-pyrazol-3-yl}formamido)-5-{5,5-difluoro-2-azaspiro[3.3]heptan-2-yl}pentanoic acid (2S)-3-(tert-butoxy)-2-({1-cyclopentyl-5-[2-(trifluoromethyl)phenyl]-1H-pyrazol-3-yl}formamido)-N-(2-methoxyethyl)-N-methylpropanamide (3S)-3-({1-cyclopentyl-5-[2-(1,1-difluoroethyl)phenyl]-1H-pyrazol-3-yl}formamido)-5-[(3R)-3-fluoropiperidin-1-yl]pentanoic acid (3S)-3-({1-cyclopentyl-5-[2-(1,1-difluoroethyl)phenyl]-1H-pyrazol-3-yl}formamido)-5-[trans-3,4-difluoropyrrolidin-1-yl]pentanoic acid (3S)-3-({1-cyclopentyl-5-[2-(1,1-difluoroethyl)phenyl]-1H-pyrazol-3-yl}formamido)-5-[trans-3,4-dimethylpyrrolidin-1-yl]hexanoic acid (2S,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid (2R,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid (3S)-3-({1-cyclopentyl-5-[2-(1,1-difluoroethyl)phenyl]-1H-pyrazol-3-yl}formamido)-5-[cis-3,4-difluoropyrrolidin-1-yl]pentanoic acid (3S,5R)-3-({1-cyclopentyl-5-[2-(1,1-difluoroethyl)phenyl]-1H-pyrazol-3-yl}formamido)-5-[trans-3,4-difluoropyrrolidin-1-yl]hexanoic acid (3S,5S)-3-({1-cyclopentyl-5-[2-(1,1-difluoroethyl)phenyl]-1H-pyrazol-3-yl}formamido)-5-(3,3-difluoropyrrolidin-1-yl)hexanoic acid (3S)-3-({1-cyclopentyl-5-[2-(trifluoromethyl)phenyl]-1H-pyrazol-3-yl}formamido)-5-[3-(trifluoromethyl)azetidin-1-yl]pentanoic acid (3S)-3-({1-cyclopentyl-5-[2-(trifluoromethyl)phenyl]-1H-pyrazol-3-yl}formamido)-5-{3,3-difluoro-8-azabicyclo[3.2.1]octan-8-yl}pentanoic acid (3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}pentanoic acid (3S)-3-({1-cyclopentyl-5-[2-(trifluoromethyl)phenyl]-1H-pyrazol-3-yl}formamido)-5-(2,6-dioxopiperidin-1-yl)pentanoic acid (3S)-3-({1-cyclopentyl-5-[2-(1,1-difluoroethyl)phenyl]-1H-pyrazol-3-yl}formamido)-5-[(2R)-4,4-difluoro-2-methylpyrrolidin-1-yl]pentanoic acid (3S)-3-({1-cyclopentyl-5-[2-(trifluoromethyl)phenyl]-1H-pyrazol-3-yl}formamido)-5-{8,8-difluoro-3-azabicyclo[3.2.1]octan-3-yl}pentanoic acid (3S)-3-({1-cyclopentyl-5-[2-(1,1-difluoroethyl)phenyl]-1H-pyrazol-3-yl}formamido)-5-(5,5-difluoro-2-methylpiperidin-1-yl)pentanoic acid (3S)-3-({1-cyclopentyl-5-[2-(trifluoromethyl)phenyl]-1H-pyrazol-3-yl}formamido)-5-(2,2-dimethyl-4-oxopyrrolidin-1-yl)pentanoic acid (3S)-3-({1-cyclopentyl-5-[2-(trifluoromethyl)phenyl]-1H-pyrazol-3-yl}formamido)-5-(3-fluoro-3-methylpyrrolidin-1-yl)pentanoic acid (3S)-3-({1-cyclopentyl-5-[2-(trifluoromethyl)phenyl]-1H-pyrazol-3-yl}formamido)-5-[(3S,4R)-3,4-difluoropiperidin-1-yl]pentanoic acid (3S)-3-({1-cyclopentyl-5-[2-(1,1-difluoroethyl)phenyl]-1H-pyrazol-3-yl}formamido)-5-(2,2-dimethyl-4-oxopiperidin-1-yl)pentanoic acid (3S)-3-({1-cyclopentyl-5-[2-(trifluoromethyl)phenyl]-1H-pyrazol-3-yl}formamido)-5-(4,4-difluoro-2,2-dimethylpyrrolidin-1-yl)pentanoic acid (3S)-3-({1-cyclopentyl-5-[2-(trifluoromethyl)phenyl]-1H-pyrazol-3-yl}formamido)-5-(3-fluoro-3-methylpiperidin-1-yl)pentanoic acid trifluoroacetate (3S)-3-({1-cyclopentyl-5-[2-(trifluoromethyl)phenyl]-1H-pyrazol-3-yl}formamido)-5-[(3S)-3-fluoro-3-methylpiperidin-1-yl]pentanoic acid (3S)-3-({1-cyclopentyl-5-[2-(trifluoromethyl)phenyl]-1H-pyrazol-3-yl}formamido)-5-{[1-(trifluoromethyl)cyclopentyl]amino}pentanoic acid trifluoroacetate (3S)—N-cyclobutyl-5-cyclohexyl-3-{[5-(2,6-dimethoxyphenyl)-1-(4-fluorophenyl)-1H-pyrazol-3-yl]formamido}pentanamide (3S)-5-cyclohexyl-3-{[1-cyclopentyl-5-(2,6-dimethoxyphenyl)-1H-pyrazol-3-yl]formamido}pentanoic acid (3S)-5-cyclohexyl-3-{[1-cyclohexyl-5-(2,6-dimethoxyphenyl)-1H-pyrazol-3-yl]formamido}pentanoic acid (3S)-5-cyclohexyl-3-{[5-(2,6-dimethoxyphenyl)-1-propyl-1H-pyrazol-3-yl]formamido}pentanoic acid (3S)—N-cyclobutyl-5-cyclohexyl-3-{[1-cyclopentyl-5-(2,6-dimethoxyphenyl)-1H-pyrazol-3-yl]formamido}pentanamide (3S)—N-cyclobutyl-5-cyclohexyl-3-{[1-cyclohexyl-5-(2,6-dimethoxyphenyl)-1H-pyrazol-3-yl]formamido}pentanamide (3S)—N-cyclobutyl-5-cyclohexyl-3-{[5-(2,6-dimethoxyphenyl)-1-propyl-1H-pyrazol-3-yl]formamido}pentanamide 1-cyclopentyl-N-[(2S)-4-{6,6-difluoro-3-azabicyclo[3.1.0]hexan-3-yl}-1-(1H-1,2,3,4-tetrazol-5-yl)butan-2-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid 1-cyclopentyl-N-[(2S)-4-[(3S,4S)-3,4-difluoropyrrolidin-1-yl]-1-(1H-1,2,3,4-tetrazol-5-yl)butan-2-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-[(3R,4R)-3,4-difluoropyrrolidin-1-yl]pentanoic acid (2S,3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanoic acid (2R,3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanoic acid (3S)—N-cyclobutyl-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanamide 1-cyclopentyl-N-[(3S)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide 1-cyclopentyl-N-[(3S,4R)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide (3S)-3-({1-cyclopentyl-5-[2-(trifluoromethyl)phenyl]-1H-pyrazol-3-yl}formamido)-5-(3,5-difluoropiperidin-1-yl)pentanoic acid 1-cyclopentyl-N-[(2S)-4-(3,3-difluoropiperidin-1-yl)-1-(1H-1,2,3,4-tetrazol-5-yl)butan-2-yl]-5-[3-(trifluoromethyl)pyridin-2-yl]-1H-pyrazole-3-carboxamide (3S)-3-({1-cyclopentyl-5-[2-(trifluoromethyl)phenyl]-1H-pyrazol-3-yl}formamido)-5-(2,5-dioxopyrrolidin-1-yl)pentanoic acid (3S)-5-cyclohexyl-3-{[5-(2,6-dimethoxyphenyl)-1-methyl-1H-pyrazol-3-yl]formamido}pentanoic acid (3S)-5-cyclohexyl-3-{[1-cyclooctyl-5-(2,6-dimethoxyphenyl)-1H-pyrazol-3-yl]formamido}pentanoic acid (3S)-5-cyclohexyl-3-{[1-(cyclohexylmethyl)-5-(2,6-dimethoxyphenyl)-1H-pyrazol-3-yl]formamido}pentanoic acid (3S)-5-cyclohexyl-3-{[5-(2,6-dimethoxyphenyl)-1-(pentan-3-yl)-1H-pyrazol-3-yl]formamido}pentanoic acid 1-cyclopentyl-N-[(2S)-4-(2,6-dioxopiperidin-1-yl)-1-(1H-1,2,3,4-tetrazol-5-yl)butan-2-yl]-5-[2-(trifluoromethyl)phenyl]-1H-pyrazole-3-carboxamide or a pharmaceutically acceptable salt, prodrug, or salt of a prodrug thereof.

4. The method of claim 1, wherein capillary function is improved.

5. The method of claim 1, wherein receptor occupancy is prolonged.

6. The method of claim 1, wherein the apelin receptor agonist is dosed as an aerosol.

7. The method of claim 1, wherein the apelin receptor agonist is dosed at a dosage of 7.5 mg/kg, 15 mg/kg, or 30 mg/kg.

8. The method of claim 1, further comprising administering one or more additional agent.

9. The method of claim 8, wherein the additional agent is one or more of perfenidone, nintedinib, one or more corticosteroids, and one or more antibiotics.

10. The method of claim 1, wherein the mean survival time of the patient is improved.

11. The method of claim 1, wherein the apelin receptor agonist is administered to the patient twice a day.

12. The method of claim 1, wherein the method comprises reducing an Ashcroft score.

13. The method of claim 1, wherein the method comprises blocking epithelial cell injury.

14. The method of claim 1, wherein the method comprises preventing fibrosis formation.

15. The method of claim 1, wherein the method comprises reducing apoptosis.

16. The method of claim 1, wherein the method comprises regenerating vascularization.

* * * * *